United States Patent
Duvick et al.

(10) Patent No.: US 6,211,435 B1
(45) Date of Patent: *Apr. 3, 2001

(54) AMINO POLYOL AMINE OXIDASE POLYNUCLEOTIDES AND RELATED POLYPEPTIDES AND METHODS OF USE

(75) Inventors: Jonathan P. Duvick, Des Moines; Jacob T. Gilliam, Norwalk; Joyce R. Maddox, Des Moines, all of IA (US); Oswald R. Crasta, Branford; Otto Folkerts, Guilford, both of CT (US)

(73) Assignees: Pioneer Hi-Bred International, Inc., Des Moines, IA (US); CuraGen Corporation, New Haven, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/352,168

(22) Filed: Jul. 12, 1999

Related U.S. Application Data
(60) Provisional application No. 60/092,936, filed on Jul. 15, 1998.

(51) Int. Cl.$^7$ ............... C12N 5/04; C12N 15/09; C12N 15/31; C12N 15/82; A01H 5/00
(52) U.S. Cl. ............ 800/279; 800/278; 800/320.1; 800/320.2; 800/320.3; 800/317.4; 800/314; 800/312; 800/322; 800/306; 800/320; 800/288; 435/468; 435/419; 435/183; 435/195; 435/196; 435/320.1; 435/69.1; 435/69.7; 435/69.8; 435/411; 435/412; 435/415; 435/416; 435/427; 536/23.2; 536/24.1; 536/23.7
(58) Field of Search ............ 800/278, 279, 800/320.1, 320.2, 320.3, 317.4, 314, 312, 322, 306, 320, 288; 536/23.2, 24.1, 23.7; 435/468, 419, 183, 195, 196, 320.1, 69.1, 69.7, 69.8, 411, 412, 415, 416, 427

(56) References Cited

U.S. PATENT DOCUMENTS

| | | | |
|---|---|---|---|
| 4,988,586 | 1/1991 | Toyoda et al. | 424/93.2 |
| 5,178,863 | 1/1993 | Toyoda et al. | 424/93.48 |
| 5,262,306 | 11/1993 | Robeson et al. | 435/29 |
| 5,716,820 | 2/1998 | Duvick et al. | 435/196 |
| 5,792,931 * | 8/1998 | Duvick et al. | 800/205 |
| 5,962,229 * | 10/1999 | McGonigle et al. | 435/6 |

FOREIGN PATENT DOCUMENTS

| | | |
|---|---|---|
| 93 02673 | 2/1993 | (WO). |
| 95 06128 | 3/1995 | (WO). |
| 95 06415 | 3/1995 | (WO). |
| 96 06175 | 2/1996 | (WO). |
| 96 12414 | 5/1996 | (WO). |
| 96 20595 | 7/1996 | (WO). |
| 96 32007 | 10/1996 | (WO). |
| 99 02703 | 1/1999 | (WO). |

OTHER PUBLICATIONS

Malone J. A. Accession No. U13849, Deposited, Dec. 1994.*
Bennetzen et al. Genetic Engineering, vol. 14, pp. 99–124, 1992.*
Linthorst et al. The Plant Cell, vol. 1, pp. 285–291, Mar. 1989.*
Chaumont et al. Plant Molecular Biology, vol. 24, pp. 631–641, 1994.*
Tavladoraki, et al., 1998, *FEBS Letters*, 426: 62–66, "Maize polyamine oxidase: primary structure from protein and cDNA sequencing".
Binda, et al., 1999, *Structure*, 7(3): 265–276, "A 30 A long U–shaped catalytic tunnel in the crystal structure of polyamine oxidase".
Federico, et al., 1992, *Phytochemistry*, 31: 2955–2957, "Polyamine Oxidase Bound to Cell Walls From Zea Mays Seedlings".
Angelini, et al., 1995, *J. Plant Physiol.*, 145: 686–692, "Maize Polyamine Oxidase: Antibody Production and Ultrastructure Localization".

* cited by examiner

*Primary Examiner*—David T. Fox
*Assistant Examiner*—Medina A. Ibrahim
(74) *Attorney, Agent, or Firm*—Pioneer Hi-Bred International, Inc.

(57) ABSTRACT

The present invention provides polynucleotides and related polypeptides of the enzyme APAO isolated from *Exophiala spinifera*. Additionally, the polynucleotide encoding for the APAO enzyme can be used to transform plant cells normally susceptible to Fusarium or other toxin-producing fungus infection. Plants can be regenerated from the transformed plant cells. Additionally, the present invention provides for expressing both APAO and a fumonisin esterase in a transgenic plant. In this way, a transgenic plant can be produced with the capability of degrading fumonisin, as well as with the capability of producing the degrading enzymes. In addition, the present invention provides methods for producing the APAO enzyme in both prokaryotic and non-plant eukaryotic systems. Methods for detoxification in grain, grain processing, silage, food crops and in animal feed and rumen microbes are also disclosed.

14 Claims, No Drawings

SEQUENCE LISTING

```
<160> NUMBER OF SEQ ID NOS: 33

<210> SEQ ID NO 1
<211> LENGTH: 372
<212> TYPE: DNA
<213> ORGANISM: Exophiala spinifera.
<220> FEATURE:
<221> NAME/KEY: misc_feature
<222> LOCATION: (346)...(346)
```

-continued

```
<223> OTHER INFORMATION: n = A,T,C or G

<400> SEQUENCE: 1
gggccccggc gttctcgtag gctgcgcgga gttggtccca gacagacttt tgtcgtacct    60
gcttggactg ttgggaccac ttccgtcccg ggtctccgac catgaaacag gtaatggacc    120
attgtcgatc gacgtcgatg ctggtatctc tggcaaatga gatggggtca cagctcgatt    180
ggaggacgcc cgagaagcct tgttcgcgcc accacggctt gtcccatacg aagactatct    240
tgctatagta gcccaggata gaattttccg ccaatgcttg cttctcggcg ggaagaggtg    300
gtgaaaatgt caaggtggga tacaaggttg tcggtaacga aaccancacc ttttttgcttc    360 ggaacacggc gc                                                         372

<210> SEQ ID NO 2
<211> LENGTH: 182
<212> TYPE: DNA
<213> ORGANISM: Exophiala spinifera.

<400> SEQUENCE: 2
gaattttccg ccaatgcttg cttctcggcg ggaagaggtg gtgaaaatgt caaggtggga    60
tacaaggttg tcggtaacga aaccaccacc ttttttgcttc ggaacacggc gcccgaggcc    120
gatcgtactg tacagccgga tgccgactgc tcaatttcag cgacggggt gttgaggtgc    180 ac                                                                    182

<210> SEQ ID NO 3
<211> LENGTH: 29
<212> TYPE: DNA
<213> ORGANISM: Artificial Sequence
<220> FEATURE:
<223> OTHER INFORMATION: Designed oligonucleotide for 3' RACE, N21965

<400> SEQUENCE: 3
tggtttcgtt accgacaacc ttgtatccc                                       29

<210> SEQ ID NO 4
<211> LENGTH: 28
<212> TYPE: DNA
<213> ORGANISM: Artificial Sequence
<220> FEATURE:
<223> OTHER INFORMATION: Designed oligonucleotide for 5' RACE, N21968

<400> SEQUENCE: 4
gagttggtcc cagacagact tttgtcgt                                        28

<210> SEQ ID NO 5
<211> LENGTH: 1389
<212> TYPE: DNA
<213> ORGANISM: Exophiala spinifera
<220> FEATURE:
<221> NAME/KEY: CDS
<222> LOCATION: (1)...(1386)

<400> SEQUENCE: 5 gac aac gtt gcg gac gtg gta gtg gtg ggc gct ggc ttg agc ggt ttg      48
Asp Asn Val Ala Asp Val Val Val Val Gly Ala Gly Leu Ser Gly Leu
  1               5                  10                  15 gag acg gca cgc aaa gtc cag gcc gcc ggt ctg tcc tgc ctc gtt ctt      96
Glu Thr Ala Arg Lys Val Gln Ala Ala Gly Leu Ser Cys Leu Val Leu
                 20                  25                  30 gag gcg atg gat cgt gta ggg gga aag act ctg agc gta caa tcg ggt     144
Glu Ala Met Asp Arg Val Gly Gly Lys Thr Leu Ser Val Gln Ser Gly
```

-continued

```
                35                        40                         45
ccc ggc agg acg act atc aac gac ctc ggc gct gcg tgg atc aat gac         192
Pro Gly Arg Thr Thr Ile Asn Asp Leu Gly Ala Ala Trp Ile Asn Asp
         50                    55                       60 agc aac caa agc gaa gta tcc aga ttg ttt gaa aga ttt cat ttg gag         240
Ser Asn Gln Ser Glu Val Ser Arg Leu Phe Glu Arg Phe His Leu Glu
 65                    70                       75                 80 ggc gag ctc cag agg acg act gga aat tca atc cat caa gca caa gac         288
Gly Glu Leu Gln Arg Thr Thr Gly Asn Ser Ile His Gln Ala Gln Asp
                 85                       90                  95 ggt aca acc act aca gct cct tat ggt gac tcc ttg ctg agc gag gag         336
Gly Thr Thr Thr Thr Ala Pro Tyr Gly Asp Ser Leu Leu Ser Glu Glu
                       100                  105                      110 gtt gca agt gca ctt gcg gaa ctc ctc ccc gta tgg tct cag ctg atc         384
Val Ala Ser Ala Leu Ala Glu Leu Leu Pro Val Trp Ser Gln Leu Ile
                 115                      120                 125 gaa gag cat agc ctt caa gac ctc aag gcg agc cct cag gcg aag cgg         432
Glu Glu His Ser Leu Gln Asp Leu Lys Ala Ser Pro Gln Ala Lys Arg
         130                      135                 140 ctc gac agt gtg agc ttc gcg cac tac tgt gag aag gaa cta aac ttg         480
Leu Asp Ser Val Ser Phe Ala His Tyr Cys Glu Lys Glu Leu Asn Leu
145                      150                 155                      160 cct gct gtt ctc ggc gta gca aac cag atc aca cgc gct ctg ctc ggt         528
Pro Ala Val Leu Gly Val Ala Asn Gln Ile Thr Arg Ala Leu Leu Gly
                 165                      170                 175 gtg gaa gcc cac gag atc agc atg ctt ttt ctc acc gac tac atc aag         576
Val Glu Ala His Glu Ile Ser Met Leu Phe Leu Thr Asp Tyr Ile Lys
         180                      185                 190 agt gcc acc ggt ctc agt aat att ttc tcg gac aag aaa gac ggc ggg         624
Ser Ala Thr Gly Leu Ser Asn Ile Phe Ser Asp Lys Lys Asp Gly Gly
         195                      200                 205 cag tat atg cga tgc aaa aca ggt atg cag tcg att tgc cat gcc atg         672
Gln Tyr Met Arg Cys Lys Thr Gly Met Gln Ser Ile Cys His Ala Met
         210                      215                 220 tca aag gaa ctt gtt cca ggc tca gtg cac ctc aac acc ccc gtc gct         720
Ser Lys Glu Leu Val Pro Gly Ser Val His Leu Asn Thr Pro Val Ala
225                      230                 235                      240 gaa att gag cag tcg gca tcc ggc tgt aca gta cga tcg gcc tcg ggc         768
Glu Ile Glu Gln Ser Ala Ser Gly Cys Thr Val Arg Ser Ala Ser Gly
                 245                      250                 255 gcc gtg ttc cga agc aaa aag gtg gtg gtt tcg tta ccg aca acc ttg         816
Ala Val Phe Arg Ser Lys Lys Val Val Val Ser Leu Pro Thr Thr Leu
         260                      265                 270 tat ccc acc ttg aca ttt tca cca cct ctt ccc gcc gag aag caa gca         864
Tyr Pro Thr Leu Thr Phe Ser Pro Pro Leu Pro Ala Glu Lys Gln Ala
         275                      280                 285 ttg gcg gaa aat tct atc ctg ggc tac tat agc aag ata gtc ttc gta         912
Leu Ala Glu Asn Ser Ile Leu Gly Tyr Tyr Ser Lys Ile Val Phe Val
         290                      295                 300 tgg gac aag ccg tgg tgg cgc gaa caa ggc ttc tcg ggc gtc ctc caa         960
Trp Asp Lys Pro Trp Trp Arg Glu Gln Gly Phe Ser Gly Val Leu Gln
305                      310                 315                      320 tcg agc tgt gac ccc atc tca ttt gcc aga gat acc agc atc gac gtc        1008
Ser Ser Cys Asp Pro Ile Ser Phe Ala Arg Asp Thr Ser Ile Asp Val
                 325                      330                 335 gat cga caa tgg tcc att acc tgt ttc atg gtc gga gac ccg gga cgg        1056
Asp Arg Gln Trp Ser Ile Thr Cys Phe Met Val Gly Asp Pro Gly Arg
         340                      345                 350 aag tgg tcc caa cag tcc aag cag gta cga caa aag tct gtc tgg gac        1104
```

```
Lys Trp Ser Gln Gln Ser Lys Gln Val Arg Gln Lys Ser Val Trp Asp
            355                 360                 365 caa ctc cgc gca gcc tac gag aac gcc ggg gcc caa gtc cca gag ccg   1152
Gln Leu Arg Ala Ala Tyr Glu Asn Ala Gly Ala Gln Val Pro Glu Pro
370                 375                 380 gcc aac gtg ctc gaa atc gag tgg tcg aag cag cag tat ttc caa gga   1200
Ala Asn Val Leu Glu Ile Glu Trp Ser Lys Gln Gln Tyr Phe Gln Gly
385                 390                 395                 400 gct ccg agc gcc gtc tat ggg ctg aac gat ctc atc aca ctg ggt tcg   1248
Ala Pro Ser Ala Val Tyr Gly Leu Asn Asp Leu Ile Thr Leu Gly Ser
                405                 410                 415 gcg ctc aga acg ccg ttc aag agt gtt cat ttc gtt gga acg gag acg   1296
Ala Leu Arg Thr Pro Phe Lys Ser Val His Phe Val Gly Thr Glu Thr
            420                 425                 430 tct tta gtt tgg aaa ggg tat atg gaa ggg gcc ata cga tcg ggt caa   1344
Ser Leu Val Trp Lys Gly Tyr Met Glu Gly Ala Ile Arg Ser Gly Gln
                435                 440                 445 cga ggt gct gca gaa gtt gtg gct agc ctg gtg cca gca gca             1386
Arg Gly Ala Ala Glu Val Val Ala Ser Leu Val Pro Ala Ala
    450                 455                 460 tag                                                                 1389

<210> SEQ ID NO 6
<211> LENGTH: 462
<212> TYPE: PRT
<213> ORGANISM: Exophiala spinifera

<400> SEQUENCE: 6

Asp Asn Val Ala Asp Val Val Val Gly Ala Gly Leu Ser Gly Leu
1               5                   10                  15

Glu Thr Ala Arg Lys Val Gln Ala Ala Gly Leu Ser Cys Leu Val Leu
            20                  25                  30

Glu Ala Met Asp Arg Val Gly Gly Lys Thr Leu Ser Val Gln Ser Gly
        35                  40                  45

Pro Gly Arg Thr Thr Ile Asn Asp Leu Gly Ala Ala Trp Ile Asn Asp
    50                  55                  60

Ser Asn Gln Ser Glu Val Ser Arg Leu Phe Glu Arg Phe His Leu Glu
65                  70                  75                  80

Gly Glu Leu Gln Arg Thr Thr Gly Asn Ser Ile His Gln Ala Gln Asp
                85                  90                  95

Gly Thr Thr Thr Thr Ala Pro Tyr Gly Asp Ser Leu Leu Ser Glu Glu
            100                 105                 110

Val Ala Ser Ala Leu Ala Glu Leu Leu Pro Val Trp Ser Gln Leu Ile
        115                 120                 125

Glu Glu His Ser Leu Gln Asp Leu Lys Ala Ser Pro Gln Ala Lys Arg
    130                 135                 140

Leu Asp Ser Val Ser Phe Ala His Tyr Cys Glu Lys Glu Leu Asn Leu
145                 150                 155                 160

Pro Ala Val Leu Gly Val Ala Asn Gln Ile Thr Arg Ala Leu Leu Gly
                165                 170                 175

Val Glu Ala His Glu Ile Ser Met Leu Phe Leu Thr Asp Tyr Ile Lys
            180                 185                 190

Ser Ala Thr Gly Leu Ser Asn Ile Phe Ser Asp Lys Lys Asp Gly Gly
        195                 200                 205

Gln Tyr Met Arg Cys Lys Thr Gly Met Gln Ser Ile Cys His Ala Met
    210                 215                 220
```

-continued

```
Ser Lys Glu Leu Val Pro Gly Ser Val His Leu Asn Thr Pro Val Ala
225                 230                 235                 240

Glu Ile Glu Gln Ser Ala Ser Gly Cys Thr Val Arg Ser Ala Ser Gly
            245                 250                 255

Ala Val Phe Arg Ser Lys Lys Val Val Ser Leu Pro Thr Thr Leu
        260                 265                 270

Tyr Pro Thr Leu Thr Phe Ser Pro Pro Leu Pro Ala Glu Lys Gln Ala
    275                 280                 285

Leu Ala Glu Asn Ser Ile Leu Gly Tyr Tyr Ser Lys Ile Val Phe Val
290                 295                 300

Trp Asp Lys Pro Trp Trp Arg Glu Gln Gly Phe Ser Gly Val Leu Gln
305                 310                 315                 320

Ser Ser Cys Asp Pro Ile Ser Phe Ala Arg Asp Thr Ser Ile Asp Val
            325                 330                 335

Asp Arg Gln Trp Ser Ile Thr Cys Phe Met Val Gly Asp Pro Gly Arg
        340                 345                 350

Lys Trp Ser Gln Gln Ser Lys Gln Val Arg Gln Lys Ser Val Trp Asp
    355                 360                 365

Gln Leu Arg Ala Ala Tyr Glu Asn Ala Gly Ala Gln Val Pro Glu Pro
370                 375                 380

Ala Asn Val Leu Glu Ile Glu Trp Ser Lys Gln Gln Tyr Phe Gln Gly
385                 390                 395                 400

Ala Pro Ser Ala Val Tyr Gly Leu Asn Asp Leu Ile Thr Leu Gly Ser
            405                 410                 415

Ala Leu Arg Thr Pro Phe Lys Ser Val His Phe Val Gly Thr Glu Thr
        420                 425                 430

Ser Leu Val Trp Lys Gly Tyr Met Glu Gly Ala Ile Arg Ser Gly Gln
    435                 440                 445

Arg Gly Ala Ala Glu Val Val Ala Ser Leu Val Pro Ala Ala
450                 455                 460
```

<210> SEQ ID NO 7
<211> LENGTH: 1442
<212> TYPE: DNA
<213> ORGANISM: Exophiala spinifera
<220> FEATURE:
<221> NAME/KEY: CDS
<222> LOCATION: (1)...(646)
<221> NAME/KEY: intron
<222> LOCATION: (647)...(699)
<221> NAME/KEY: CDS
<222> LOCATION: (700)...(1439)

<400> SEQUENCE: 7

```
gac aac gtt gcg gac gtg gta gtg gtg ggc gct ggc ttg agc ggt ttg      48
Asp Asn Val Ala Asp Val Val Val Val Gly Ala Gly Leu Ser Gly Leu
 1               5                  10                  15 gag acg gca cgc aaa gtc cag gcc gcc ggt ctg tcc tgc ctc gtt ctt      96
Glu Thr Ala Arg Lys Val Gln Ala Ala Gly Leu Ser Cys Leu Val Leu
            20                  25                  30 gag gcg atg gat cgt gta ggg gga aag act ctg agc gta caa tcg ggt     144
Glu Ala Met Asp Arg Val Gly Gly Lys Thr Leu Ser Val Gln Ser Gly
        35                  40                  45 ccc ggc agg acg act atc aac gac ctc ggc gct gcg tgg atc aat gac     192
Pro Gly Arg Thr Thr Ile Asn Asp Leu Gly Ala Ala Trp Ile Asn Asp
    50                  55                  60 agc aac caa agc gaa gta tcc aga ttg ttt gaa aga ttt cat ttg gag     240
Ser Asn Gln Ser Glu Val Ser Arg Leu Phe Glu Arg Phe His Leu Glu
65                  70                  75                  80
```

```
ggc gag ctc cag agg acg act gga aat tca atc cat caa gca caa gac      288
Gly Glu Leu Gln Arg Thr Thr Gly Asn Ser Ile His Gln Ala Gln Asp
             85                  90                  95 ggt aca acc act aca gct cct tat ggt gac tcc ttg ctg agc gag gag      336
Gly Thr Thr Thr Thr Ala Pro Tyr Gly Asp Ser Leu Leu Ser Glu Glu
                100                 105                 110 gtt gca agt gca ctt gcg gaa ctc ctc ccc gta tgg tct cag ctg atc      384
Val Ala Ser Ala Leu Ala Glu Leu Leu Pro Val Trp Ser Gln Leu Ile
            115                 120                 125 gaa gag cat agc ctt caa gac ctc aag gcg agc cct cag gcg aag cgg      432
Glu Glu His Ser Leu Gln Asp Leu Lys Ala Ser Pro Gln Ala Lys Arg
        130                 135                 140 ctc gac agt gtg agc ttc gcg cac tac tgt gag aag gaa cta aac ttg      480
Leu Asp Ser Val Ser Phe Ala His Tyr Cys Glu Lys Glu Leu Asn Leu
145                 150                 155                 160 cct gct gtt ctc ggc gta gca aac cag atc aca cgc gct ctg ctc ggt      528
Pro Ala Val Leu Gly Val Ala Asn Gln Ile Thr Arg Ala Leu Leu Gly
                165                 170                 175 gtg gaa gcc cac gag atc agc atg ctt ttt ctc acc gac tac atc aag      576
Val Glu Ala His Glu Ile Ser Met Leu Phe Leu Thr Asp Tyr Ile Lys
            180                 185                 190 agt gcc acc ggt ctc agt aat att ttc tcg gac aag aaa gac ggc ggg      624
Ser Ala Thr Gly Leu Ser Asn Ile Phe Ser Asp Lys Lys Asp Gly Gly
        195                 200                 205 cag tat gtg cga tgc aaa aca g gtgcgtgtgg tgtcgtctca ggtgggggac      676
Gln Tyr Val Arg Cys Lys Thr
        210                 215 tcgtttctca gtggtcattc cag gt atg cag tcg att tgc cat gcc atg tca   728
                             Gly Met Gln Ser Ile Cys His Ala Met Ser
                                             220                 225 aag gaa ctt gtt cca ggc tca gtg cac ctc aac acc ccc gtc gct gaa      776
Lys Glu Leu Val Pro Gly Ser Val His Leu Asn Thr Pro Val Ala Glu
                230                 235                 240 att gag cag tcg gca tcc ggc tgt aca gta cga tcg gcc tcg ggc gcc      824
Ile Glu Gln Ser Ala Ser Gly Cys Thr Val Arg Ser Ala Ser Gly Ala
            245                 250                 255 gtg ttc cga agc aaa aag gtg gtg gtt tcg tta ccg aca acc ttg tat      872
Val Phe Arg Ser Lys Lys Val Val Val Ser Leu Pro Thr Thr Leu Tyr
        260                 265                 270 ccc acc ttg aca ttt tca cca cct ctt ccc gcc gag aag caa gca ttg      920
Pro Thr Leu Thr Phe Ser Pro Pro Leu Pro Ala Glu Lys Gln Ala Leu
275                 280                 285 gcg gaa aat tct atc ctg ggc tac tat agc aag ata gtc ttc gta tgg      968
Ala Glu Asn Ser Ile Leu Gly Tyr Tyr Ser Lys Ile Val Phe Val Trp
290                 295                 300                 305 gac aag ccg tgg tgg cgc gaa caa ggc ttc tcg ggc gtc ctc caa tcg     1016
Asp Lys Pro Trp Trp Arg Glu Gln Gly Phe Ser Gly Val Leu Gln Ser
                310                 315                 320 agc tgt gac ccc atc tca ttt gcc aga gat acc agc atc gac gtc gat     1064
Ser Cys Asp Pro Ile Ser Phe Ala Arg Asp Thr Ser Ile Asp Val Asp
            325                 330                 335 cga caa tgg tcc att acc tgt ttc atg gtc gga gac ccg gga cgg aag     1112
Arg Gln Trp Ser Ile Thr Cys Phe Met Val Gly Asp Pro Gly Arg Lys
        340                 345                 350 tgg tcc caa cag tcc aag cag gta cga caa aag tct gtc tgg gac caa     1160
Trp Ser Gln Gln Ser Lys Gln Val Arg Gln Lys Ser Val Trp Asp Gln
355                 360                 365 ctc cgc gca gcc tac gag aac gcc ggg gcc caa gtc cca gag ccg gcc     1208
Leu Arg Ala Ala Tyr Glu Asn Ala Gly Ala Gln Val Pro Glu Pro Ala
```

-continued

```
                370                 375                 380                 385
aac gtg ctc gaa atc gag tgg tcg aag cag cag tat ttc caa gga gct      1256
Asn Val Leu Glu Ile Glu Trp Ser Lys Gln Gln Tyr Phe Gln Gly Ala
                390                 395                 400 ccg agc gcc gtc tat ggg ctg aac gat ctc atc aca ctg ggt tcg gcg      1304
Pro Ser Ala Val Tyr Gly Leu Asn Asp Leu Ile Thr Leu Gly Ser Ala
            405                 410                 415 ctc aga acg ccg ttc aag agt gtt cat ttc gtt gga acg gag acg tct      1352
Leu Arg Thr Pro Phe Lys Ser Val His Phe Val Gly Thr Glu Thr Ser
            420                 425                 430 tta gtt tgg aaa ggg tat atg gaa ggg gcc ata cga tcg ggt caa cga      1400
Leu Val Trp Lys Gly Tyr Met Glu Gly Ala Ile Arg Ser Gly Gln Arg
        435                 440                 445 ggt gct gca gaa gtt gtg gct agc ctg gtg cca gca gca tag              1442
Gly Ala Ala Glu Val Val Ala Ser Leu Val Pro Ala Ala
450                 455                 460
```

<210> SEQ ID NO 8
<211> LENGTH: 462
<212> TYPE: PRT
<213> ORGANISM: Exophiala spinifera

<400> SEQUENCE: 8

```
Asp Asn Val Ala Asp Val Val Val Gly Ala Gly Leu Ser Gly Leu
1               5                   10                  15

Glu Thr Ala Arg Lys Val Gln Ala Ala Gly Leu Ser Cys Leu Val Leu
            20                  25                  30

Glu Ala Met Asp Arg Val Gly Gly Lys Thr Leu Ser Val Gln Ser Gly
        35                  40                  45

Pro Gly Arg Thr Thr Ile Asn Asp Leu Gly Ala Ala Trp Ile Asn Asp
    50                  55                  60

Ser Asn Gln Ser Glu Val Ser Arg Leu Phe Glu Arg Phe His Leu Glu
65                  70                  75                  80

Gly Glu Leu Gln Arg Thr Thr Gly Asn Ser Ile His Gln Ala Gln Asp
                85                  90                  95

Gly Thr Thr Thr Thr Ala Pro Tyr Gly Asp Ser Leu Leu Ser Glu Glu
            100                 105                 110

Val Ala Ser Ala Leu Ala Glu Leu Leu Pro Val Trp Ser Gln Leu Ile
        115                 120                 125

Glu Glu His Ser Leu Gln Asp Leu Lys Ala Ser Pro Gln Ala Lys Arg
    130                 135                 140

Leu Asp Ser Val Ser Phe Ala His Tyr Cys Glu Lys Glu Leu Asn Leu
145                 150                 155                 160

Pro Ala Val Leu Gly Val Ala Asn Gln Ile Thr Arg Ala Leu Leu Gly
                165                 170                 175

Val Glu Ala His Glu Ile Ser Met Leu Phe Leu Thr Asp Tyr Ile Lys
            180                 185                 190

Ser Ala Thr Gly Leu Ser Asn Ile Phe Ser Asp Lys Lys Asp Gly Gly
        195                 200                 205

Gln Tyr Val Arg Cys Lys Thr Gly Met Gln Ser Ile Cys His Ala Met
    210                 215                 220

Ser Lys Glu Leu Val Pro Gly Ser Val His Leu Asn Thr Pro Val Ala
225                 230                 235                 240

Glu Ile Glu Gln Ser Ala Ser Gly Cys Thr Val Arg Ser Ala Ser Gly
                245                 250                 255

Ala Val Phe Arg Ser Lys Lys Val Val Val Ser Leu Pro Thr Thr Leu
```

-continued

```
                260                 265                 270
Tyr Pro Thr Leu Thr Phe Ser Pro Pro Leu Pro Ala Glu Lys Gln Ala
            275                 280                 285

Leu Ala Glu Asn Ser Ile Leu Gly Tyr Tyr Ser Lys Ile Val Phe Val
        290                 295                 300

Trp Asp Lys Pro Trp Trp Arg Glu Gln Gly Phe Ser Gly Val Leu Gln
305                 310                 315                 320

Ser Ser Cys Asp Pro Ile Ser Phe Ala Arg Asp Thr Ser Ile Asp Val
                325                 330                 335

Asp Arg Gln Trp Ser Ile Thr Cys Phe Met Val Gly Asp Pro Gly Arg
            340                 345                 350

Lys Trp Ser Gln Gln Ser Lys Gln Val Arg Gln Lys Ser Val Trp Asp
        355                 360                 365

Gln Leu Arg Ala Ala Tyr Glu Asn Ala Gly Ala Gln Val Pro Glu Pro
    370                 375                 380

Ala Asn Val Leu Glu Ile Glu Trp Ser Lys Gln Gln Tyr Phe Gln Gly
385                 390                 395                 400

Ala Pro Ser Ala Val Tyr Gly Leu Asn Asp Leu Ile Thr Leu Gly Ser
                405                 410                 415

Ala Leu Arg Thr Pro Phe Lys Ser Val His Phe Val Gly Thr Glu Thr
            420                 425                 430

Ser Leu Val Trp Lys Gly Tyr Met Glu Gly Ala Ile Arg Ser Gly Gln
        435                 440                 445

Arg Gly Ala Ala Glu Val Val Ala Ser Leu Val Pro Ala Ala
    450                 455                 460

<210> SEQ ID NO 9
<211> LENGTH: 458
<212> TYPE: PRT
<213> ORGANISM: Exophiala spinifera

<400> SEQUENCE: 9

Asp Asn Val Ala Asp Val Val Val Gly Ala Gly Leu Ser Gly Leu
1               5                   10                  15

Glu Thr Ala Arg Lys Val Gln Ala Ala Gly Leu Ser Cys Leu Val Leu
            20                  25                  30

Glu Ala Met Asp Arg Val Gly Gly Lys Thr Leu Ser Val Gln Ser Gly
        35                  40                  45

Pro Gly Arg Thr Thr Ile Asn Asp Leu Gly Ala Ala Trp Ile Asn Asp
    50                  55                  60

Ser Asn Gln Ser Glu Val Ser Arg Leu Phe Glu Arg Phe His Leu Glu
65                  70                  75                  80

Gly Glu Leu Gln Arg Thr Thr Gly Asn Ser Ile His Gln Ala Gln Asp
                85                  90                  95

Gly Thr Thr Thr Thr Ala Pro Tyr Gly Asp Ser Leu Leu Ser Glu Glu
            100                 105                 110

Val Ala Ser Ala Leu Ala Glu Leu Leu Pro Val Trp Ser Gln Leu Ile
        115                 120                 125

Glu Glu His Ser Leu Gln Asp Leu Lys Ala Ser Pro Gln Ala Lys Arg
    130                 135                 140

Leu Asp Ser Val Ser Phe Ala His Tyr Cys Glu Lys Glu Leu Asn Leu
145                 150                 155                 160

Pro Ala Val Leu Gly Val Ala Asn Gln Ile Thr Arg Ala Leu Leu Gly
                165                 170                 175
```

```
Val Glu Ala His Glu Ile Ser Met Leu Phe Leu Thr Asp Tyr Ile Lys
            180                 185                 190

Ser Ala Thr Gly Leu Ser Asn Ile Phe Ser Asp Lys Lys Asp Gly Gly
            195                 200                 205

Gln Tyr Val Arg Cys Lys Thr Gly Ala Cys Gly Val Val Ser Gly Gly
            210                 215                 220

Gly Leu Val Ser Gln Trp Ser Phe Gln Val Cys Ser Arg Phe Ala Met
225                 230                 235                 240

Pro Cys Gln Arg Asn Leu Phe Gln Ala Gln Cys Thr Ser Thr Pro Pro
                245                 250                 255

Ser Leu Lys Leu Ser Ser Arg His Pro Ala Val Gln Tyr Asp Arg Pro
            260                 265                 270

Arg Ala Pro Cys Ser Glu Ala Lys Arg Trp Trp Phe Arg Tyr Arg Gln
            275                 280                 285

Pro Cys Ile Pro Pro His Phe His His Leu Phe Pro Pro Arg Ser Lys
            290                 295                 300

His Trp Arg Lys Ile Leu Ser Trp Ala Thr Ile Ala Arg Ser Ser Tyr
305                 310                 315                 320

Gly Thr Ser Arg Gly Gly Ala Asn Lys Ala Ser Arg Ala Ser Ser Asn
            325                 330                 335

Arg Ala Val Thr Pro Ser His Leu Pro Glu Ile Pro Ala Ser Thr Ser
            340                 345                 350

Ile Asp Asn Gly Pro Leu Pro Val Ser Trp Ser Glu Thr Arg Asp Gly
            355                 360                 365

Ser Gly Pro Asn Ser Pro Ser Arg Tyr Asp Lys Ser Leu Ser Gly Thr
            370                 375                 380

Asn Ser Ala Gln Pro Thr Arg Thr Pro Gly Pro Lys Ser Gln Ser Arg
385                 390                 395                 400

Pro Thr Cys Ser Lys Ser Ser Gly Arg Ser Ser Ile Ser Lys Glu
                405                 410                 415

Leu Arg Ala Pro Ser Met Gly Thr Ile Ser Ser His Trp Val Arg Arg
            420                 425                 430

Ser Glu Arg Arg Ser Arg Val Phe Ile Ser Leu Glu Arg Arg Arg Leu
            435                 440                 445

Phe Gly Lys Gly Ile Trp Lys Gly Pro Tyr
            450                 455

<210> SEQ ID NO 10
<211> LENGTH: 1392
<212> TYPE: DNA
<213> ORGANISM: Exophiala spinifera
<220> FEATURE:
<221> NAME/KEY: CDS
<222> LOCATION: (1)...(1389)
<221> NAME/KEY: misc_feature
<222> LOCATION: (1)...(3)
<223> OTHER INFORMATION: Extra lysine in K:trAPAO

<400> SEQUENCE: 10 aaa gac aac gtt gcg gac gtg gta gtg gtg ggc gct ggc ttg agc ggt      48
Lys Asp Asn Val Ala Asp Val Val Val Val Gly Ala Gly Leu Ser Gly
1               5                   10                  15 ttg gag acg gca cgc aaa gtc cag gcc gcc ggt ctg tcc tgc ctc gtt      96
Leu Glu Thr Ala Arg Lys Val Gln Ala Ala Gly Leu Ser Cys Leu Val
            20                  25                  30 ctt gag gcg atg gat cgt gta ggg gga aag act ctg agc gta caa tcg     144
Leu Glu Ala Met Asp Arg Val Gly Gly Lys Thr Leu Ser Val Gln Ser
        35                  40                  45
```

```
ggt ccc ggc agg acg act atc aac gac ctc ggc gct gcg tgg atc aat        192
Gly Pro Gly Arg Thr Thr Ile Asn Asp Leu Gly Ala Ala Trp Ile Asn
 50                  55                  60 gac agc aac caa agc gaa gta tcc aga ttg ttt gaa aga ttt cat ttg        240
Asp Ser Asn Gln Ser Glu Val Ser Arg Leu Phe Glu Arg Phe His Leu
 65                  70                  75                  80 gag ggc gag ctc cag agg acg act gga aat tca atc cat caa gca caa        288
Glu Gly Glu Leu Gln Arg Thr Thr Gly Asn Ser Ile His Gln Ala Gln
                 85                  90                  95 gac ggt aca acc act aca gct cct tat ggt gac tcc ttg ctg agc gag        336
Asp Gly Thr Thr Thr Thr Ala Pro Tyr Gly Asp Ser Leu Leu Ser Glu
            100                 105                 110 gag gtt gca agt gca ctt gcg gaa ctc ctc ccc gta tgg tct cag ctg        384
Glu Val Ala Ser Ala Leu Ala Glu Leu Leu Pro Val Trp Ser Gln Leu
        115                 120                 125 atc gaa gag cat agc ctt caa gac ctc aag gcg agc cct cag gcg aag        432
Ile Glu Glu His Ser Leu Gln Asp Leu Lys Ala Ser Pro Gln Ala Lys
    130                 135                 140 cgg ctc gac agt gtg agc ttc gcg cac tac tgt gag aag gaa cta aac        480
Arg Leu Asp Ser Val Ser Phe Ala His Tyr Cys Glu Lys Glu Leu Asn
145                 150                 155                 160 ttg cct gct gtt ctc ggc gta gca aac cag atc aca cgc gct ctg ctc        528
Leu Pro Ala Val Leu Gly Val Ala Asn Gln Ile Thr Arg Ala Leu Leu
                165                 170                 175 ggt gtg gaa gcc cac gag atc agc atg ctt ttt ctc acc gac tac atc        576
Gly Val Glu Ala His Glu Ile Ser Met Leu Phe Leu Thr Asp Tyr Ile
            180                 185                 190 aag agt gcc acc ggt ctc agt aat att ttc tcg gac aag aaa gac ggc        624
Lys Ser Ala Thr Gly Leu Ser Asn Ile Phe Ser Asp Lys Lys Asp Gly
        195                 200                 205 ggg cag tat atg cga tgc aaa aca ggt atg cag tcg att tgc cat gcc        672
Gly Gln Tyr Met Arg Cys Lys Thr Gly Met Gln Ser Ile Cys His Ala
    210                 215                 220 atg tca aag gaa ctt gtt cca ggc tca gtg cac ctc aac acc ccc gtc        720
Met Ser Lys Glu Leu Val Pro Gly Ser Val His Leu Asn Thr Pro Val
225                 230                 235                 240 gct gaa att gag cag tcg gca tcc ggc tgt aca gta cga tcg gcc tcg        768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc        816
Gly Ala Val Phe Arg Ser Lys Lys Val Val Val Ser Leu Pro Thr Thr
            260                 265                 270 ttg tat ccc acc ttg aca ttt tca cca cct ctt ccc gcc gag aag caa        864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc        912
Ala Leu Ala Glu Asn Ser Ile Leu Gly Tyr Tyr Ser Lys Ile Val Phe
    290                 295                 300 gta tgg gac aag ccg tgg tgg cgc gaa caa ggc ttc tcg ggc gtc ctc        960
Val Trp Asp Lys Pro Trp Trp Arg Glu Gln Gly Phe Ser Gly Val Leu
305                 310                 315                 320 caa tcg agc tgt gac ccc atc tca ttt gcc aga gat acc agc atc gac       1008
Gln Ser Ser Cys Asp Pro Ile Ser Phe Ala Arg Asp Thr Ser Ile Asp
                325                 330                 335 gtc gat cga caa tgg tcc att acc tgt ttc atg gtc gga gac ccg gga       1056
Val Asp Arg Gln Trp Ser Ile Thr Cys Phe Met Val Gly Asp Pro Gly
            340                 345                 350 cgg aag tgg tcc caa cag tcc aag cag gta cga caa aag tct gtc tgg       1104
Arg Lys Trp Ser Gln Gln Ser Lys Gln Val Arg Gln Lys Ser Val Trp
```

-continued

```
gac caa ctc cgc gca gcc tac gag aac gcc ggg gcc caa gtc cca gag      1152
Asp Gln Leu Arg Ala Ala Tyr Glu Asn Ala Gly Ala Gln Val Pro Glu
        370                 375                 380 ccg gcc aac gtg ctc gaa atc gag tgg tcg aag cag cag tat ttc caa      1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt      1248
Gly Ala Pro Ser Ala Val Tyr Gly Leu Asn Asp Leu Ile Thr Leu Gly
                405                 410                 415 tcg gcg ctc aga acg ccg ttc aag agt gtt cat ttc gtt gga acg gag      1296
Ser Ala Leu Arg Thr Pro Phe Lys Ser Val His Phe Val Gly Thr Glu
            420                 425                 430 acg tct tta gtt tgg aaa ggg tat atg gaa ggg gcc ata cga tcg ggt      1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca          1389
Gln Arg Gly Ala Ala Glu Val Val Ala Ser Leu Val Pro Ala Ala
450                 455                 460 tag                                                                   1392
```

<210> SEQ ID NO 11
<211> LENGTH: 463
<212> TYPE: PRT
<213> ORGANISM: Exophiala spinifera
<220> FEATURE:
<223> OTHER INFORMATION: Extra lysine in the polypeptide sequence of
      K:trAPAO, 463 aa.

<400> SEQUENCE: 11

```
Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
        35                  40                  45

Gly Pro Gly Arg Thr Thr Ile Asn Asp Leu Gly Ala Ala Trp Ile Asn
50                  55                  60

Asp Ser Asn Gln Ser Glu Val Ser Arg Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Thr Thr Thr Ala Pro Tyr Gly Asp Ser Leu Leu Ser Glu
            100                 105                 110

Glu Val Ala Ser Ala Leu Ala Glu Leu Leu Pro Val Trp Ser Gln Leu
        115                 120                 125

Ile Glu Glu His Ser Leu Gln Asp Leu Lys Ala Ser Pro Gln Ala Lys
    130                 135                 140

Arg Leu Asp Ser Val Ser Phe Ala His Tyr Cys Glu Lys Glu Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Ile Ser Met Leu Phe Leu Thr Asp Tyr Ile
            180                 185                 190

Lys Ser Ala Thr Gly Leu Ser Asn Ile Phe Ser Asp Lys Lys Asp Gly
        195                 200                 205

Gly Gln Tyr Met Arg Cys Lys Thr Gly Met Gln Ser Ile Cys His Ala
```

-continued

```
            210                 215                 220
Met Ser Lys Glu Leu Val Pro Gly Ser Val His Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
                260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
290                 295                 300

Val Trp Asp Lys Pro Trp Trp Arg Glu Gln Gly Phe Ser Gly Val Leu
305                 310                 315                 320

Gln Ser Ser Cys Asp Pro Ile Ser Phe Ala Arg Asp Thr Ser Ile Asp
                325                 330                 335

Val Asp Arg Gln Trp Ser Ile Thr Cys Phe Met Val Gly Asp Pro Gly
                340                 345                 350

Arg Lys Trp Ser Gln Gln Ser Lys Gln Val Arg Gln Lys Ser Val Trp
            355                 360                 365

Asp Gln Leu Arg Ala Ala Tyr Glu Asn Ala Gly Ala Gln Val Pro Glu
370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Ser Val His Phe Val Gly Thr Glu
                420                 425                 430

Thr Ser Leu Val Trp Lys Gly Tyr Met Glu Gly Ala Ile Arg Ser Gly
            435                 440                 445

Gln Arg Gly Ala Ala Glu Val Val Ala Ser Leu Val Pro Ala Ala
            450                 455                 460

<210> SEQ ID NO 12
<211> LENGTH: 34
<212> TYPE: DNA
<213> ORGANISM: Artificial Sequence
<220> FEATURE:
<223> OTHER INFORMATION: Primer sequence designed for cloning DNA into
      expression vectors, N23256

<400> SEQUENCE: 12
ggggaattca aagacaacgt tgcggacgtg gtag                              34

<210> SEQ ID NO 13
<211> LENGTH: 34
<212> TYPE: DNA
<213> ORGANISM: Artificial Sequence
<220> FEATURE:
<223> OTHER INFORMATION: Primer sequence designed for cloning DNA into
      expression vectors, N23259

<400> SEQUENCE: 13
ggggcggccg cctatgctgc tggcaccagg ctag                              34

<210> SEQ ID NO 14
<211> LENGTH: 29
<212> TYPE: DNA
<213> ORGANISM: Artificial Sequence
<220> FEATURE:
```

<223> OTHER INFORMATION: Designed oligonucleotide for 3' RACE, N21965

<400> SEQUENCE: 14
tggtttcgtt accgacaacc ttgtatccc                              29

<210> SEQ ID NO 15
<211> LENGTH: 28
<212> TYPE: DNA
<213> ORGANISM: Artificial Sequence
<220> FEATURE:
<223> OTHER INFORMATION: Designed oligonucleotide for 5' race, N21968

<400> SEQUENCE: 15
gagttggtcc cagacagact tttgtcgt                               28

<210> SEQ ID NO 16
<211> LENGTH: 1673
<212> TYPE: DNA
<213> ORGANISM: Exophiala spinifera
<220> FEATURE:
<221> NAME/KEY: sig_peptide
<222> LOCATION: (1)...(267)
<223> OTHER INFORMATION: yeast alpha mating factor secretion signal.
<220> FEATURE:
<221> NAME/KEY: CDS
<222> LOCATION: (1)...(1662)

<400> SEQUENCE: 16

```
atg aga ttt cct tca att ttt act gct gtt tta ttc gca gca tcc tcc      48
Met Arg Phe Pro Ser Ile Phe Thr Ala Val Leu Phe Ala Ala Ser Ser
            -85                 -80                 -75 gca tta gct gct cca gtc aac act aca aca gaa gat gaa acg gca caa      96
Ala Leu Ala Ala Pro Val Asn Thr Thr Thr Glu Asp Glu Thr Ala Gln
        -70                 -65                 -60 att ccg gct gaa gct gtc atc ggt tac tca gat tta gaa ggg gat ttc     144
Ile Pro Ala Glu Ala Val Ile Gly Tyr Ser Asp Leu Glu Gly Asp Phe
    -55                 -50                 -45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu
  -40                 -35                 -30 ttt ata aat act act att gcc agc att gct gct aaa gaa gaa ggg gta     240
Phe Ile Asn Thr Thr Ile Ala Ser Ile Ala Ala Lys Glu Glu Gly Val
-25                 -20                 -15                 -10 tct ctc gag aaa aga gag gct gaa gct gaa ttc aaa gac aac gtt gcg     288
Ser Leu Glu Lys Arg Glu Ala Glu Ala Glu Phe Lys Asp Asn Val Ala
                -5                  1                   5 gac gtg gta gtg gtg ggc gct ggc ttg agc ggt ttg gag acg gca cgc     336
Asp Val Val Val Val Gly Ala Gly Leu Ser Gly Leu Glu Thr Ala Arg
            10                  15                  20 aaa gtc cag gcc gcc ggt ctg tcc tgc ctc gtt ctt gag gcg atg gat     384
Lys Val Gln Ala Ala Gly Leu Ser Cys Leu Val Leu Glu Ala Met Asp
        25                  30                  35 cgt gta ggg gga aag act ctg agc gta caa tcg ggt ccc ggc agg acg     432
Arg Val Gly Gly Lys Thr Leu Ser Val Gln Ser Gly Pro Gly Arg Thr
    40                  45                  50                  55 act atc aac gac ctc ggc gct gcg tgg atc aat gac agc aac caa agc     480
Thr Ile Asn Asp Leu Gly Ala Ala Trp Ile Asn Asp Ser Asn Gln Ser
                60                  65                  70 gaa gta tcc aga ttg ttt gaa aga ttt cat ttg gag ggc gag ctc cag     528
Glu Val Ser Arg Leu Phe Glu Arg Phe His Leu Glu Gly Glu Leu Gln
            75                  80                  85 agg acg act gga aat tca atc cat caa gca caa gac ggt aca acc act     576
Arg Thr Thr Gly Asn Ser Ile His Gln Ala Gln Asp Gly Thr Thr Thr
```

```
                90                    95                    100
aca gct cct tat ggt gac tcc ttg ctg agc gag gag gtt gca agt gca    624
Thr Ala Pro Tyr Gly Asp Ser Leu Leu Ser Glu Glu Val Ala Ser Ala
    105                 110                 115 ctt gcg gaa ctc ctc ccc gta tgg tct cag ctg atc gaa gag cat agc    672
Leu Ala Glu Leu Leu Pro Val Trp Ser Gln Leu Ile Glu Glu His Ser
120                 125                 130                 135 ctt caa gac ctc aag gcg agc cct cag gcg aag cgg ctc gac agt gtg    720
Leu Gln Asp Leu Lys Ala Ser Pro Gln Ala Lys Arg Leu Asp Ser Val
                140                 145                 150 agc ttc gcg cac tac tgt gag aag gaa cta aac ttg cct gct gtt ctc    768
Ser Phe Ala His Tyr Cys Glu Lys Glu Leu Asn Leu Pro Ala Val Leu
            155                 160                 165 ggc gta gca aac cag atc aca cgc gct ctg ctc ggt gtg gaa gcc cac    816
Gly Val Ala Asn Gln Ile Thr Arg Ala Leu Leu Gly Val Glu Ala His
        170                 175                 180 gag atc agc atg ctt ttt ctc acc gac tac atc aag agt gcc acc ggt    864
Glu Ile Ser Met Leu Phe Leu Thr Asp Tyr Ile Lys Ser Ala Thr Gly
    185                 190                 195 ctc agt aat att ttc tcg gac aag aaa gac ggc ggg cag tat atg cga    912
Leu Ser Asn Ile Phe Ser Asp Lys Lys Asp Gly Gly Gln Tyr Met Arg
200                 205                 210                 215 tgc aaa aca ggt atg cag tcg att tgc cat gcc atg tca aag gaa ctt    960
Cys Lys Thr Gly Met Gln Ser Ile Cys His Ala Met Ser Lys Glu Leu
                220                 225                 230 gtt cca ggc tca gtg cac ctc aac acc ccc gtc gct gaa att gag cag   1008
Val Pro Gly Ser Val His Leu Asn Thr Pro Val Ala Glu Ile Glu Gln
            235                 240                 245 tcg gca tcc ggc tgt aca gta cga tcg gcc tcg ggc gcc gtg ttc cga   1056
Ser Ala Ser Gly Cys Thr Val Arg Ser Ala Ser Gly Ala Val Phe Arg
        250                 255                 260 agc aaa aag gtg gtg gtt tcg tta ccg aca acc ttg tat ccc acc ttg   1104
Ser Lys Lys Val Val Val Ser Leu Pro Thr Thr Leu Tyr Pro Thr Leu
    265                 270                 275 aca ttt tca cca cct ctt ccc gcc gag aag caa gca ttg gcg gaa aat   1152
Thr Phe Ser Pro Pro Leu Pro Ala Glu Lys Gln Ala Leu Ala Glu Asn
280                 285                 290                 295 tct atc ctg ggc tac tat agc aag ata gtc ttc gta tgg gac aag ccg   1200
Ser Ile Leu Gly Tyr Tyr Ser Lys Ile Val Phe Val Trp Asp Lys Pro
                300                 305                 310 tgg tgg cgc gaa caa ggc ttc tcg ggc gtc ctc caa tcg agc tgt gac   1248
Trp Trp Arg Glu Gln Gly Phe Ser Gly Val Leu Gln Ser Ser Cys Asp
            315                 320                 325 ccc atc tca ttt gcc aga gat acc agc atc gac gtc gat cga caa tgg   1296
Pro Ile Ser Phe Ala Arg Asp Thr Ser Ile Asp Val Asp Arg Gln Trp
        330                 335                 340 tcc att acc tgt ttc atg gtc gga gac ccg gga cgg aag tgg tcc caa   1344
Ser Ile Thr Cys Phe Met Val Gly Asp Pro Gly Arg Lys Trp Ser Gln
    345                 350                 355 cag tcc aag cag gta cga caa aag tct gtc tgg gac caa ctc cgc gca   1392
Gln Ser Lys Gln Val Arg Gln Lys Ser Val Trp Asp Gln Leu Arg Ala
360                 365                 370                 375 gcc tac gag aac gcc ggg gcc caa gtc cca gag ccg gcc aac gtg ctc   1440
Ala Tyr Glu Asn Ala Gly Ala Gln Val Pro Glu Pro Ala Asn Val Leu
                380                 385                 390 gaa atc gag tgg tcg aag cag cag tat ttc caa gga gct ccg agc gcc   1488
Glu Ile Glu Trp Ser Lys Gln Gln Tyr Phe Gln Gly Ala Pro Ser Ala
            395                 400                 405 gtc tat ggg ctg aac gat ctc atc aca ctg ggt tcg gcg ctc aga acg   1536
Val Tyr Gly Leu Asn Asp Leu Ile Thr Leu Gly Ser Ala Leu Arg Thr
```

```
Val Tyr Gly Leu Asn Asp Leu Ile Thr Leu Gly Ser Ala Leu Arg Thr
        410                 415                 420 ccg ttc aag agt gtt cat ttc gtt gga acg gag acg tct tta gtt tgg    1584
Pro Phe Lys Ser Val His Phe Val Gly Thr Glu Thr Ser Leu Val Trp
425                 430                 435 aaa ggg tat atg gaa ggg gcc ata cga tcg ggt caa cga ggt gct gca    1632
Lys Gly Tyr Met Glu Gly Ala Ile Arg Ser Gly Gln Arg Gly Ala Ala
440                 445                 450                 455 gaa gtt gtg gct agc ctg gtg cca gca gca taggcggccg c               1673
Glu Val Val Ala Ser Leu Val Pro Ala Ala
                460             465
```

<210> SEQ ID NO 17
<211> LENGTH: 554
<212> TYPE: PRT
<213> ORGANISM: Exophiala spinifera
<220> FEATURE:
<221> NAME/KEY: SIGNAL
<222> LOCATION: (1)...(89)
<223> OTHER INFORMATION: yeast alpha mating factor secretion signal.

<400> SEQUENCE: 17

```
Met Arg Phe Pro Ser Ile Phe Thr Ala Val Leu Phe Ala Ala Ser Ser
                -85                 -80                 -75

Ala Leu Ala Ala Pro Val Asn Thr Thr Thr Glu Asp Glu Thr Ala Gln
            -70                 -65                 -60

Ile Pro Ala Glu Ala Val Ile Gly Tyr Ser Asp Leu Glu Gly Asp Phe
        -55                 -50                 -45

Asp Val Ala Val Leu Pro Phe Ser Asn Ser Thr Asn Asn Gly Leu Leu
    -40                 -35                 -30

Phe Ile Asn Thr Thr Ile Ala Ser Ile Ala Ala Lys Glu Glu Gly Val
-25                 -20                 -15                 -10

Ser Leu Glu Lys Arg Glu Ala Glu Ala Glu Phe Lys Asp Asn Val Ala
                -5                  1                   5

Asp Val Val Val Gly Ala Gly Leu Ser Gly Leu Glu Thr Ala Arg
                10                  15                  20

Lys Val Gln Ala Ala Gly Leu Ser Cys Leu Val Leu Glu Ala Met Asp
25                  30                  35

Arg Val Gly Gly Lys Thr Leu Ser Val Gln Ser Gly Pro Gly Arg Thr
40                  45                  50                  55

Thr Ile Asn Asp Leu Gly Ala Ala Trp Ile Asn Asp Ser Asn Gln Ser
                60                  65                  70

Glu Val Ser Arg Leu Phe Glu Arg Phe His Leu Glu Gly Glu Leu Gln
                75                  80                  85

Arg Thr Thr Gly Asn Ser Ile His Gln Ala Gln Asp Gly Thr Thr Thr
                90                  95                  100

Thr Ala Pro Tyr Gly Asp Ser Leu Leu Ser Glu Val Ala Ser Ala
        105                 110                 115

Leu Ala Glu Leu Leu Pro Val Trp Ser Gln Leu Ile Glu Glu His Ser
120                 125                 130                 135

Leu Gln Asp Leu Lys Ala Ser Pro Gln Ala Lys Arg Leu Asp Ser Val
                140                 145                 150

Ser Phe Ala His Tyr Cys Glu Lys Glu Leu Asn Leu Pro Ala Val Leu
            155                 160                 165

Gly Val Ala Asn Gln Ile Thr Arg Ala Leu Leu Gly Val Glu Ala His
        170                 175                 180

Glu Ile Ser Met Leu Phe Leu Thr Asp Tyr Ile Lys Ser Ala Thr Gly
```

```
            185                 190                 195
Leu Ser Asn Ile Phe Ser Asp Lys Asp Gly Gln Tyr Met Arg
200                 205                 210                 215

Cys Lys Thr Gly Met Gln Ser Ile Cys His Ala Met Ser Lys Glu Leu
                220                 225                 230

Val Pro Gly Ser Val His Leu Asn Thr Pro Val Ala Glu Ile Glu Gln
                235                 240                 245

Ser Ala Ser Gly Cys Thr Val Arg Ser Ala Ser Gly Ala Val Phe Arg
                250                 255                 260

Ser Lys Lys Val Val Val Ser Leu Pro Thr Thr Leu Tyr Pro Thr Leu
265                 270                 275

Thr Phe Ser Pro Pro Leu Pro Ala Glu Lys Gln Ala Leu Ala Glu Asn
280                 285                 290                 295

Ser Ile Leu Gly Tyr Tyr Ser Lys Ile Val Phe Val Trp Asp Lys Pro
                300                 305                 310

Trp Trp Arg Glu Gln Gly Phe Ser Gly Val Leu Gln Ser Ser Cys Asp
                315                 320                 325

Pro Ile Ser Phe Ala Arg Asp Thr Ser Ile Asp Val Asp Arg Gln Trp
                330                 335                 340

Ser Ile Thr Cys Phe Met Val Gly Asp Pro Gly Arg Lys Trp Ser Gln
345                 350                 355

Gln Ser Lys Gln Val Arg Gln Lys Ser Val Trp Asp Gln Leu Arg Ala
360                 365                 370                 375

Ala Tyr Glu Asn Ala Gly Ala Gln Val Pro Glu Pro Ala Asn Val Leu
                380                 385                 390

Glu Ile Glu Trp Ser Lys Gln Gln Tyr Phe Gln Gly Ala Pro Ser Ala
                395                 400                 405

Val Tyr Gly Leu Asn Asp Leu Ile Thr Leu Gly Ser Ala Leu Arg Thr
                410                 415                 420

Pro Phe Lys Ser Val His Phe Val Gly Thr Glu Thr Ser Leu Val Trp
                425                 430                 435

Lys Gly Tyr Met Glu Gly Ala Ile Arg Ser Gly Gln Arg Gly Ala Ala
440                 445                 450                 455

Glu Val Val Ala Ser Leu Val Pro Ala Ala
                460                 465

<210> SEQ ID NO 18
<211> LENGTH: 2079
<212> TYPE: DNA
<213> ORGANISM: Unknown
<220> FEATURE:
<221> NAME/KEY: CDS
<222> LOCATION: (1)...(2076)
<223> OTHER INFORMATION: GST:K:trAPAO 2079 nt. Translation starting at
      nt 1 - 687, gst fusion + polylinker; 688-2076, K:trAPAO;
      2077-2079, stop codon. For bacterial expression.
<220> FEATURE:
<221> NAME/KEY: misc_feature
<222> LOCATION: (1)...(687)
<223> OTHER INFORMATION: gst fusion + polylinker
<220> FEATURE:
<221> NAME/KEY: misc_feature
<222> LOCATION: (688)...(2076)
<223> OTHER INFORMATION: K:trAPAO
<220> FEATURE:
<221> NAME/KEY: misc_feature
<222> LOCATION: (688)...(690)
<223> OTHER INFORMATION: Extra lysine

<400> SEQUENCE: 18
```

```
atg tcc cct ata cta ggt tat tgg aaa att aag ggc ctt gtc caa ccc    48
Met Ser Pro Ile Leu Gly Tyr Trp Lys Ile Lys Gly Leu Val Gln Pro
 1               5                  10                  15 act cga ctt ctt ttg gaa tat ctt gaa gaa aaa tat gaa gag cat ttg    96
Thr Arg Leu Leu Leu Glu Tyr Leu Glu Glu Lys Tyr Glu Glu His Leu
                20                  25                  30 tat gag cgc gat gaa ggt gat aaa tgg cga aac aaa aag ttt gaa ttg   144
Tyr Glu Arg Asp Glu Gly Asp Lys Trp Arg Asn Lys Lys Phe Glu Leu
            35                  40                  45 ggt ttg gag ttt ccc aat ctt cct tat tat att gat ggt gat gtt aaa   192
Gly Leu Glu Phe Pro Asn Leu Pro Tyr Tyr Ile Asp Gly Asp Val Lys
        50                  55                  60 tta aca cag tct atg gcc atc ata cgt tat ata gct gac aag cac aac   240
Leu Thr Gln Ser Met Ala Ile Ile Arg Tyr Ile Ala Asp Lys His Asn
 65                 70                  75                  80 atg ttg ggt ggt tgt cca aaa gag cgt gca gag att tca atg ctt gaa   288
Met Leu Gly Gly Cys Pro Lys Glu Arg Ala Glu Ile Ser Met Leu Glu
                85                  90                  95 gga gcg gtt ttg gat att aga tac ggt gtt tcg aga att gca tat agt   336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa   384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat   432
Met Leu Lys Met Phe Glu Asp Arg Leu Cys His Lys Thr Tyr Leu Asn
130                 135                 140 ggt gat cat gta acc cat cct gac ttc atg ttg tat gac gct ctt gat   480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta   528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac   576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc   624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ctg gtt ccg cgt   672
Thr Phe Gly Gly Gly Asp His Pro Pro Lys Ser Asp Leu Val Pro Arg
210                 215                 220 gga tcc ccg gaa ttc aaa gac aac gtt gcg gac gtg gta gtg gtg ggc   720
Gly Ser Pro Glu Phe Lys Asp Asn Val Ala Asp Val Val Val Val Gly
225                 230                 235                 240 gct ggc ttg agc ggt ttg gag acg gca cgc aaa gtc cag gcc gcc ggt   768
Ala Gly Leu Ser Gly Leu Glu Thr Ala Arg Lys Val Gln Ala Ala Gly
                245                 250                 255 ctg tcc tgc ctc gtt ctt gag gcg atg gat cgt gta ggg gga aag act   816
Leu Ser Cys Leu Val Leu Glu Ala Met Asp Arg Val Gly Gly Lys Thr
            260                 265                 270 ctg agc gta caa tcg ggt ccc ggc agg acg act atc aac gac ctc ggc   864
Leu Ser Val Gln Ser Gly Pro Gly Arg Thr Thr Ile Asn Asp Leu Gly
        275                 280                 285 gct gcg tgg atc aat gac agc aac caa agc gaa gta tcc aga ttg ttt   912
Ala Ala Trp Ile Asn Asp Ser Asn Gln Ser Glu Val Ser Arg Leu Phe
290                 295                 300 gaa aga ttt cat ttg gag ggc gag ctc cag agg acg act gga aat tca   960
Glu Arg Phe His Leu Glu Gly Glu Leu Gln Arg Thr Thr Gly Asn Ser
305                 310                 315                 320
```

```
atc cat caa gca caa gac ggt aca acc act aca gct cct tat ggt gac    1008
Ile His Gln Ala Gln Asp Gly Thr Thr Thr Thr Ala Pro Tyr Gly Asp
            325                 330                 335 tcc ttg ctg agc gag gag gtt gca agt gca ctt gcg gaa ctc ctc ccc    1056
Ser Leu Leu Ser Glu Glu Val Ala Ser Ala Leu Ala Glu Leu Leu Pro
        340                 345                 350 gta tgg tct cag ctg atc gaa gag cat agc ctt caa gac ctc aag gcg    1104
Val Trp Ser Gln Leu Ile Glu Glu His Ser Leu Gln Asp Leu Lys Ala
    355                 360                 365 agc cct cag gcg aag cgg ctc gac agt gtg agc ttc gcg cac tac tgt    1152
Ser Pro Gln Ala Lys Arg Leu Asp Ser Val Ser Phe Ala His Tyr Cys
370                 375                 380 gag aag gaa cta aac ttg cct gct gtt ctc ggc gta gca aac cag atc    1200
Glu Lys Glu Leu Asn Leu Pro Ala Val Leu Gly Val Ala Asn Gln Ile
385                 390                 395                 400 aca cgc gct ctg ctc ggt gtg gaa gcc cac gag atc agc atg ctt ttt    1248
Thr Arg Ala Leu Leu Gly Val Glu Ala His Glu Ile Ser Met Leu Phe
            405                 410                 415 ctc acc gac tac atc aag agt gcc acc ggt ctc agt aat att ttc tcg    1296
Leu Thr Asp Tyr Ile Lys Ser Ala Thr Gly Leu Ser Asn Ile Phe Ser
        420                 425                 430 gac aag aaa gac ggc ggg cag tat atg cga tgc aaa aca ggt atg cag    1344
Asp Lys Lys Asp Gly Gly Gln Tyr Met Arg Cys Lys Thr Gly Met Gln
    435                 440                 445 tcg att tgc cat gcc atg tca aag gaa ctt gtt cca ggc tca gtg cac    1392
Ser Ile Cys His Ala Met Ser Lys Glu Leu Val Pro Gly Ser Val His
450                 455                 460 ctc aac acc ccc gtc gct gaa att gag cag tcg gca tcc ggc tgt aca    1440
Leu Asn Thr Pro Val Ala Glu Ile Glu Gln Ser Ala Ser Gly Cys Thr
465                 470                 475                 480 gta cga tcg gcc tcg ggc gcc gtg ttc cga agc aaa aag gtg gtg gtt    1488
Val Arg Ser Ala Ser Gly Ala Val Phe Arg Ser Lys Lys Val Val Val
            485                 490                 495 tcg tta ccg aca acc ttg tat ccc acc ttg aca ttt tca cca cct ctt    1536
Ser Leu Pro Thr Thr Leu Tyr Pro Thr Leu Thr Phe Ser Pro Pro Leu
        500                 505                 510 ccc gcc gag aag caa gca ttg gcg gaa aat tct atc ctg ggc tac tat    1584
Pro Ala Glu Lys Gln Ala Leu Ala Glu Asn Ser Ile Leu Gly Tyr Tyr
    515                 520                 525 agc aag ata gtc ttc gta tgg gac aag ccg tgg tgg cgc gaa caa ggc    1632
Ser Lys Ile Val Phe Val Trp Asp Lys Pro Trp Trp Arg Glu Gln Gly
530                 535                 540 ttc tcg ggc gtc ctc caa tcg agc tgt gac ccc atc tca ttt gcc aga    1680
Phe Ser Gly Val Leu Gln Ser Ser Cys Asp Pro Ile Ser Phe Ala Arg
545                 550                 555                 560 gat acc agc atc gac gtc gat cga caa tgg tcc att acc tgt ttc atg    1728
Asp Thr Ser Ile Asp Val Asp Arg Gln Trp Ser Ile Thr Cys Phe Met
            565                 570                 575 gtc gga gac ccg gga cgg aag tgg tcc caa cag tcc aag cag gta cga    1776
Val Gly Asp Pro Gly Arg Lys Trp Ser Gln Gln Ser Lys Gln Val Arg
        580                 585                 590 caa aag tct gtc tgg gac caa ctc cgc gca gcc tac gag aac gcc ggg    1824
Gln Lys Ser Val Trp Asp Gln Leu Arg Ala Ala Tyr Glu Asn Ala Gly
    595                 600                 605 gcc caa gtc cca gag ccg gcc aac gtg ctc gaa atc gag tgg tcg aag    1872
Ala Gln Val Pro Glu Pro Ala Asn Val Leu Glu Ile Glu Trp Ser Lys
610                 615                 620 cag cag tat ttc caa gga gct ccg agc gcc gtc tat ggg ctg aac gat    1920
Gln Gln Tyr Phe Gln Gly Ala Pro Ser Ala Val Tyr Gly Leu Asn Asp
```

```
                      625                   630                   635                    640
ctc atc aca ctg ggt tcg gcg ctc aga acg ccg ttc aag agt gtt cat       1968
Leu Ile Thr Leu Gly Ser Ala Leu Arg Thr Pro Phe Lys Ser Val His
                645                   650                   655 ttc gtt gga acg gag acg tct tta gtt tgg aaa ggg tat atg gaa ggg       2016
Phe Val Gly Thr Glu Thr Ser Leu Val Trp Lys Gly Tyr Met Glu Gly
                660                   665                   670 gcc ata cga tcg ggt caa cga ggt gct gca gaa gtt gtg gct agc ctg       2064
Ala Ile Arg Ser Gly Gln Arg Gly Ala Ala Glu Val Val Ala Ser Leu
                675                   680                   685 gtg cca gca gca tag                                                    2079
Val Pro Ala Ala
        690

<210> SEQ ID NO 19
<211> LENGTH: 692
<212> TYPE: PRT
<213> ORGANISM: Unknown
<220> FEATURE:
<223> OTHER INFORMATION: GST:K:trAPAO; GST + linker, aa 1-229; K:trAPAO,
      aa 230-692

<400> SEQUENCE: 19
```

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Glu Phe Lys Asp Asn Val Ala Asp Val Val Val Gly
225                 230                 235                 240

Ala Gly Leu Ser Gly Leu Glu Thr Ala Arg Lys Val Gln Ala Ala Gly
                245                 250                 255

Leu Ser Cys Leu Val Leu Glu Ala Met Asp Arg Val Gly Gly Lys Thr
            260                 265                 270

```
Leu Ser Val Gln Ser Gly Pro Gly Arg Thr Thr Ile Asn Asp Leu Gly
            275                 280                 285

Ala Ala Trp Ile Asn Asp Ser Asn Gln Ser Glu Val Ser Arg Leu Phe
        290                 295                 300

Glu Arg Phe His Leu Glu Gly Glu Leu Gln Arg Thr Thr Gly Asn Ser
305                 310                 315                 320

Ile His Gln Ala Gln Asp Gly Thr Thr Thr Ala Pro Tyr Gly Asp
                325                 330                 335

Ser Leu Leu Ser Glu Glu Val Ala Ser Ala Leu Ala Glu Leu Leu Pro
            340                 345                 350

Val Trp Ser Gln Leu Ile Glu Glu His Ser Leu Gln Asp Leu Lys Ala
            355                 360                 365

Ser Pro Gln Ala Lys Arg Leu Asp Ser Val Ser Phe Ala His Tyr Cys
        370                 375                 380

Glu Lys Glu Leu Asn Leu Pro Ala Val Leu Gly Val Ala Asn Gln Ile
385                 390                 395                 400

Thr Arg Ala Leu Leu Gly Val Glu Ala His Glu Ile Ser Met Leu Phe
                405                 410                 415

Leu Thr Asp Tyr Ile Lys Ser Ala Thr Gly Leu Ser Asn Ile Phe Ser
            420                 425                 430

Asp Lys Lys Asp Gly Gly Gln Tyr Met Arg Cys Lys Thr Gly Met Gln
            435                 440                 445

Ser Ile Cys His Ala Met Ser Lys Glu Leu Val Pro Gly Ser Val His
        450                 455                 460

Leu Asn Thr Pro Val Ala Glu Ile Glu Gln Ser Ala Ser Gly Cys Thr
465                 470                 475                 480

Val Arg Ser Ala Ser Gly Ala Val Phe Arg Ser Lys Val Val Val
                485                 490                 495

Ser Leu Pro Thr Thr Leu Tyr Pro Thr Leu Thr Phe Ser Pro Pro Leu
            500                 505                 510

Pro Ala Glu Lys Gln Ala Leu Ala Glu Asn Ser Ile Leu Gly Tyr Tyr
        515                 520                 525

Ser Lys Ile Val Phe Val Trp Asp Lys Pro Trp Trp Arg Glu Gln Gly
        530                 535                 540

Phe Ser Gly Val Leu Gln Ser Ser Cys Asp Pro Ile Ser Phe Ala Arg
545                 550                 555                 560

Asp Thr Ser Ile Asp Val Asp Arg Gln Trp Ser Ile Thr Cys Phe Met
                565                 570                 575

Val Gly Asp Pro Gly Arg Lys Trp Ser Gln Gln Ser Lys Gln Val Arg
            580                 585                 590

Gln Lys Ser Val Trp Asp Gln Leu Arg Ala Ala Tyr Glu Asn Ala Gly
            595                 600                 605

Ala Gln Val Pro Glu Pro Ala Asn Val Leu Glu Ile Glu Trp Ser Lys
        610                 615                 620

Gln Gln Tyr Phe Gln Gly Ala Pro Ser Ala Val Tyr Gly Leu Asn Asp
625                 630                 635                 640

Leu Ile Thr Leu Gly Ser Ala Leu Arg Thr Pro Phe Lys Ser Val His
            645                 650                 655

Phe Val Gly Thr Glu Thr Ser Leu Val Trp Lys Gly Tyr Met Glu Gly
            660                 665                 670

Ala Ile Arg Ser Gly Gln Arg Gly Ala Ala Glu Val Val Ala Ser Leu
        675                 680                 685
```

```
Val Pro Ala Ala
    690

<210> SEQ ID NO 20
<211> LENGTH: 1464
<212> TYPE: DNA
<213> ORGANISM: Unknown
<220> FEATURE:
<221> NAME/KEY: sig_peptide
<222> LOCATION: (1)...(72)
<223> OTHER INFORMATION: Barley Alpha Amylase signal sequence.
<220> FEATURE:
<221> NAME/KEY: misc_feature
<222> LOCATION: (73)...(1464)
<223> OTHER INFORMATION: K:trAPAOcDNA
<220> FEATURE:
<221> NAME/KEY: CDS
<222> LOCATION: (1)...(1461)
<223> OTHER INFORMATION: Nucleotide sequence of K:trAPAO translational
      fusion with barley alpha amylase signal sequence, for expression
      and secretion of the mature trAPAO in maize. Nucleotides 1-72,
      barley alpha amylase signal sequence, nucleotides 73-75, added
      lysine residue; nucleotides 76 -1464 , trAPAO cDNA.
<220> FEATURE:
<221> NAME/KEY: misc_feature
<222> LOCATION: (73)...(75)
<223> OTHER INFORMATION: Added lysine residue

<400> SEQUENCE: 20 atg gcc aac aag cac ctg agc ctc tcc ctc ttc ctc gtg ctc ctc ggc         48
Met Ala Asn Lys His Leu Ser Leu Ser Leu Phe Leu Val Leu Leu Gly
            -20                 -15                 -10 ctc tcc gcc tcc ctc gcc agc ggc aaa gac aac gtt gcg gac gtg gta         96
Leu Ser Ala Ser Leu Ala Ser Gly Lys Asp Asn Val Ala Asp Val Val
         -5                  1               5 gtg gtg ggc gct ggc ttg agc ggt ttg gag acg gca cgc aaa gtc cag        144
Val Val Gly Ala Gly Leu Ser Gly Leu Glu Thr Ala Arg Lys Val Gln
     10                  15                  20 gcc gcc ggt ctg tcc tgc ctc gtt ctt gag gcg atg gat cgt gta ggg        192
Ala Ala Gly Leu Ser Cys Leu Val Leu Glu Ala Met Asp Arg Val Gly
 25                  30                  35                  40 gga aag act ctg agc gta caa tcg ggt ccc ggc agg acg act atc aac        240
Gly Lys Thr Leu Ser Val Gln Ser Gly Pro Gly Arg Thr Thr Ile Asn
                 45                  50                  55 gac ctc ggc gct gcg tgg atc aat gac agc aac caa agc gaa gta tcc        288
Asp Leu Gly Ala Ala Trp Ile Asn Asp Ser Asn Gln Ser Glu Val Ser
             60                  65                  70 aga ttg ttt gaa aga ttt cat ttg gag ggc gag ctc cag agg acg act        336
Arg Leu Phe Glu Arg Phe His Leu Glu Gly Glu Leu Gln Arg Thr Thr
         75                  80                  85 gga aat tca atc cat caa gca caa gac ggt aca acc act aca gct cct        384
Gly Asn Ser Ile His Gln Ala Gln Asp Gly Thr Thr Thr Thr Ala Pro
     90                  95                 100 tat ggt gac tcc ttg ctg agc gag gag gtt gca agt gca ctt gcg gaa        432
Tyr Gly Asp Ser Leu Leu Ser Glu Glu Val Ala Ser Ala Leu Ala Glu
105                 110                 115                 120 ctc ctc ccc gta tgg tct cag ctg atc gaa gag cat agc ctt caa gac        480
Leu Leu Pro Val Trp Ser Gln Leu Ile Glu Glu His Ser Leu Gln Asp
                125                 130                 135 ctc aag gcg agc cct cag gcg aag cgg ctc gac agt gtg agc ttc gcg        528
Leu Lys Ala Ser Pro Gln Ala Lys Arg Leu Asp Ser Val Ser Phe Ala
            140                 145                 150 cac tac tgt gag aag gaa cta aac ttg cct gct gtt ctc ggc gta gca        576
His Tyr Cys Glu Lys Glu Leu Asn Leu Pro Ala Val Leu Gly Val Ala
        155                 160                 165
```

```
aac cag atc aca cgc gct ctg ctc ggt gtg gaa gcc cac gag atc agc      624
Asn Gln Ile Thr Arg Ala Leu Leu Gly Val Glu Ala His Glu Ile Ser
    170                 175                 180 atg ctt ttt ctc acc gac tac atc aag agt gcc acc ggt ctc agt aat      672
Met Leu Phe Leu Thr Asp Tyr Ile Lys Ser Ala Thr Gly Leu Ser Asn
185                 190                 195                 200 att ttc tcg gac aag aaa gac ggc ggg cag tat atg cga tgc aaa aca      720
Ile Phe Ser Asp Lys Lys Asp Gly Gly Gln Tyr Met Arg Cys Lys Thr
                205                 210                 215 ggt atg cag tcg att tgc cat gcc atg tca aag gaa ctt gtt cca ggc      768
Gly Met Gln Ser Ile Cys His Ala Met Ser Lys Glu Leu Val Pro Gly
            220                 225                 230 tca gtg cac ctc aac acc ccc gtc gct gaa att gag cag tcg gca tcc      816
Ser Val His Leu Asn Thr Pro Val Ala Glu Ile Glu Gln Ser Ala Ser
        235                 240                 245 ggc tgt aca gta cga tcg gcc tcg ggc gcc gtg ttc cga agc aaa aag      864
Gly Cys Thr Val Arg Ser Ala Ser Gly Ala Val Phe Arg Ser Lys Lys
    250                 255                 260 gtg gtg gtt tcg tta ccg aca acc ttg tat ccc acc ttg aca ttt tca      912
Val Val Val Ser Leu Pro Thr Thr Leu Tyr Pro Thr Leu Thr Phe Ser
265                 270                 275                 280 cca cct ctt ccc gcc gag aag caa gca ttg gcg gaa aat tct atc ctg      960
Pro Pro Leu Pro Ala Glu Lys Gln Ala Leu Ala Glu Asn Ser Ile Leu
                285                 290                 295 ggc tac tat agc aag ata gtc ttc gta tgg gac aag ccg tgg tgg cgc     1008
Gly Tyr Tyr Ser Lys Ile Val Phe Val Trp Asp Lys Pro Trp Trp Arg
            300                 305                 310 gaa caa ggc ttc tcg ggc gtc ctc caa tcg agc tgt gac ccc atc tca     1056
Glu Gln Gly Phe Ser Gly Val Leu Gln Ser Ser Cys Asp Pro Ile Ser
        315                 320                 325 ttt gcc aga gat acc agc atc gac gtc gat cga caa tgg tcc att acc     1104
Phe Ala Arg Asp Thr Ser Ile Asp Val Asp Arg Gln Trp Ser Ile Thr
    330                 335                 340 tgt ttc atg gtc gga gac ccg gga cgg aag tgg tcc caa cag tcc aag     1152
Cys Phe Met Val Gly Asp Pro Gly Arg Lys Trp Ser Gln Gln Ser Lys
345                 350                 355                 360 cag gta cga caa aag tct gtc tgg gac caa ctc cgc gca gcc tac gag     1200
Gln Val Arg Gln Lys Ser Val Trp Asp Gln Leu Arg Ala Ala Tyr Glu
                365                 370                 375 aac gcc ggg gcc caa gtc cca gag ccg gcc aac gtg ctc gaa atc gag     1248
Asn Ala Gly Ala Gln Val Pro Glu Pro Ala Asn Val Leu Glu Ile Glu
            380                 385                 390 tgg tcg aag cag cag tat ttc caa gga gct ccg agc gcc gtc tat ggg     1296
Trp Ser Lys Gln Gln Tyr Phe Gln Gly Ala Pro Ser Ala Val Tyr Gly
        395                 400                 405 ctg aac gat ctc atc aca ctg ggt tcg gcg ctc aga acg ccg ttc aag     1344
Leu Asn Asp Leu Ile Thr Leu Gly Ser Ala Leu Arg Thr Pro Phe Lys
    410                 415                 420 agt gtt cat ttc gtt gga acg gag acg tct tta gtt tgg aaa ggg tat     1392
Ser Val His Phe Val Gly Thr Glu Thr Ser Leu Val Trp Lys Gly Tyr
425                 430                 435                 440 atg gaa ggg gcc ata cga tcg ggt caa cga ggt gct gca gaa gtt gtg     1440
Met Glu Gly Ala Ile Arg Ser Gly Gln Arg Gly Ala Ala Glu Val Val
                445                 450                 455 gct agc ctg gtg cca gca gca tag                                     1464
Ala Ser Leu Val Pro Ala Ala
            460
```

<210> SEQ ID NO 21
<211> LENGTH: 487

```
<212> TYPE: PRT
<213> ORGANISM: Unknown
<220> FEATURE:
<221> NAME/KEY: SIGNAL
<222> LOCATION: (1)...(24)
<223> OTHER INFORMATION: K:trAPAO translational fusion with barley alpha
      amylase signal sequence, for expression and secretion of the
      mature trAPAO in maize.

<400> SEQUENCE: 21
```

Met Ala Asn Lys His Leu Ser Leu Ser Leu Phe Leu Val Leu Leu Gly
            -20                  -15                  -10

Leu Ser Ala Ser Leu Ala Ser Gly Lys Asp Asn Val Ala Asp Val Val
             -5                   1                    5

Val Val Gly Ala Gly Leu Ser Gly Leu Glu Thr Ala Arg Lys Val Gln
 10                      15                   20

Ala Ala Gly Leu Ser Cys Leu Val Leu Glu Ala Met Asp Arg Val Gly
 25                      30                   35                   40

Gly Lys Thr Leu Ser Val Gln Ser Gly Pro Gly Arg Thr Thr Ile Asn
                     45                   50                   55

Asp Leu Gly Ala Ala Trp Ile Asn Asp Ser Asn Gln Ser Glu Val Ser
                 60                   65                   70

Arg Leu Phe Glu Arg Phe His Leu Glu Gly Glu Leu Gln Arg Thr Thr
                 75                   80                   85

Gly Asn Ser Ile His Gln Ala Gln Asp Gly Thr Thr Thr Thr Ala Pro
 90                      95                  100

Tyr Gly Asp Ser Leu Leu Ser Glu Glu Val Ala Ser Ala Leu Ala Glu
105                 110                  115                  120

Leu Leu Pro Val Trp Ser Gln Leu Ile Glu Glu His Ser Leu Gln Asp
                125                  130                  135

Leu Lys Ala Ser Pro Gln Ala Lys Arg Leu Asp Ser Val Ser Phe Ala
                140                  145                  150

His Tyr Cys Glu Lys Glu Leu Asn Leu Pro Ala Val Leu Gly Val Ala
                155                  160                  165

Asn Gln Ile Thr Arg Ala Leu Leu Gly Val Glu Ala His Glu Ile Ser
                170                  175                  180

Met Leu Phe Leu Thr Asp Tyr Ile Lys Ser Ala Thr Gly Leu Ser Asn
185                 190                  195                  200

Ile Phe Ser Asp Lys Lys Asp Gly Gly Gln Tyr Met Arg Cys Lys Thr
                205                  210                  215

Gly Met Gln Ser Ile Cys His Ala Met Ser Lys Glu Leu Val Pro Gly
                220                  225                  230

Ser Val His Leu Asn Thr Pro Val Ala Glu Ile Glu Gln Ser Ala Ser
                235                  240                  245

Gly Cys Thr Val Arg Ser Ala Ser Gly Ala Val Phe Arg Ser Lys Lys
250                 255                  260

Val Val Val Ser Leu Pro Thr Thr Leu Tyr Pro Thr Leu Thr Phe Ser
265                 270                  275                  280

Pro Pro Leu Pro Ala Glu Lys Gln Ala Leu Ala Glu Asn Ser Ile Leu
                285                  290                  295

Gly Tyr Tyr Ser Lys Ile Val Phe Val Trp Asp Lys Pro Trp Trp Arg
                300                  305                  310

Glu Gln Gly Phe Ser Gly Val Leu Gln Ser Ser Cys Asp Pro Ile Ser
                315                  320                  325

Phe Ala Arg Asp Thr Ser Ile Asp Val Asp Arg Gln Trp Ser Ile Thr
                330                  335                  340

```
Cys Phe Met Val Gly Asp Pro Gly Arg Lys Trp Ser Gln Gln Ser Lys
345                 350                 355                 360

Gln Val Arg Gln Lys Ser Val Trp Asp Gln Leu Arg Ala Ala Tyr Glu
            365                 370                 375

Asn Ala Gly Ala Gln Val Pro Glu Pro Ala Asn Val Leu Glu Ile Glu
            380                 385                 390

Trp Ser Lys Gln Gln Tyr Phe Gln Ala Pro Ser Ala Val Tyr Gly
            395                 400                 405

Leu Asn Asp Leu Ile Thr Leu Gly Ser Ala Leu Arg Thr Pro Phe Lys
            410                 415                 420

Ser Val His Phe Val Gly Thr Glu Thr Ser Leu Val Trp Lys Gly Tyr
425                 430                 435                 440

Met Glu Gly Ala Ile Arg Ser Gly Gln Arg Gly Ala Ala Glu Val Val
                445                 450                 455

Ala Ser Leu Val Pro Ala Ala
            460

<210> SEQ ID NO 22
<211> LENGTH: 1803
<212> TYPE: DNA
<213> ORGANISM: Exophiala spinifera
<220> FEATURE:
<221> NAME/KEY: CDS
<222> LOCATION: (1)...(1800)

<400> SEQUENCE: 22 atg gca ctt gca ccg agc tac atc aat ccc cca aac gtc gcc tcc cca       48
Met Ala Leu Ala Pro Ser Tyr Ile Asn Pro Pro Asn Val Ala Ser Pro
  1               5                  10                  15 gca ggg tat tct cac gtc ggc gta ggc cca gac gga ggg agg tat gtg      96
Ala Gly Tyr Ser His Val Gly Val Gly Pro Asp Gly Gly Arg Tyr Val
                 20                  25                  30 aca ata gct gga cag att gga caa gac gct tcg ggc gtg aca gac cct     144
Thr Ile Ala Gly Gln Ile Gly Gln Asp Ala Ser Gly Val Thr Asp Pro
             35                  40                  45 gcc tac gag aaa cag gtt gcc caa gca ttc gcc aat ctg cga gct tgc     192
Ala Tyr Glu Lys Gln Val Ala Gln Ala Phe Ala Asn Leu Arg Ala Cys
         50                  55                  60 ctt gct gca gtt gga gcc act tca aac gac gtc acc aag ctc aat tac     240
Leu Ala Ala Val Gly Ala Thr Ser Asn Asp Val Thr Lys Leu Asn Tyr
 65                  70                  75                  80 tac atc gtc gac tac gcc ccg agc aaa ctc acc gca att gga gat ggg     288
Tyr Ile Val Asp Tyr Ala Pro Ser Lys Leu Thr Ala Ile Gly Asp Gly
                 85                  90                  95 ctg aag gct acc ttt gcc ctt gac agg ctc cct cct tgc acg ctg gtg     336
Leu Lys Ala Thr Phe Ala Leu Asp Arg Leu Pro Pro Cys Thr Leu Val
                100                 105                 110 cca gtg tcg gcc ttg tct tca cct gaa tac ctc ttt gag gtt gat gcc     384
Pro Val Ser Ala Leu Ser Ser Pro Glu Tyr Leu Phe Glu Val Asp Ala
            115                 120                 125 acg gcg ctg gtg ccg gga cac acg acc cca gac aac gtt gcg gac gtg     432
Thr Ala Leu Val Pro Gly His Thr Thr Pro Asp Asn Val Ala Asp Val
            130                 135                 140 gta gtg gtg ggc gct ggc ttg agc ggt ttg gag acg gca cgc aaa gtc     480
Val Val Val Gly Ala Gly Leu Ser Gly Leu Glu Thr Ala Arg Lys Val
145                 150                 155                 160 cag gcc gcc ggt ctg tcc tgc ctc gtt ctt gag gcg atg gat cgt gta     528
Gln Ala Ala Gly Leu Ser Cys Leu Val Leu Glu Ala Met Asp Arg Val
                165                 170                 175
```

```
ggg gga aag act ctg agc gta caa tcg ggt ccc ggc agg acg act atc          576
Gly Gly Lys Thr Leu Ser Val Gln Ser Gly Pro Gly Arg Thr Thr Ile
            180                 185                 190 aac gac ctc ggc gct gcg tgg atc aat gac agc aac caa agc gaa gta          624
Asn Asp Leu Gly Ala Ala Trp Ile Asn Asp Ser Asn Gln Ser Glu Val
            195                 200                 205 tcc aga ttg ttt gaa aga ttt cat ttg gag ggc gag ctc cag agg acg          672
Ser Arg Leu Phe Glu Arg Phe His Leu Glu Gly Glu Leu Gln Arg Thr
210                 215                 220 act gga aat tca atc cat caa gca caa gac ggt aca acc act aca gct          720
Thr Gly Asn Ser Ile His Gln Ala Gln Asp Gly Thr Thr Thr Thr Ala
225                 230                 235                 240 cct tat ggt gac tcc ttg ctg agc gag gag gtt gca agt gca ctt gcg          768
Pro Tyr Gly Asp Ser Leu Leu Ser Glu Glu Val Ala Ser Ala Leu Ala
                245                 250                 255 gaa ctc ctc ccc gta tgg tct cag ctg atc gaa gag cat agc ctt caa          816
Glu Leu Leu Pro Val Trp Ser Gln Leu Ile Glu Glu His Ser Leu Gln
            260                 265                 270 gac ctc aag gcg agc cct cag gcg aag cgg ctc gac agt gtg agc ttc          864
Asp Leu Lys Ala Ser Pro Gln Ala Lys Arg Leu Asp Ser Val Ser Phe
            275                 280                 285 gcg cac tac tgt gag aag gaa cta aac ttg cct gct gtt ctc ggc gta          912
Ala His Tyr Cys Glu Lys Glu Leu Asn Leu Pro Ala Val Leu Gly Val
            290                 295                 300 gca aac cag atc aca cgc gct ctg ctc ggt gtg gaa gcc cac gag atc          960
Ala Asn Gln Ile Thr Arg Ala Leu Leu Gly Val Glu Ala His Glu Ile
305                 310                 315                 320 agc atg ctt ttt ctc acc gac tac atc aag agt gcc acc ggt ctc agt         1008
Ser Met Leu Phe Leu Thr Asp Tyr Ile Lys Ser Ala Thr Gly Leu Ser
                325                 330                 335 aat att ttc tcg gac aag aaa gac ggc ggg cag tat atg cga tgc aaa         1056
Asn Ile Phe Ser Asp Lys Lys Asp Gly Gly Gln Tyr Met Arg Cys Lys
            340                 345                 350 aca ggt atg cag tcg att tgc cat gcc atg tca aag gaa ctt gtt cca         1104
Thr Gly Met Gln Ser Ile Cys His Ala Met Ser Lys Glu Leu Val Pro
            355                 360                 365 ggc tca gtg cac ctc aac acc ccc gtc gct gaa att gag cag tcg gca         1152
Gly Ser Val His Leu Asn Thr Pro Val Ala Glu Ile Glu Gln Ser Ala
370                 375                 380 tcc ggc tgt aca gta cga tcg gcc tcg ggc gcc gtg ttc cga agc aaa         1200
Ser Gly Cys Thr Val Arg Ser Ala Ser Gly Ala Val Phe Arg Ser Lys
385                 390                 395                 400 aag gtg gtg gtt tcg tta ccg aca acc ttg tat ccc acc ttg aca ttt         1248
Lys Val Val Val Ser Leu Pro Thr Thr Leu Tyr Pro Thr Leu Thr Phe
                405                 410                 415 tca cca cct ctt ccc gcc gag aag caa gca ttg gcg gaa aat tct atc         1296
Ser Pro Pro Leu Pro Ala Glu Lys Gln Ala Leu Ala Glu Asn Ser Ile
            420                 425                 430 ctg ggc tac tat agc aag ata gtc ttc gta tgg gac aag ccg tgg tgg         1344
Leu Gly Tyr Tyr Ser Lys Ile Val Phe Val Trp Asp Lys Pro Trp Trp
            435                 440                 445 cgc gaa caa ggc ttc tcg ggc gtc ctc caa tcg agc tgt gac ccc atc         1392
Arg Glu Gln Gly Phe Ser Gly Val Leu Gln Ser Ser Cys Asp Pro Ile
450                 455                 460 tca ttt gcc aga gat acc agc atc gac gtc gat cga caa tgg tcc att         1440
Ser Phe Ala Arg Asp Thr Ser Ile Asp Val Asp Arg Gln Trp Ser Ile
465                 470                 475                 480 acc tgt ttc atg gtc gga gac ccg gga cgg aag tgg tcc caa cag tcc         1488
Thr Cys Phe Met Val Gly Asp Pro Gly Arg Lys Trp Ser Gln Gln Ser
```

```
                485                 490                 495
aag cag gta cga caa aag tct gtc tgg gac caa ctc cgc gca gcc tac   1536
Lys Gln Val Arg Gln Lys Ser Val Trp Asp Gln Leu Arg Ala Ala Tyr
        500                 505                 510 gag aac gcc ggg gcc caa gtc cca gag ccg gcc aac gtg ctc gaa atc   1584
Glu Asn Ala Gly Ala Gln Val Pro Glu Pro Ala Asn Val Leu Glu Ile
        515                 520                 525 gag tgg tcg aag cag cag tat ttc caa gga gct ccg agc gcc gtc tat   1632
Glu Trp Ser Lys Gln Gln Tyr Phe Gln Gly Ala Pro Ser Ala Val Tyr
        530                 535                 540 ggg ctg aac gat ctc atc aca ctg ggt tcg gcg ctc aga acg ccg ttc   1680
Gly Leu Asn Asp Leu Ile Thr Leu Gly Ser Ala Leu Arg Thr Pro Phe
545                 550                 555                 560 aag agt gtt cat ttc gtt gga acg gag acg tct tta gtt tgg aaa ggg   1728
Lys Ser Val His Phe Val Gly Thr Glu Thr Ser Leu Val Trp Lys Gly
                565                 570                 575 tat atg gaa ggg gcc ata cga tcg ggt caa cga ggt gct gca gaa gtt   1776
Tyr Met Glu Gly Ala Ile Arg Ser Gly Gln Arg Gly Ala Ala Glu Val
            580                 585                 590 gtg gct agc ctg gtg cca gca gca tag                               1803
Val Ala Ser Leu Val Pro Ala Ala
        595                 600

<210> SEQ ID NO 23
<211> LENGTH: 600
<212> TYPE: PRT
<213> ORGANISM: Exophiala spinifera

<400> SEQUENCE: 23

Met Ala Leu Ala Pro Ser Tyr Ile Asn Pro Asn Val Ala Ser Pro
 1               5                  10                  15

Ala Gly Tyr Ser His Val Gly Val Gly Pro Asp Gly Gly Arg Tyr Val
                20                  25                  30

Thr Ile Ala Gly Gln Ile Gly Gln Asp Ala Ser Gly Val Thr Asp Pro
            35                  40                  45

Ala Tyr Glu Lys Gln Val Ala Gln Ala Phe Ala Asn Leu Arg Ala Cys
        50                  55                  60

Leu Ala Ala Val Gly Ala Thr Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ala Thr Phe Ala Leu Asp Arg Leu Pro Pro Cys Thr Leu Val
                100                 105                 110

Pro Val Ser Ala Leu Ser Ser Pro Glu Tyr Leu Phe Glu Val Asp Ala
            115                 120                 125

Thr Ala Leu Val Pro Gly His Thr Thr Pro Asp Asn Val Ala Asp Val
        130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
                180                 185                 190

Asn Asp Leu Gly Ala Ala Trp Ile Asn Asp Ser Asn Gln Ser Glu Val
            195                 200                 205

Ser Arg Leu Phe Glu Arg Phe His Leu Glu Gly Glu Leu Gln Arg Thr
        210                 215                 220
```

```
Thr Gly Asn Ser Ile His Gln Ala Gln Asp Gly Thr Thr Thr Ala
225                 230                 235                 240

Pro Tyr Gly Asp Ser Leu Leu Ser Glu Glu Val Ala Ser Ala Leu Ala
            245                 250                 255

Glu Leu Leu Pro Val Trp Ser Gln Leu Ile Glu Glu His Ser Leu Gln
            260                 265                 270

Asp Leu Lys Ala Ser Pro Gln Ala Lys Arg Leu Asp Ser Val Ser Phe
            275                 280                 285

Ala His Tyr Cys Glu Lys Glu Leu Asn Leu Pro Ala Val Leu Gly Val
            290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Phe Ser Asp Lys Lys Asp Gly Gly Gln Tyr Met Arg Cys Lys
                340                 345                 350

Thr Gly Met Gln Ser Ile Cys His Ala Met Ser Lys Glu Leu Val Pro
            355                 360                 365

Gly Ser Val His Leu Asn Thr Pro Val Ala Glu Ile Glu Gln Ser Ala
            370                 375                 380

Ser Gly Cys Thr Val Arg Ser Ala Ser Gly Ala Val Phe Arg Ser Lys
385                 390                 395                 400

Lys Val Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Asn Ser Ile
            420                 425                 430

Leu Gly Tyr Tyr Ser Lys Ile Val Phe Val Trp Asp Lys Pro Trp Trp
            435                 440                 445

Arg Glu Gln Gly Phe Ser Gly Val Leu Gln Ser Ser Cys Asp Pro Ile
450                 455                 460

Ser Phe Ala Arg Asp Thr Ser Ile Asp Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510

Glu Asn Ala Gly Ala Gln Val Pro Glu Pro Ala Asn Val Leu Glu Ile
            515                 520                 525

Glu Trp Ser Lys Gln Gln Tyr Phe Gln Gly Ala Pro Ser Ala Val Tyr
            530                 535                 540

Gly Leu Asn Asp Leu Ile Thr Leu Gly Ser Ala Leu Arg Thr Pro Phe
545                 550                 555                 560

Lys Ser Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 24
<211> LENGTH: 3003
<212> TYPE: DNA
<213> ORGANISM: Unknown
<220> FEATURE:
```

```
<223> OTHER INFORMATION: Sequence is a barley alpha amylase signal
      sequence: esp1 mat: an artificial spacer sequence and K:trAPAO
<220> FEATURE:
<221> NAME/KEY: sig_peptide
<222> LOCATION: (1)...(72)
<223> OTHER INFORMATION: Barley alpha amylase signal sequence
<220> FEATURE:
<221> NAME/KEY: misc_feature
<222> LOCATION: (73)...(1575)
<223> OTHER INFORMATION: esp1 mat
<220> FEATURE:
<221> NAME/KEY: misc_feature
<222> LOCATION: (1576)...(1611)
<223> OTHER INFORMATION: spacer sequence
<220> FEATURE:
<221> NAME/KEY: misc_feature
<222> LOCATION: (1612)...(3000)
<223> OTHER INFORMATION: K:trAPAO
<220> FEATURE:
<221> NAME/KEY: CDS
<222> LOCATION: (1)...(3000)
<221> NAME/KEY: misc_feature
<222> LOCATION: (1612)...(1614)
<223> OTHER INFORMATION: Extra lysine

<400> SEQUENCE: 24 atg gcc aac aag cac ctg agc ctc tcc ctc ttc ctc gtg ctc ctc ggc        48
Met Ala Asn Lys His Leu Ser Leu Ser Leu Phe Leu Val Leu Leu Gly
            -20                 -15                 -10 ctc tcc gcc tcc ctc gcc agc ggc gct cct act gtc aag att gat gct        96
Leu Ser Ala Ser Leu Ala Ser Gly Ala Pro Thr Val Lys Ile Asp Ala
        -5                  1                   5 ggg atg gtg gtc ggc acg act act gtc ccc ggc acc act gcg acc           144
Gly Met Val Val Gly Thr Thr Thr Val Pro Gly Thr Thr Ala Thr
        10                  15                  20 gtc agc gag ttc ttg ggc gtt cct ttt gcc gcc tct ccg aca cga ttt       192
Val Ser Glu Phe Leu Gly Val Pro Phe Ala Ala Ser Pro Thr Arg Phe
 25                  30                  35                  40 gcg cct cct act cgt ccc gtg cct tgg tca acg cct ttg caa gcc act       240
Ala Pro Pro Thr Arg Pro Val Pro Trp Ser Thr Pro Leu Gln Ala Thr
                 45                  50                  55 gca tat ggt cca gca tgc cct caa caa ttc aat tac ccc gaa gaa ctc       288
Ala Tyr Gly Pro Ala Cys Pro Gln Gln Phe Asn Tyr Pro Glu Glu Leu
             60                  65                  70 cgt gag att acg atg gcc tgg ttc aat aca ccg ccc ccg tca gct ggt       336
Arg Glu Ile Thr Met Ala Trp Phe Asn Thr Pro Pro Pro Ser Ala Gly
         75                  80                  85 gaa agt gag gac tgc ctg aac ctc aac atc tac gtc cca gga act gag       384
Glu Ser Glu Asp Cys Leu Asn Leu Asn Ile Tyr Val Pro Gly Thr Glu
     90                  95                  100 aac aca aac aaa gcc gtc atg gtt tgg ata tac ggt gga gcg ctg gaa       432
Asn Thr Asn Lys Ala Val Met Val Trp Ile Tyr Gly Gly Ala Leu Glu
105                 110                 115                 120 tat ggt tgg aat tca ttc cac ctt tac gac ggg gct agt ttc gca gcc       480
Tyr Gly Trp Asn Ser Phe His Leu Tyr Asp Gly Ala Ser Phe Ala Ala
                125                 130                 135 aat cag gat gtc atc gcc gtg acc atc aac tac aga acg aac att ctg       528
Asn Gln Asp Val Ile Ala Val Thr Ile Asn Tyr Arg Thr Asn Ile Leu
            140                 145                 150 ggg ttc cct gct gcc cct cag ctt cca ata aca cag cga aat ctg ggg       576
Gly Phe Pro Ala Ala Pro Gln Leu Pro Ile Thr Gln Arg Asn Leu Gly
        155                 160                 165 ttc cta gac caa agg ttt gct ttg gat tgg gta cag cgg aac atc gca       624
Phe Leu Asp Gln Arg Phe Ala Leu Asp Trp Val Gln Arg Asn Ile Ala
    170                 175                 180
```

-continued

| | | |
|---|---|---|
| gcc ttt ggc ggt gat cct cga aag gtc aca ata ttt ggg cag agt gcg<br>Ala Phe Gly Gly Asp Pro Arg Lys Val Thr Ile Phe Gly Gln Ser Ala<br>185                           190                      195                       200 | 672 |
| ggg ggc aga agt gtc gac gtc ctc ttg acg tct atg cca cac aac cca<br>Gly Gly Arg Ser Val Asp Val Leu Leu Thr Ser Met Pro His Asn Pro<br>                    205                      210                     215 | 720 |
| ccc ttc cga gca gca atc atg gag tcc ggt gtg gct aac tac aac ttc<br>Pro Phe Arg Ala Ala Ile Met Glu Ser Gly Val Ala Asn Tyr Asn Phe<br>        220                      225                     230 | 768 |
| ccc aag gga gat ttg tcc gaa cct tgg aac acc act gtt caa gct ctc<br>Pro Lys Gly Asp Leu Ser Glu Pro Trp Asn Thr Thr Val Gln Ala Leu<br>             235                     240                    245 | 816 |
| aac tgt acc acc agt atc gac atc ttg agt tgt atg aga aga gtc gat<br>Asn Cys Thr Thr Ser Ile Asp Ile Leu Ser Cys Met Arg Arg Val Asp<br>250                         255                      260 | 864 |
| ctc gcc act ctg atg aac acg atc gag caa ctc gga ctt ggg ttt gag<br>Leu Ala Thr Leu Met Asn Thr Ile Glu Gln Leu Gly Leu Gly Phe Glu<br>265                       270                     275                 280 | 912 |
| tac acg ttg gac aac gta acg gct gtg tac cgt tct gaa acg gct cgc<br>Tyr Thr Leu Asp Asn Val Thr Ala Val Tyr Arg Ser Glu Thr Ala Arg<br>                   285                     290                    295 | 960 |
| acg act ggt gac att gct cgt gta cct gtt ctc gtc ggg acg gtg gcc<br>Thr Thr Gly Asp Ile Ala Arg Val Pro Val Leu Val Gly Thr Val Ala<br>            300                     305                   310 | 1008 |
| aac gac gga ctt ctc ttt gtc ctc ggg gag aat gac acc caa gca tat<br>Asn Asp Gly Leu Leu Phe Val Leu Gly Glu Asn Asp Thr Gln Ala Tyr<br>             315                     320                    325 | 1056 |
| ctc gag gag gca atc ccg aat cag ccc gac ctt tac cag act ctc ctt<br>Leu Glu Glu Ala Ile Pro Asn Gln Pro Asp Leu Tyr Gln Thr Leu Leu<br>330                       335                     340 | 1104 |
| gga gca tat ccc att gga tcc cca ggg atc gga tcg cct caa gat cag<br>Gly Ala Tyr Pro Ile Gly Ser Pro Gly Ile Gly Ser Pro Gln Asp Gln<br>345                       350                    355                 360 | 1152 |
| att gcc gcc att gag acc gag gta aga ttc cag tgt cct tct gcc atc<br>Ile Ala Ala Ile Glu Thr Glu Val Arg Phe Gln Cys Pro Ser Ala Ile<br>             365                     370                    375 | 1200 |
| gtg gct cag gac tcc cgg aat cgg ggt atc cct tct tgg cgc tac tac<br>Val Ala Gln Asp Ser Arg Asn Arg Gly Ile Pro Ser Trp Arg Tyr Tyr<br>                 380                     385                    390 | 1248 |
| tac aat gcg acc ttt gag aat ctg gag ctt ttc cct ggg tcc gaa gtg<br>Tyr Asn Ala Thr Phe Glu Asn Leu Glu Leu Phe Pro Gly Ser Glu Val<br>        395                     400                    405 | 1296 |
| tac cac agc tct gaa gtc ggg atg gtg ttt ggc acg tat cct gtc gca<br>Tyr His Ser Ser Glu Val Gly Met Val Phe Gly Thr Tyr Pro Val Ala<br>410                       415                     420 | 1344 |
| agt gcg acc gcc ttg gag gcc cag acg agc aaa tac atg cag ggt gcc<br>Ser Ala Thr Ala Leu Glu Ala Gln Thr Ser Lys Tyr Met Gln Gly Ala<br>425                       430                    435                 440 | 1392 |
| tgg gcg gcc ttt gcc aaa aac ccc atg aat ggg cct ggg tgg aaa caa<br>Trp Ala Ala Phe Ala Lys Asn Pro Met Asn Gly Pro Gly Trp Lys Gln<br>                 445                     450                    455 | 1440 |
| gtg ccg aat gtc gcg gcg ctt ggc tca cca ggc aaa gcc atc cag gtt<br>Val Pro Asn Val Ala Ala Leu Gly Ser Pro Gly Lys Ala Ile Gln Val<br>            460                     465                    470 | 1488 |
| gac gtc tct cca gcg aca ata gac caa cga tgt gcc ttg tac acg cgt<br>Asp Val Ser Pro Ala Thr Ile Asp Gln Arg Cys Ala Leu Tyr Thr Arg<br>             475                     480                    485 | 1536 |
| tat tat act gag ttg ggc aca atc gcg ccg agg aca ttt ggc gga ggc<br>Tyr Tyr Thr Glu Leu Gly Thr Ile Ala Pro Arg Thr Phe Gly Gly Gly<br>        490                     495                    500 | 1584 |

```
agc ggc gga ggc agc ggc gga ggc agc aaa gac aac gtt gcg gac gtg      1632
Ser Gly Gly Gly Ser Gly Gly Gly Ser Lys Asp Asn Val Ala Asp Val
505                 510                 515                 520 gta gtg gtg ggc gct ggc ttg agc ggt ttg gag acg gca cgc aaa gtc      1680
Val Val Val Gly Ala Gly Leu Ser Gly Leu Glu Thr Ala Arg Lys Val
                525                 530                 535 cag gcc gcc ggt ctg tcc tgc ctc gtt ctt gag gcg atg gat cgt gta      1728
Gln Ala Ala Gly Leu Ser Cys Leu Val Leu Glu Ala Met Asp Arg Val
            540                 545                 550 ggg gga aag act ctg agc gta caa tcg ggt ccc ggc agg acg act atc      1776
Gly Gly Lys Thr Leu Ser Val Gln Ser Gly Pro Gly Arg Thr Thr Ile
        555                 560                 565 aac gac ctc ggc gct gcg tgg atc aat gac agc aac caa agc gaa gta      1824
Asn Asp Leu Gly Ala Ala Trp Ile Asn Asp Ser Asn Gln Ser Glu Val
570                 575                 580 tcc aga ttg ttt gaa aga ttt cat ttg gag ggc gag ctc cag agg acg      1872
Ser Arg Leu Phe Glu Arg Phe His Leu Glu Gly Glu Leu Gln Arg Thr
585                 590                 595                 600 act gga aat tca atc cat caa gca caa gac ggt aca acc act aca gct      1920
Thr Gly Asn Ser Ile His Gln Ala Gln Asp Gly Thr Thr Thr Thr Ala
                605                 610                 615 cct tat ggt gac tcc ttg ctg agc gag gag gtt gca agt gca ctt gcg      1968
Pro Tyr Gly Asp Ser Leu Leu Ser Glu Glu Val Ala Ser Ala Leu Ala
            620                 625                 630 gaa ctc ctc ccc gta tgg tct cag ctg atc gaa gag cat agc ctt caa      2016
Glu Leu Leu Pro Val Trp Ser Gln Leu Ile Glu Glu His Ser Leu Gln
        635                 640                 645 gac ctc aag gcg agc cct cag gcg aag cgg ctc gac agt gtg agc ttc      2064
Asp Leu Lys Ala Ser Pro Gln Ala Lys Arg Leu Asp Ser Val Ser Phe
650                 655                 660 gcg cac tac tgt gag aag gaa cta aac ttg cct gct gtt ctc ggc gta      2112
Ala His Tyr Cys Glu Lys Glu Leu Asn Leu Pro Ala Val Leu Gly Val
665                 670                 675                 680 gca aac cag atc aca cgc gct ctg ctc ggt gtg gaa gcc cac gag atc      2160
Ala Asn Gln Ile Thr Arg Ala Leu Leu Gly Val Glu Ala His Glu Ile
                685                 690                 695 agc atg ctt ttt ctc acc gac tac atc aag agt gcc acc ggt ctc agt      2208
Ser Met Leu Phe Leu Thr Asp Tyr Ile Lys Ser Ala Thr Gly Leu Ser
            700                 705                 710 aat att ttc tcg gac aag aaa gac ggc ggg cag tat atg cga tgc aaa      2256
Asn Ile Phe Ser Asp Lys Lys Asp Gly Gly Gln Tyr Met Arg Cys Lys
        715                 720                 725 aca ggt atg cag tcg att tgc cat gcc atg tca aag gaa ctt gtt cca      2304
Thr Gly Met Gln Ser Ile Cys His Ala Met Ser Lys Glu Leu Val Pro
730                 735                 740 ggc tca gtg cac ctc aac acc ccc gtc gct gaa att gag cag tcg gca      2352
Gly Ser Val His Leu Asn Thr Pro Val Ala Glu Ile Glu Gln Ser Ala
745                 750                 755                 760 tcc ggc tgt aca gta cga tcg gcc tcg ggc gcc gtg ttc cga agc aaa      2400
Ser Gly Cys Thr Val Arg Ser Ala Ser Gly Ala Val Phe Arg Ser Lys
                765                 770                 775 aag gtg gtg gtt tcg tta ccg aca acc ttg tat ccc acc ttg aca ttt      2448
Lys Val Val Val Ser Leu Pro Thr Thr Leu Tyr Pro Thr Leu Thr Phe
            780                 785                 790 tca cca cct ctt ccc gcc gag aag caa gca ttg gcg gaa aat tct atc      2496
Ser Pro Pro Leu Pro Ala Glu Lys Gln Ala Leu Ala Glu Asn Ser Ile
        795                 800                 805 ctg ggc tac tat agc aag ata gtc ttc gta tgg gac aag ccg tgg tgg      2544
Leu Gly Tyr Tyr Ser Lys Ile Val Phe Val Trp Asp Lys Pro Trp Trp
```

-continued

```
          810                 815                 820
cgc gaa caa ggc ttc tcg ggc gtc ctc caa tcg agc tgt gac ccc atc      2592
Arg Glu Gln Gly Phe Ser Gly Val Leu Gln Ser Ser Cys Asp Pro Ile
825                 830                 835                 840 tca ttt gcc aga gat acc agc atc gac gtc gat cga caa tgg tcc att      2640
Ser Phe Ala Arg Asp Thr Ser Ile Asp Val Asp Arg Gln Trp Ser Ile
                845                 850                 855 acc tgt ttc atg gtc gga gac ccg gga cgg aag tgg tcc caa cag tcc      2688
Thr Cys Phe Met Val Gly Asp Pro Gly Arg Lys Trp Ser Gln Gln Ser
            860                 865                 870 aag cag gta cga caa aag tct gtc tgg gac caa ctc cgc gca gcc tac      2736
Lys Gln Val Arg Gln Lys Ser Val Trp Asp Gln Leu Arg Ala Ala Tyr
        875                 880                 885 gag aac gcc ggg gcc caa gtc cca gag ccg gcc aac gtg ctc gaa atc      2784
Glu Asn Ala Gly Ala Gln Val Pro Glu Pro Ala Asn Val Leu Glu Ile
890                 895                 900 gag tgg tcg aag cag cag tat ttc caa gga gct ccg agc gcc gtc tat      2832
Glu Trp Ser Lys Gln Gln Tyr Phe Gln Gly Ala Pro Ser Ala Val Tyr
905                 910                 915                 920 ggg ctg aac gat ctc atc aca ctg ggt tcg gcg ctc aga acg ccg ttc      2880
Gly Leu Asn Asp Leu Ile Thr Leu Gly Ser Ala Leu Arg Thr Pro Phe
                925                 930                 935 aag agt gtt cat ttc gtt gga acg gag acg tct tta gtt tgg aaa ggg      2928
Lys Ser Val His Phe Val Gly Thr Glu Thr Ser Leu Val Trp Lys Gly
            940                 945                 950 tat atg gaa ggg gcc ata cga tcg ggt caa cga ggt gct gca gaa gtt      2976
Tyr Met Glu Gly Ala Ile Arg Ser Gly Gln Arg Gly Ala Ala Glu Val
        955                 960                 965 gtg gct agc ctg gtg cca gca gca tag                                   3003
Val Ala Ser Leu Val Pro Ala Ala
    970                 975

<210> SEQ ID NO 25
<211> LENGTH: 1000
<212> TYPE: PRT
<213> ORGANISM: Unknown
<220> FEATURE:
<221> NAME/KEY: SIGNAL
<222> LOCATION: (1)...(24)

<400> SEQUENCE: 25

Met Ala Asn Lys His Leu Ser Leu Ser Leu Phe Leu Val Leu Leu Gly
                -20                 -15                 -10

Leu Ser Ala Ser Leu Ala Ser Gly Ala Pro Thr Val Lys Ile Asp Ala
            -5                  1                   5

Gly Met Val Val Gly Thr Thr Thr Thr Val Pro Gly Thr Thr Ala Thr
    10                  15                  20

Val Ser Glu Phe Leu Gly Val Pro Phe Ala Ala Ser Pro Thr Arg Phe
25                  30                  35                  40

Ala Pro Pro Thr Arg Pro Val Pro Trp Ser Thr Pro Leu Gln Ala Thr
                45                  50                  55

Ala Tyr Gly Pro Ala Cys Pro Gln Gln Phe Asn Tyr Pro Glu Glu Leu
            60                  65                  70

Arg Glu Ile Thr Met Ala Trp Phe Asn Thr Pro Pro Ser Ala Gly
        75                  80                  85

Glu Ser Glu Asp Cys Leu Asn Leu Asn Ile Tyr Val Pro Gly Thr Glu
    90                  95                  100

Asn Thr Asn Lys Ala Val Met Val Trp Ile Tyr Gly Gly Ala Leu Glu
105                 110                 115                 120
```

```
Tyr Gly Trp Asn Ser Phe His Leu Tyr Asp Gly Ala Ser Phe Ala Ala
                125                 130                 135

Asn Gln Asp Val Ile Ala Val Thr Ile Asn Tyr Arg Thr Asn Ile Leu
            140                 145                 150

Gly Phe Pro Ala Ala Pro Gln Leu Pro Ile Thr Gln Arg Asn Leu Gly
        155                 160                 165

Phe Leu Asp Gln Arg Phe Ala Leu Asp Trp Val Gln Arg Asn Ile Ala
    170                 175                 180

Ala Phe Gly Gly Asp Pro Arg Lys Val Thr Ile Phe Gly Gln Ser Ala
185                 190                 195                 200

Gly Gly Arg Ser Val Asp Val Leu Leu Thr Ser Met Pro His Asn Pro
                205                 210                 215

Pro Phe Arg Ala Ala Ile Met Glu Ser Gly Val Ala Asn Tyr Asn Phe
            220                 225                 230

Pro Lys Gly Asp Leu Ser Glu Pro Trp Asn Thr Thr Val Gln Ala Leu
        235                 240                 245

Asn Cys Thr Thr Ser Ile Asp Ile Leu Ser Cys Met Arg Arg Val Asp
    250                 255                 260

Leu Ala Thr Leu Met Asn Thr Ile Glu Gln Leu Gly Leu Gly Phe Glu
265                 270                 275                 280

Tyr Thr Leu Asp Asn Val Thr Ala Val Tyr Arg Ser Glu Thr Ala Arg
                285                 290                 295

Thr Thr Gly Asp Ile Ala Arg Val Pro Val Leu Val Gly Thr Val Ala
            300                 305                 310

Asn Asp Gly Leu Leu Phe Val Leu Gly Glu Asn Asp Thr Gln Ala Tyr
        315                 320                 325

Leu Glu Glu Ala Ile Pro Asn Gln Pro Asp Leu Tyr Gln Thr Leu Leu
    330                 335                 340

Gly Ala Tyr Pro Ile Gly Ser Pro Gly Ile Gly Ser Pro Gln Asp Gln
345                 350                 355                 360

Ile Ala Ala Ile Glu Thr Glu Val Arg Phe Gln Cys Pro Ser Ala Ile
                365                 370                 375

Val Ala Gln Asp Ser Arg Asn Arg Gly Ile Pro Ser Trp Arg Tyr Tyr
            380                 385                 390

Tyr Asn Ala Thr Phe Glu Asn Leu Glu Leu Phe Pro Gly Ser Glu Val
        395                 400                 405

Tyr His Ser Ser Glu Val Gly Met Val Phe Gly Thr Tyr Pro Val Ala
    410                 415                 420

Ser Ala Thr Ala Leu Glu Ala Gln Thr Ser Lys Tyr Met Gln Gly Ala
425                 430                 435                 440

Trp Ala Ala Phe Ala Lys Asn Pro Met Asn Gly Pro Gly Trp Lys Gln
                445                 450                 455

Val Pro Asn Val Ala Ala Leu Gly Ser Pro Gly Lys Ala Ile Gln Val
            460                 465                 470

Asp Val Ser Pro Ala Thr Ile Asp Gln Arg Cys Ala Leu Tyr Thr Arg
        475                 480                 485

Tyr Tyr Thr Glu Leu Gly Thr Ile Ala Pro Arg Thr Phe Gly Gly Gly
    490                 495                 500

Ser Gly Gly Gly Ser Gly Gly Gly Ser Lys Asp Asn Val Ala Asp Val
505                 510                 515                 520

Val Val Val Gly Ala Gly Leu Ser Gly Leu Glu Thr Ala Arg Lys Val
                525                 530                 535
```

-continued

```
Gln Ala Ala Gly Leu Ser Cys Leu Val Leu Glu Ala Met Asp Arg Val
            540                 545                 550
Gly Gly Lys Thr Leu Ser Val Gln Ser Gly Pro Gly Arg Thr Thr Ile
            555                 560                 565
Asn Asp Leu Gly Ala Ala Trp Ile Asn Asp Ser Asn Gln Ser Glu Val
570                 575                 580
Ser Arg Leu Phe Glu Arg Phe His Leu Glu Gly Glu Leu Gln Arg Thr
585                 590                 595                 600
Thr Gly Asn Ser Ile His Gln Ala Gln Asp Gly Thr Thr Thr Ala
                    605                 610                 615
Pro Tyr Gly Asp Ser Leu Leu Ser Glu Glu Val Ala Ser Ala Leu Ala
            620                 625                 630
Glu Leu Leu Pro Val Trp Ser Gln Leu Ile Glu Glu His Ser Leu Gln
            635                 640                 645
Asp Leu Lys Ala Ser Pro Gln Ala Lys Arg Leu Asp Ser Val Ser Phe
            650                 655                 660
Ala His Tyr Cys Glu Lys Glu Leu Asn Leu Pro Ala Val Leu Gly Val
665                 670                 675                 680
Ala Asn Gln Ile Thr Arg Ala Leu Leu Gly Val Glu Ala His Glu Ile
                    685                 690                 695
Ser Met Leu Phe Leu Thr Asp Tyr Ile Lys Ser Ala Thr Gly Leu Ser
            700                 705                 710
Asn Ile Phe Ser Asp Lys Lys Asp Gly Gly Gln Tyr Met Arg Cys Lys
            715                 720                 725
Thr Gly Met Gln Ser Ile Cys His Ala Met Ser Lys Glu Leu Val Pro
            730                 735                 740
Gly Ser Val His Leu Asn Thr Pro Val Ala Glu Ile Glu Gln Ser Ala
745                 750                 755                 760
Ser Gly Cys Thr Val Arg Ser Ala Ser Gly Ala Val Phe Arg Ser Lys
                    765                 770                 775
Lys Val Val Val Ser Leu Pro Thr Thr Leu Tyr Pro Thr Leu Thr Phe
            780                 785                 790
Ser Pro Pro Leu Pro Ala Glu Lys Gln Ala Leu Ala Glu Asn Ser Ile
            795                 800                 805
Leu Gly Tyr Tyr Ser Lys Ile Val Phe Val Trp Asp Lys Pro Trp Trp
            810                 815                 820
Arg Glu Gln Gly Phe Ser Gly Val Leu Gln Ser Ser Cys Asp Pro Ile
825                 830                 835                 840
Ser Phe Ala Arg Asp Thr Ser Ile Asp Val Asp Arg Gln Trp Ser Ile
                    845                 850                 855
Thr Cys Phe Met Val Gly Asp Pro Gly Arg Lys Trp Ser Gln Gln Ser
            860                 865                 870
Lys Gln Val Arg Gln Lys Ser Val Trp Asp Gln Leu Arg Ala Ala Tyr
            875                 880                 885
Glu Asn Ala Gly Ala Gln Val Pro Glu Pro Ala Asn Val Leu Glu Ile
            890                 895                 900
Glu Trp Ser Lys Gln Gln Tyr Phe Gln Gly Ala Pro Ser Ala Val Tyr
905                 910                 915                 920
Gly Leu Asn Asp Leu Ile Thr Leu Gly Ser Ala Leu Arg Thr Pro Phe
                    925                 930                 935
Lys Ser Val His Phe Val Gly Ser Glu Thr Ser Leu Val Trp Lys Gly
                    940                 945                 950
Tyr Met Glu Gly Ala Ile Arg Ser Gly Gln Arg Gly Ala Ala Glu Val
```

-continued

```
                      955                 960                 965
Val Ala Ser Leu Val Pro Ala Ala
    970                 975

<210> SEQ ID NO 26
<211> LENGTH: 2976
<212> TYPE: DNA
<213> ORGANISM: Unknown
<220> FEATURE:
<223> OTHER INFORMATION: Barley alpha amylase signal sequence: BEST1
      mature: artificial spacer: and K:trAPAO.  For plant expression.
<220> FEATURE:
<221> NAME/KEY: sig_peptide
<222> LOCATION: (1)...(72)
<223> OTHER INFORMATION: Barley alpha amylase signal sequence.
<220> FEATURE:
<221> NAME/KEY: mat_peptide
<222> LOCATION: (73)...(1545)
<223> OTHER INFORMATION: BEST1 mature
<220> FEATURE:
<221> NAME/KEY: misc_feature
<222> LOCATION: (1546)...(1584)
<223> OTHER INFORMATION: Artificial spacer sequence
<220> FEATURE:
<221> NAME/KEY: misc_feature
<222> LOCATION: (1585)...(2973)
<223> OTHER INFORMATION: K:trAPAO
<220> FEATURE:
<221> NAME/KEY: CDS
<222> LOCATION: (1)...(2973)
<221> NAME/KEY: misc_feature
<222> LOCATION: (1585)...(1587)
<223> OTHER INFORMATION: Extra lysine

<400> SEQUENCE: 26 atg gcc aac aag cac ctg agc ctc tcc ctc ttc ctc gtg ctc ctc ggc        48
Met Ala Asn Lys His Leu Ser Leu Ser Leu Phe Leu Val Leu Leu Gly
                -20                 -15                 -10 ctc tcc gcc tcc ctc gcc agc ggc acg gat ttt ccg gtc cgc agg acc        96
Leu Ser Ala Ser Leu Ala Ser Gly Thr Asp Phe Pro Val Arg Arg Thr
         -5                  1               5 gat ctg ggc cag gtt cag gga ctg gcc ggg gac gtg atg agc ttt cgc       144
Asp Leu Gly Gln Val Gln Gly Leu Ala Gly Asp Val Met Ser Phe Arg
     10                  15                  20 gga ata ccc tat gca gcg ccg ccg gtg ggc ggg ctg cgt tgg aag ccg       192
Gly Ile Pro Tyr Ala Ala Pro Pro Val Gly Gly Leu Arg Trp Lys Pro
 25                  30                  35                  40 ccc caa cac gcc cgg ccc tgg gcg ggc gtt cgc ccc gcc acc caa ttt       240
Pro Gln His Ala Arg Pro Trp Ala Gly Val Arg Pro Ala Thr Gln Phe
                 45                  50                  55 ggc tcc gac tgc ttc ggc gcg gcc tat ctt cgc aaa ggc agc ctc gcc       288
Gly Ser Asp Cys Phe Gly Ala Ala Tyr Leu Arg Lys Gly Ser Leu Ala
             60                  65                  70 ccc ggc gtg agc gag gac tgt ctt tac ctc aac gta tgg gcg ccg tca       336
Pro Gly Val Ser Glu Asp Cys Leu Tyr Leu Asn Val Trp Ala Pro Ser
         75                  80                  85 ggc gct aaa ccc ggc cag tac ccc gtc atg gtc tgg gtc tac ggc ggc       384
Gly Ala Lys Pro Gly Gln Tyr Pro Val Met Val Trp Val Tyr Gly Gly
     90                  95                 100 ggc ttc gcc ggc ggc acg gcc gcc atg ccc tac tac gac ggc gag gcg       432
Gly Phe Ala Gly Gly Thr Ala Ala Met Pro Tyr Tyr Asp Gly Glu Ala
105                 110                 115                 120 ctt gcc cga cag ggc gtc gtc gtg gtg acg ttt aac tat cgg acg aac       480
Leu Ala Arg Gln Gly Val Val Val Val Thr Phe Asn Tyr Arg Thr Asn
                125                 130                 135 atc ctg ggc ttt ttc gcc cat cct ggt ctc tcg cgc gag agc ccc acc       528
```

```
                    Ile Leu Gly Phe Phe Ala His Pro Gly Leu Ser Arg Glu Ser Pro Thr
                                140                 145                 150 gga act tcg ggc aac tac ggc cta ctc gac att ctc gcc gct ctt cgg              576
Gly Thr Ser Gly Asn Tyr Gly Leu Leu Asp Ile Leu Ala Ala Leu Arg
            155                 160                 165 tgg gtg cag agc aac gcc cgc gcc ttc gga ggg gac ccc ggc cga gtg              624
Trp Val Gln Ser Asn Ala Arg Ala Phe Gly Gly Asp Pro Gly Arg Val
    170                 175                 180 acg gtc ttt ggt gaa tcg gcc gga gcg agc gcg atc gga ctt ctg ctc              672
Thr Val Phe Gly Glu Ser Ala Gly Ala Ser Ala Ile Gly Leu Leu Leu
185                 190                 195                 200 acc tcg ccg ctg agc aag ggt ctc ttc cgt ggc gct atc ctc gaa agt              720
Thr Ser Pro Leu Ser Lys Gly Leu Phe Arg Gly Ala Ile Leu Glu Ser
                205                 210                 215 cca ggg ctg acg cga ccg ctc gcg acg ctc gcc gac agc gcc gcc tcg              768
Pro Gly Leu Thr Arg Pro Leu Ala Thr Leu Ala Asp Ser Ala Ala Ser
        220                 225                 230 ggc gag cgc ctc gac gcc gat ctt tcg cga ctg cgc tcg acc gac cca              816
Gly Glu Arg Leu Asp Ala Asp Leu Ser Arg Leu Arg Ser Thr Asp Pro
            235                 240                 245 gcc acc ctg atg gcg cgc gcc gac gcg gcc cgc ccg gca tcg cgg gac              864
Ala Thr Leu Met Ala Arg Ala Asp Ala Ala Arg Pro Ala Ser Arg Asp
    250                 255                 260 ctg cgc agg ccg cgt ccg acc gga ccg atc gtc gat ggc cat gtg ctg              912
Leu Arg Arg Pro Arg Pro Thr Gly Pro Ile Val Asp Gly His Val Leu
265                 270                 275                 280 ccg cag acc gac agc gcg gcg atc gcg gcg ggg cag ctg gcg ccg gtt              960
Pro Gln Thr Asp Ser Ala Ala Ile Ala Ala Gly Gln Leu Ala Pro Val
                285                 290                 295 cgg gtc ctg atc gga acc aat gcc gac gaa ggc cgc gcc ttc ctc ggg             1008
Arg Val Leu Ile Gly Thr Asn Ala Asp Glu Gly Arg Ala Phe Leu Gly
        300                 305                 310 cgc gcg ccg atg gag acg cca gcg gac tac caa gcc tat ctg gag gcg             1056
Arg Ala Pro Met Glu Thr Pro Ala Asp Tyr Gln Ala Tyr Leu Glu Ala
            315                 320                 325 cag ttt ggc gac caa gcc gcc gcc gtg gcg gcg tgc tat ccc ctc gac             1104
Gln Phe Gly Asp Gln Ala Ala Ala Val Ala Ala Cys Tyr Pro Leu Asp
    330                 335                 340 ggc cgg gcc acg ccc aag gaa atg gtc gcg cgc atc ttc ggc gac aat             1152
Gly Arg Ala Thr Pro Lys Glu Met Val Ala Arg Ile Phe Gly Asp Asn
345                 350                 355                 360 cag ttc aat cgg ggg gtc tcg gcc ttc tcg gaa gcg ctt gtg cgc cag             1200
Gln Phe Asn Arg Gly Val Ser Ala Phe Ser Glu Ala Leu Val Arg Gln
                365                 370                 375 ggc gcg ccc gtg tgg cgt tat cag ttc aac ggt aat acc gag ggt gga             1248
Gly Ala Pro Val Trp Arg Tyr Gln Phe Asn Gly Asn Thr Glu Gly Gly
        380                 385                 390 aga gcg ccg gct acc cac gga gcc gaa att ccc tac gtt ttc ggg gtg             1296
Arg Ala Pro Ala Thr His Gly Ala Glu Ile Pro Tyr Val Phe Gly Val
            395                 400                 405 ttc aag ctc gac gag ttg ggt ctg ttc gat tgg ccg ccc gag ggg ccc             1344
Phe Lys Leu Asp Glu Leu Gly Leu Phe Asp Trp Pro Pro Glu Gly Pro
    410                 415                 420 acg ccc gcc gac cgt gcg ctg ggc caa ctg atg tcc tcc gcc tgg gtc             1392
Thr Pro Ala Asp Arg Ala Leu Gly Gln Leu Met Ser Ser Ala Trp Val
425                 430                 435                 440 cgg ttc gcc aag aat ggc gac ccc gcc ggg gac gcc ctt acc tgg cct             1440
Arg Phe Ala Lys Asn Gly Asp Pro Ala Gly Asp Ala Leu Thr Trp Pro
                445                 450                 455
```

```
                                                          -continued gcc tat tct acg ggc aag tcg acc atg aca ttc ggt ccc gag ggc cgc      1488
Ala Tyr Ser Thr Gly Lys Ser Thr Met Thr Phe Gly Pro Glu Gly Arg
            460                 465                 470 gcg gcg gtg gtg tcg ccc gga cct tcc atc ccc cct tgc gcg gat ggc      1536
Ala Ala Val Val Ser Pro Gly Pro Ser Ile Pro Pro Cys Ala Asp Gly
                475                 480                 485 gcc aag gcg ggg ggc gga ggc agc ggc gga ggc agc ggc gga ggc agc      1584
Ala Lys Ala Gly Gly Gly Ser Gly Gly Gly Ser Gly Gly Gly Ser
            490                 495                 500 aaa gac aac gtt gcg gac gtg gta gtg gtg ggc gct ggc ttg agc ggt      1632
Lys Asp Asn Val Ala Asp Val Val Val Val Gly Ala Gly Leu Ser Gly
505                 510                 515                 520 ttg gag acg gca cgc aaa gtc cag gcc gcc ggt ctg tcc tgc ctc gtt      1680
Leu Glu Thr Ala Arg Lys Val Gln Ala Ala Gly Leu Ser Cys Leu Val
                525                 530                 535 ctt gag gcg atg gat cgt gta ggg gga aag act ctg agc gta caa tcg      1728
Leu Glu Ala Met Asp Arg Val Gly Gly Lys Thr Leu Ser Val Gln Ser
            540                 545                 550 ggt ccc ggc agg acg act atc aac gac ctc ggc gct gcg tgg atc aat      1776
Gly Pro Gly Arg Thr Thr Ile Asn Asp Leu Gly Ala Ala Trp Ile Asn
            555                 560                 565 gac agc aac caa agc gaa gta tcc aga ttg ttt gaa aga ttt cat ttg      1824
Asp Ser Asn Gln Ser Glu Val Ser Arg Leu Phe Glu Arg Phe His Leu
570                 575                 580 gag ggc gag ctc cag agg acg act gga aat tca atc cat caa gca caa      1872
Glu Gly Glu Leu Gln Arg Thr Thr Gly Asn Ser Ile His Gln Ala Gln
                585                 590                 595                 600 gac ggt aca acc act aca gct cct tat ggt gac tcc ttg ctg agc gag      1920
Asp Gly Thr Thr Thr Thr Ala Pro Tyr Gly Asp Ser Leu Leu Ser Glu
                605                 610                 615 gag gtt gca agt gca ctt gcg gaa ctc ctc ccc gta tgg tct cag ctg      1968
Glu Val Ala Ser Ala Leu Ala Glu Leu Leu Pro Val Trp Ser Gln Leu
            620                 625                 630 atc gaa gag cat agc ctt caa gac ctc aag gcg agc cct cag gcg aag      2016
Ile Glu Glu His Ser Leu Gln Asp Leu Lys Ala Ser Pro Gln Ala Lys
            635                 640                 645 cgg ctc gac agt gtg agc ttc gcg cac tac tgt gag aag gaa cta aac      2064
Arg Leu Asp Ser Val Ser Phe Ala His Tyr Cys Glu Lys Glu Leu Asn
650                 655                 660 ttg cct gct gtt ctc ggc gta gca aac cag atc aca cgc gct ctg ctc      2112
Leu Pro Ala Val Leu Gly Val Ala Asn Gln Ile Thr Arg Ala Leu Leu
665                 670                 675                 680 ggt gtg gaa gcc cac gag atc agc atg ctt ttt ctc acc gac tac atc      2160
Gly Val Glu Ala His Glu Ile Ser Met Leu Phe Leu Thr Asp Tyr Ile
                685                 690                 695 aag agt gcc acc ggt ctc agt aat att ttc tcg gac aag aaa gac ggc      2208
Lys Ser Ala Thr Gly Leu Ser Asn Ile Phe Ser Asp Lys Lys Asp Gly
            700                 705                 710 ggg cag tat atg cga tgc aaa aca ggt atg cag tcg att tgc cat gcc      2256
Gly Gln Tyr Met Arg Cys Lys Thr Gly Met Gln Ser Ile Cys His Ala
            715                 720                 725 atg tca aag gaa ctt gtt cca ggc tca gtg cac ctc aac acc ccc gtc      2304
Met Ser Lys Glu Leu Val Pro Gly Ser Val His Leu Asn Thr Pro Val
730                 735                 740 gct gaa att gag cag tcg gca tcc ggc tgt aca gta cga tcg gcc tcg      2352
Ala Glu Ile Glu Gln Ser Ala Ser Gly Cys Thr Val Arg Ser Ala Ser
745                 750                 755                 760 ggc gcc gtg ttc cga agc aaa aag gtg gtg gtt tcg tta ccg aca acc      2400
Gly Ala Val Phe Arg Ser Lys Lys Val Val Val Ser Leu Pro Thr Thr
                765                 770                 775
```

```
ttg tat ccc acc ttg aca ttt tca cca cct ctt ccc gcc gag aag caa         2448
Leu Tyr Pro Thr Leu Thr Phe Ser Pro Pro Leu Pro Ala Glu Lys Gln
            780                 785                 790 gca ttg gcg gaa aat tct atc ctg ggc tac tat agc aag ata gtc ttc         2496
Ala Leu Ala Glu Asn Ser Ile Leu Gly Tyr Tyr Ser Lys Ile Val Phe
        795                 800                 805 gta tgg gac aag ccg tgg tgg cgc gaa caa ggc ttc tcg ggc gtc ctc         2544
Val Trp Asp Lys Pro Trp Trp Arg Glu Gln Gly Phe Ser Gly Val Leu
    810                 815                 820 caa tcg agc tgt gac ccc atc tca ttt gcc aga gat acc agc atc gac         2592
Gln Ser Ser Cys Asp Pro Ile Ser Phe Ala Arg Asp Thr Ser Ile Asp
825                 830                 835                 840 gtc gat cga caa tgg tcc att acc tgt ttc atg gtc gga gac ccg gga         2640
Val Asp Arg Gln Trp Ser Ile Thr Cys Phe Met Val Gly Asp Pro Gly
                845                 850                 855 cgg aag tgg tcc caa cag tcc aag cag gta cga caa aag tct gtc tgg         2688
Arg Lys Trp Ser Gln Gln Ser Lys Gln Val Arg Gln Lys Ser Val Trp
            860                 865                 870 gac caa ctc cgc gca gcc tac gag aac gcc ggg gcc caa gtc cca gag         2736
Asp Gln Leu Arg Ala Ala Tyr Glu Asn Ala Gly Ala Gln Val Pro Glu
        875                 880                 885 ccg gcc aac gtg ctc gaa atc gag tgg tcg aag cag cag tat ttc caa         2784
Pro Ala Asn Val Leu Glu Ile Glu Trp Ser Lys Gln Gln Tyr Phe Gln
    890                 895                 900 gga gct ccg agc gcc gtc tat ggg ctg aac gat ctc atc aca ctg ggt         2832
Gly Ala Pro Ser Ala Val Tyr Gly Leu Asn Asp Leu Ile Thr Leu Gly
905                 910                 915                 920 tcg gcg ctc aga acg ccg ttc aag agt gtt cat ttc gtt gga acg gag         2880
Ser Ala Leu Arg Thr Pro Phe Lys Ser Val His Phe Val Gly Thr Glu
                925                 930                 935 acg tct tta gtt tgg aaa ggg tat atg gaa ggg gcc ata cga tcg ggt         2928
Thr Ser Leu Val Trp Lys Gly Tyr Met Glu Gly Ala Ile Arg Ser Gly
            940                 945                 950 caa cga ggt gct gca gaa gtt gtg gct agc ctg gtg cca gca gca             2973
Gln Arg Gly Ala Ala Glu Val Val Ala Ser Leu Val Pro Ala Ala
        955                 960                 965 tag                                                                     2976
```

<210> SEQ ID NO 27
<211> LENGTH: 991
<212> TYPE: PRT
<213> ORGANISM: Unknown
<220> FEATURE:
<221> NAME/KEY: SIGNAL
<222> LOCATION: (1)...(24)

<400> SEQUENCE: 27

```
Met Ala Asn Lys His Leu Ser Leu Ser Leu Phe Leu Val Leu Leu Gly
                -20                 -15                 -10

Leu Ser Ala Ser Leu Ala Ser Gly Thr Asp Phe Pro Val Arg Arg Thr
            -5                   1                   5

Asp Leu Gly Gln Val Gln Gly Leu Ala Gly Asp Val Met Ser Phe Arg
    10                  15                  20

Gly Ile Pro Tyr Ala Ala Pro Val Gly Gly Leu Arg Trp Lys Pro
25                  30                  35                  40

Pro Gln His Ala Arg Pro Trp Ala Gly Val Arg Pro Ala Thr Gln Phe
                45                  50                  55

Gly Ser Asp Cys Phe Gly Ala Ala Tyr Leu Arg Lys Gly Ser Leu Ala
            60                  65                  70
```

-continued

```
Pro Gly Val Ser Glu Asp Cys Leu Tyr Leu Asn Val Trp Ala Pro Ser
        75                  80                  85
Gly Ala Lys Pro Gly Gln Tyr Pro Val Met Val Trp Val Tyr Gly Gly
 90                  95                 100
Gly Phe Ala Gly Gly Thr Ala Met Pro Tyr Tyr Asp Gly Glu Ala
105                 110                 115                 120
Leu Ala Arg Gln Gly Val Val Val Thr Phe Asn Tyr Arg Thr Asn
                125                 130                 135
Ile Leu Gly Phe Phe Ala His Pro Gly Leu Ser Arg Glu Ser Pro Thr
             140                 145                 150
Gly Thr Ser Gly Asn Tyr Gly Leu Leu Asp Ile Leu Ala Ala Leu Arg
             155                 160                 165
Trp Val Gln Ser Asn Ala Arg Ala Phe Gly Gly Asp Pro Gly Arg Val
     170                 175                 180
Thr Val Phe Gly Glu Ser Ala Gly Ala Ser Ala Ile Gly Leu Leu Leu
185                 190                 195                 200
Thr Ser Pro Leu Ser Lys Gly Leu Phe Arg Gly Ala Ile Leu Glu Ser
                205                 210                 215
Pro Gly Leu Thr Arg Pro Leu Ala Thr Leu Ala Asp Ser Ala Ala Ser
             220                 225                 230
Gly Glu Arg Leu Asp Ala Asp Leu Ser Arg Leu Arg Ser Thr Asp Pro
             235                 240                 245
Ala Thr Leu Met Ala Arg Ala Asp Ala Ala Arg Pro Ala Ser Arg Asp
     250                 255                 260
Leu Arg Arg Pro Arg Pro Thr Gly Pro Ile Val Asp Gly His Val Leu
265                 270                 275                 280
Pro Gln Thr Asp Ser Ala Ala Ile Ala Ala Gly Gln Leu Ala Pro Val
                285                 290                 295
Arg Val Leu Ile Gly Thr Asn Ala Asp Glu Gly Arg Ala Phe Leu Gly
             300                 305                 310
Arg Ala Pro Met Glu Thr Pro Ala Asp Tyr Gln Ala Tyr Leu Glu Ala
             315                 320                 325
Gln Phe Gly Asp Gln Ala Ala Ala Val Ala Ala Cys Tyr Pro Leu Asp
     330                 335                 340
Gly Arg Ala Thr Pro Lys Glu Met Val Ala Arg Ile Phe Gly Asp Asn
345                 350                 355                 360
Gln Phe Asn Arg Gly Val Ser Ala Phe Ser Glu Ala Leu Val Arg Gln
                365                 370                 375
Gly Ala Pro Val Trp Arg Tyr Gln Phe Asn Gly Asn Thr Glu Gly Gly
             380                 385                 390
Arg Ala Pro Ala Thr His Gly Ala Glu Ile Pro Tyr Val Phe Gly Val
             395                 400                 405
Phe Lys Leu Asp Glu Leu Gly Leu Phe Asp Trp Pro Glu Gly Pro
     410                 415                 420
Thr Pro Ala Asp Arg Ala Leu Gly Gln Leu Met Ser Ser Ala Trp Val
425                 430                 435                 440
Arg Phe Ala Lys Asn Gly Asp Pro Ala Gly Asp Ala Leu Thr Trp Pro
                445                 450                 455
Ala Tyr Ser Thr Gly Lys Ser Thr Met Thr Phe Gly Pro Glu Gly Arg
             460                 465                 470
Ala Ala Val Val Ser Pro Gly Ser Ile Pro Pro Cys Ala Asp Gly
             475                 480                 485
```

```
Ala Lys Ala Gly Gly Gly Ser Gly Gly Ser Gly Gly Ser
    490             495             500
Lys Asp Asn Val Ala Asp Val Val Val Gly Ala Gly Leu Ser Gly
505             510             515             520
Leu Glu Thr Ala Arg Lys Val Gln Ala Ala Gly Leu Ser Cys Leu Val
                525             530             535
Leu Glu Ala Met Asp Arg Val Gly Gly Lys Thr Leu Ser Val Gln Ser
            540             545             550
Gly Pro Gly Arg Thr Thr Ile Asn Asp Leu Gly Ala Ala Trp Ile Asn
        555             560             565
Asp Ser Asn Gln Ser Glu Val Ser Arg Leu Phe Glu Arg Phe His Leu
    570             575             580
Glu Gly Glu Leu Gln Arg Thr Thr Gly Asn Ser Ile His Gln Ala Gln
585             590             595             600
Asp Gly Thr Thr Thr Ala Pro Tyr Gly Asp Ser Leu Leu Ser Glu
            605             610             615
Glu Val Ala Ser Ala Leu Ala Glu Leu Leu Pro Val Trp Ser Gln Leu
        620             625             630
Ile Glu Glu His Ser Leu Gln Asp Leu Lys Ala Ser Pro Gln Ala Lys
    635             640             645
Arg Leu Asp Ser Val Ser Phe Ala His Tyr Cys Glu Lys Glu Leu Asn
    650             655             660
Leu Pro Ala Val Leu Gly Val Ala Asn Gln Ile Thr Arg Ala Leu Leu
665             670             675             680
Gly Val Glu Ala His Glu Ile Ser Met Leu Phe Leu Thr Asp Tyr Ile
            685             690             695
Lys Ser Ala Thr Gly Leu Ser Asn Ile Phe Ser Asp Lys Lys Asp Gly
            700             705             710
Gly Gln Tyr Met Arg Cys Lys Thr Gly Met Gln Ser Ile Cys His Ala
        715             720             725
Met Ser Lys Glu Leu Val Pro Gly Ser Val His Leu Asn Thr Pro Val
    730             735             740
Ala Glu Ile Glu Gln Ser Ala Ser Gly Cys Thr Val Arg Ser Ala Ser
745             750             755             760
Gly Ala Val Phe Arg Ser Lys Lys Val Val Ser Leu Pro Thr Thr
            765             770             775
Leu Tyr Pro Thr Leu Thr Phe Ser Pro Pro Leu Pro Ala Glu Lys Gln
            780             785             790
Ala Leu Ala Glu Asn Ser Ile Leu Gly Tyr Tyr Ser Lys Ile Val Phe
        795             800             805
Val Trp Asp Lys Pro Trp Trp Arg Glu Gln Gly Phe Ser Gly Val Leu
    810             815             820
Gln Ser Ser Cys Asp Pro Ile Ser Phe Ala Arg Asp Thr Ser Ile Asp
825             830             835             840
Val Asp Arg Gln Trp Ser Ile Thr Cys Phe Met Val Gly Asp Pro Gly
            845             850             855
Arg Lys Trp Ser Gln Gln Ser Lys Gln Val Arg Gln Lys Ser Val Trp
            860             865             870
Asp Gln Leu Arg Ala Ala Tyr Glu Asn Ala Gly Ala Gln Val Pro Glu
        875             880             885
Pro Ala Asn Val Leu Glu Ile Glu Trp Ser Lys Gln Gln Tyr Phe Gln
    890             895             900
Gly Ala Pro Ser Ala Val Tyr Gly Leu Asn Asp Leu Ile Thr Leu Gly
```

```
                       905                 910                 915                 920
Ser Ala Leu Arg Thr Pro Phe Lys Ser Val His Phe Val Gly Thr Glu
                925                 930                 935
Thr Ser Leu Val Trp Lys Gly Tyr Met Glu Gly Ala Ile Arg Ser Gly
            940                 945                 950
Gln Arg Gly Ala Ala Glu Val Val Ala Ser Leu Val Pro Ala Ala
        955                 960                 965

<210> SEQ ID NO 28
<211> LENGTH: 3618
<212> TYPE: DNA
<213> ORGANISM: Unknown
<220> FEATURE:
<223> OTHER INFORMATION: gst:esp1:sp:K:trapao, 3618. 1-687, gst +
      polylinker; 688-2190, esp1 mat; 2191-2226 spacer; 2227-3615,
      K:trAPAO, extra lysine; 3616-3618, stop codon. For bacterial
      expression.
<220> FEATURE:
<221> NAME/KEY: CDS
<222> LOCATION: (1)...(3615)
<221> NAME/KEY: misc_feature
<222> LOCATION: (1)...(687)
<223> OTHER INFORMATION: gast + polylinker
<220> FEATURE:
<221> NAME/KEY: mat_peptide
<222> LOCATION: (688)...(2190)
<223> OTHER INFORMATION: esp1 mat
<220> FEATURE:
<221> NAME/KEY: misc_feature
<222> LOCATION: (2191)...(2226)
<223> OTHER INFORMATION: spacer sequence
<220> FEATURE:
<221> NAME/KEY: misc_feature
<222> LOCATION: (2227)...(3615)
<223> OTHER INFORMATION: K:trAPAO
<220> FEATURE:
<221> NAME/KEY: misc_feature
<222> LOCATION: (2227)...(2229)
<223> OTHER INFORMATION: Extra lysine

<400> SEQUENCE: 28 atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
 1               5                  10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
                20                  25                  30 tat gag cgc gat gaa ggt gat aaa tgg cga aac aaa aag ttt gaa ttg     144
Tyr Glu Arg Asp Glu Gly Asp Lys Trp Arg Asn Lys Lys Phe Glu Leu
            35                  40                  45 ggt ttg gag ttt ccc aat ctt cct tat tat att gat ggt gat gtt aaa     192
Gly Leu Glu Phe Pro Asn Leu Pro Tyr Tyr Ile Asp Gly Asp Val Lys
         50                 55                  60 tta aca cag tct atg gcc atc ata cgt tat ata gct gac aag cac aac     240
Leu Thr Gln Ser Met Ala Ile Ile Arg Tyr Ile Ala Asp Lys His Asn
 65                  70                  75                  80 atg ttg ggt ggt tgt cca aaa gag cgt gca gag att tca atg ctt gaa     288
Met Leu Gly Gly Cys Pro Lys Glu Arg Ala Glu Ile Ser Met Leu Glu
                 85                  90                  95 gga gcg gtt ttg gat att aga tac ggt gtt tcg aga att gca tat agt     336
Gly Ala Val Leu Asp Ile Arg Tyr Gly Val Ser Arg Ile Ala Tyr Ser
             100                 105                 110 aaa gac ttt gaa act ctc aaa gtt gat ttt ctt agc aag cta cct gaa     384
Lys Asp Phe Glu Thr Leu Lys Val Asp Phe Leu Ser Lys Leu Pro Glu
         115                 120                 125 atg ctg aaa atg ttc gaa gat cgt tta tgt cat aaa aca tat tta aat     432
```

```
Met Leu Lys Met Phe Glu Asp Arg Leu Cys His Lys Thr Tyr Leu Asn
    130                 135                 140 ggt gat cat gta acc cat cct gac ttc atg ttg tat gac gct ctt gat      480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta      528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac      576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc      624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ctg gtt ccg cgt      672
Thr Phe Gly Gly Gly Asp His Pro Pro Lys Ser Asp Leu Val Pro Arg
    210                 215                 220 gga tcc ccg gaa ttc gct cct act gtc aag att gat gct ggg atg gtg      720
Gly Ser Pro Glu Phe Ala Pro Thr Val Lys Ile Asp Ala Gly Met Val
225                 230                 235                 240 gtc ggc acg act act act gtc ccc ggc acc act gcg acc gtc agc gag      768
Val Gly Thr Thr Thr Thr Val Pro Gly Thr Thr Ala Thr Val Ser Glu
                245                 250                 255 ttc ttg ggc gtt cct ttt gcc gcc tct ccg aca cga ttt gcg cct cct      816
Phe Leu Gly Val Pro Phe Ala Ala Ser Pro Thr Arg Phe Ala Pro Pro
            260                 265                 270 act cgt ccc gtg cct tgg tca acg cct ttg caa gcc act gca tat ggt      864
Thr Arg Pro Val Pro Trp Ser Thr Pro Leu Gln Ala Thr Ala Tyr Gly
        275                 280                 285 cca gca tgc cct caa caa ttc aat tac ccc gaa gaa ctc cgt gag att      912
Pro Ala Cys Pro Gln Gln Phe Asn Tyr Pro Glu Glu Leu Arg Glu Ile
    290                 295                 300 acg atg gcc tgg ttc aat aca ccg ccc ccg tca gct ggt gaa agt gag      960
Thr Met Ala Trp Phe Asn Thr Pro Pro Pro Ser Ala Gly Glu Ser Glu
305                 310                 315                 320 gac tgc ctg aac ctc aac atc tac gtc cca gga act gag aac aca aac     1008
Asp Cys Leu Asn Leu Asn Ile Tyr Val Pro Gly Thr Glu Asn Thr Asn
                325                 330                 335 aaa gcc gtc atg gtt tgg ata tac ggt gga gcg ctg gaa tat ggt tgg     1056
Lys Ala Val Met Val Trp Ile Tyr Gly Gly Ala Leu Glu Tyr Gly Trp
            340                 345                 350 aat tca ttc cac ctt tac gac ggg gct agt ttc gca gcc aat cag gat     1104
Asn Ser Phe His Leu Tyr Asp Gly Ala Ser Phe Ala Ala Asn Gln Asp
        355                 360                 365 gtc atc gcc gtg acc atc aac tac aga acg aac att ctg ggg ttc cct     1152
Val Ile Ala Val Thr Ile Asn Tyr Arg Thr Asn Ile Leu Gly Phe Pro
    370                 375                 380 gct gcc cct cag ctt cca ata aca cag cga aat ctg ggg ttc cta gac     1200
Ala Ala Pro Gln Leu Pro Ile Thr Gln Arg Asn Leu Gly Phe Leu Asp
385                 390                 395                 400 caa agg ttt gct ttg gat tgg gta cag cgg aac atc gca gcc ttt ggc     1248
Gln Arg Phe Ala Leu Asp Trp Val Gln Arg Asn Ile Ala Ala Phe Gly
                405                 410                 415 ggt gat cct cga aag gtc aca ata ttt ggg cag agt gcg ggg ggc aga     1296
Gly Asp Pro Arg Lys Val Thr Ile Phe Gly Gln Ser Ala Gly Gly Arg
            420                 425                 430 agt gtc gac gtc ctc ttg acg tct atg cca cac aac cca ccc ttc cga     1344
Ser Val Asp Val Leu Leu Thr Ser Met Pro His Asn Pro Pro Phe Arg
        435                 440                 445
```

-continued

| | | |
|---|---|---|
| gca gca atc atg gag tcc ggt gtg gct aac tac aac ttc ccc aag gga<br>Ala Ala Ile Met Glu Ser Gly Val Ala Asn Tyr Asn Phe Pro Lys Gly<br>    450                                 455                            460 | 1392 |
| gat ttg tcc gaa cct tgg aac acc act gtt caa gct ctc aac tgt acc<br>Asp Leu Ser Glu Pro Trp Asn Thr Thr Val Gln Ala Leu Asn Cys Thr<br>465                        470                              475                        480 | 1440 |
| acc agt atc gac atc ttg agt tgt atg aga aga gtc gat ctc gcc act<br>Thr Ser Ile Asp Ile Leu Ser Cys Met Arg Arg Val Asp Leu Ala Thr<br>                  485                              490                              495 | 1488 |
| ctg atg aac acg atc gag caa ctc gga ctt ggg ttt gag tac acg ttg<br>Leu Met Asn Thr Ile Glu Gln Leu Gly Leu Gly Phe Glu Tyr Thr Leu<br>            500                              505                            510 | 1536 |
| gac aac gta acg gct gtg tac cgt tct gaa acg gct cgc acg act ggt<br>Asp Asn Val Thr Ala Val Tyr Arg Ser Glu Thr Ala Arg Thr Thr Gly<br>                  515                              520                            525 | 1584 |
| gac att gct cgt gta cct gtt ctc gtc ggg acg gtg gcc aac gac gga<br>Asp Ile Ala Arg Val Pro Val Leu Val Gly Thr Val Ala Asn Asp Gly<br>        530                              535                             540 | 1632 |
| ctt ctc ttt gtc ctc ggg gag aat gac acc caa gca tat ctc gag gag<br>Leu Leu Phe Val Leu Gly Glu Asn Asp Thr Gln Ala Tyr Leu Glu Glu<br>545                      550                              555                        560 | 1680 |
| gca atc ccg aat cag ccc gac ctt tac cag act ctc ctt gga gca tat<br>Ala Ile Pro Asn Gln Pro Asp Leu Tyr Gln Thr Leu Leu Gly Ala Tyr<br>                  565                              570                            575 | 1728 |
| ccc att gga tcc cca ggg atc gga tcg cct caa gat cag att gcc gcc<br>Pro Ile Gly Ser Pro Gly Ile Gly Ser Pro Gln Asp Gln Ile Ala Ala<br>        580                              585                             590 | 1776 |
| att gag acc gag gta aga ttc cag tgt cct tct gcc atc gtg gct cag<br>Ile Glu Thr Glu Val Arg Phe Gln Cys Pro Ser Ala Ile Val Ala Gln<br>595                      600                              605 | 1824 |
| gac tcc cgg aat cgg ggt atc cct tct tgg cgc tac tac tac aat gcg<br>Asp Ser Arg Asn Arg Gly Ile Pro Ser Trp Arg Tyr Tyr Tyr Asn Ala<br>            610                              615                            620 | 1872 |
| acc ttt gag aat ctg gag ctt ttc cct ggg tcc gaa gtg tac cac agc<br>Thr Phe Glu Asn Leu Glu Leu Phe Pro Gly Ser Glu Val Tyr His Ser<br>625                      630                              635                        640 | 1920 |
| tct gaa gtc ggg atg gtg ttt ggc acg tat cct gtc gca agt gcg acc<br>Ser Glu Val Gly Met Val Phe Gly Thr Tyr Pro Val Ala Ser Ala Thr<br>                  645                              650                            655 | 1968 |
| gcc ttg gag gcc cag acg agc aaa tac atg cag ggt gcc tgg gcg gcc<br>Ala Leu Glu Ala Gln Thr Ser Lys Tyr Met Gln Gly Ala Trp Ala Ala<br>        660                              665                             670 | 2016 |
| ttt gcc aaa aac ccc atg aat ggg cct ggg tgg aaa caa gtg ccg aat<br>Phe Ala Lys Asn Pro Met Asn Gly Pro Gly Trp Lys Gln Val Pro Asn<br>675                      680                              685 | 2064 |
| gtc gcg gcg ctt ggc tca cca ggc aaa gcc atc cag gtt gac gtc tct<br>Val Ala Ala Leu Gly Ser Pro Gly Lys Ala Ile Gln Val Asp Val Ser<br>            690                              695                            700 | 2112 |
| cca gcg aca ata gac caa cga tgt gcc ttg tac acg cgt tat tat act<br>Pro Ala Thr Ile Asp Gln Arg Cys Ala Leu Tyr Thr Arg Tyr Tyr Thr<br>705                      710                              715                        720 | 2160 |
| gag ttg ggc aca atc gcg ccg agg aca ttt gga gga ggc agc ggc gga<br>Glu Leu Gly Thr Ile Ala Pro Arg Thr Phe Gly Gly Gly Ser Gly Gly<br>                  725                              730                            735 | 2208 |
| ggc agc ggc gga ggc agc aaa gac aac gtt gcg gac gtg gta gtg gtg<br>Gly Ser Gly Gly Gly Ser Lys Asp Asn Val Ala Asp Val Val Val Val<br>            740                              745                            750 | 2256 |
| ggc gct ggc ttg agc ggt ttg gag acg gca cgc aaa gtc cag gcc gcc<br>Gly Ala Gly Leu Ser Gly Leu Glu Thr Ala Arg Lys Val Gln Ala Ala<br>        755                              760                             765 | 2304 |

```
ggt ctg tcc tgc ctc gtt ctt gag gcg atg gat cgt gta ggg gga aag    2352
Gly Leu Ser Cys Leu Val Leu Glu Ala Met Asp Arg Val Gly Gly Lys
    770                 775                 780 act ctg agc gta caa tcg ggt ccc ggc agg acg act atc aac gac ctc    2400
Thr Leu Ser Val Gln Ser Gly Pro Gly Arg Thr Thr Ile Asn Asp Leu
785                 790                 795                 800 ggc gct gcg tgg atc aat gac agc aac caa agc gaa gta tcc aga ttg    2448
Gly Ala Ala Trp Ile Asn Asp Ser Asn Gln Ser Glu Val Ser Arg Leu
                805                 810                 815 ttt gaa aga ttt cat ttg gag ggc gag ctc cag agg acg act gga aat    2496
Phe Glu Arg Phe His Leu Glu Gly Glu Leu Gln Arg Thr Thr Gly Asn
            820                 825                 830 tca atc cat caa gca caa gac ggt aca acc act aca gct cct tat ggt    2544
Ser Ile His Gln Ala Gln Asp Gly Thr Thr Thr Thr Ala Pro Tyr Gly
        835                 840                 845 gac tcc ttg ctg agc gag gag gtt gca agt gca ctt gcg gaa ctc ctc    2592
Asp Ser Leu Leu Ser Glu Glu Val Ala Ser Ala Leu Ala Glu Leu Leu
    850                 855                 860 ccc gta tgg tct cag ctg atc gaa gag cat agc ctt caa gac ctc aag    2640
Pro Val Trp Ser Gln Leu Ile Glu Glu His Ser Leu Gln Asp Leu Lys
865                 870                 875                 880 gcg agc cct cag gcg aag cgg ctc gac agt gtg agc ttc gca cac tac    2688
Ala Ser Pro Gln Ala Lys Arg Leu Asp Ser Val Ser Phe Ala His Tyr
                885                 890                 895 tgt gag aag gaa cta aac ttg cct gct gtt ctc ggc gta gca aac cag    2736
Cys Glu Lys Glu Leu Asn Leu Pro Ala Val Leu Gly Val Ala Asn Gln
            900                 905                 910 atc aca cgc gct ctg ctc ggt gtg gaa gcc cac gag atc agc atg ctt    2784
Ile Thr Arg Ala Leu Leu Gly Val Glu Ala His Glu Ile Ser Met Leu
        915                 920                 925 ttt ctc acc gac tac atc aag agt gcc acc ggt ctc agt aat att ttc    2832
Phe Leu Thr Asp Tyr Ile Lys Ser Ala Thr Gly Leu Ser Asn Ile Phe
    930                 935                 940 tcg gac aag aaa gac ggc ggg cag tat atg cga tgc aaa aca ggt atg    2880
Ser Asp Lys Lys Asp Gly Gly Gln Tyr Met Arg Cys Lys Thr Gly Met
945                 950                 955                 960 cag tcg att tgc cat gcc atg tca aag gaa ctt gtt cca ggc tca gtg    2928
Gln Ser Ile Cys His Ala Met Ser Lys Glu Leu Val Pro Gly Ser Val
                965                 970                 975 cac ctc aac acc ccc gtc gct gaa att gag cag tcg gca tcc ggc tgt    2976
His Leu Asn Thr Pro Val Ala Glu Ile Glu Gln Ser Ala Ser Gly Cys
            980                 985                 990 aca gta cga tcg gcc tcg ggc gcc gtg ttc cga agc aaa aag gtg gtg    3024
Thr Val Arg Ser Ala Ser Gly Ala Val Phe Arg Ser Lys Lys Val Val
        995                 1000                1005 gtt tcg tta ccg aca acc ttg tat ccc acc ttg aca ttt tca cca cct    3072
Val Ser Leu Pro Thr Thr Leu Tyr Pro Thr Leu Thr Phe Ser Pro Pro
    1010                1015                1020 ctt ccc gcc gag aag caa gca ttg gcg gaa aat tct atc ctg ggc tac    3120
Leu Pro Ala Glu Lys Gln Ala Leu Ala Glu Asn Ser Ile Leu Gly Tyr
1025                1030                1035                1040 tat agc aag ata gtc ttc gta tgg gac aag ccg tgg tgg cgc gaa caa    3168
Tyr Ser Lys Ile Val Phe Val Trp Asp Lys Pro Trp Trp Arg Glu Gln
                1045                1050                1055 ggc ttc tcg ggc gtc ctc caa tcg agc tgt gac ccc atc tca ttt gcc    3216
Gly Phe Ser Gly Val Leu Gln Ser Ser Cys Asp Pro Ile Ser Phe Ala
            1060                1065                1070 aga gat acc agc atc gac gtc gat cga caa tgg tcc att acc tgt ttc    3264
Arg Asp Thr Ser Ile Asp Val Asp Arg Gln Trp Ser Ile Thr Cys Phe
```

```
                1075                1080                1085
atg gtc gga gac ccg gga cgg aag tgg tcc caa cag tcc aag cag gta      3312
Met Val Gly Asp Pro Gly Arg Lys Trp Ser Gln Gln Ser Lys Gln Val
        1090                1095                1100 cga caa aag tct gtc tgg gac caa ctc cgc gca gcc tac gag aac gcc      3360
Arg Gln Lys Ser Val Trp Asp Gln Leu Arg Ala Ala Tyr Glu Asn Ala
1105                1110                1115                1120 ggg gcc caa gtc cca gag ccg gcc aac gtg ctc gaa atc gag tgg tcg      3408
Gly Ala Gln Val Pro Glu Pro Ala Asn Val Leu Glu Ile Glu Trp Ser
            1125                1130                1135 aag cag cag tat ttc caa gga gct ccg agc gcc gtc tat ggg ctg aac      3456
Lys Gln Gln Tyr Phe Gln Gly Ala Pro Ser Ala Val Tyr Gly Leu Asn
                1140                1145                1150 gat ctc atc aca ctg ggt tcg gcg ctc aga acg ccg ttc aag agt gtt      3504
Asp Leu Ile Thr Leu Gly Ser Ala Leu Arg Thr Pro Phe Lys Ser Val
            1155                1160                1165 cat ttc gtt gga acg gag acg tct tta gtt tgg aaa ggg tat atg gaa      3552
His Phe Val Gly Thr Glu Thr Ser Leu Val Trp Lys Gly Tyr Met Glu
        1170                1175                1180 ggg gcc ata cga tcg ggt caa cga ggt gct gca gaa gtt gtg gct agc      3600
Gly Ala Ile Arg Ser Gly Gln Arg Gly Ala Ala Glu Val Val Ala Ser
1185                1190                1195                1200 ctg gtg cca gca gca tag                                              3618
Leu Val Pro Ala Ala
            1205

<210> SEQ ID NO 29
<211> LENGTH: 1205
<212> TYPE: PRT
<213> ORGANISM: Unknown

<400> SEQUENCE: 29

Met Ser Pro Ile Leu Gly Tyr Trp Lys Ile Lys Gly Leu Val Gln Pro
 1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
```

-continued

```
                195                 200                 205
Thr Phe Gly Gly Gly Asp His Pro Pro Lys Ser Asp Leu Val Pro Arg
            210                 215                 220

Gly Ser Pro Glu Phe Ala Pro Thr Val Lys Ile Asp Ala Gly Met Val
225                 230                 235                 240

Val Gly Thr Thr Thr Thr Val Pro Gly Thr Thr Ala Thr Val Ser Glu
                245                 250                 255

Phe Leu Gly Val Pro Phe Ala Ala Ser Pro Thr Arg Phe Ala Pro Pro
            260                 265                 270

Thr Arg Pro Val Pro Trp Ser Thr Pro Leu Gln Ala Thr Ala Tyr Gly
        275                 280                 285

Pro Ala Cys Pro Gln Gln Phe Asn Tyr Pro Glu Glu Leu Arg Glu Ile
        290                 295                 300

Thr Met Ala Trp Phe Asn Thr Pro Pro Ser Ala Gly Glu Ser Glu
305                 310                 315                 320

Asp Cys Leu Asn Leu Asn Ile Tyr Val Pro Gly Thr Glu Asn Thr Asn
                325                 330                 335

Lys Ala Val Met Val Trp Ile Tyr Gly Gly Ala Leu Glu Tyr Gly Trp
            340                 345                 350

Asn Ser Phe His Leu Tyr Asp Gly Ala Ser Phe Ala Ala Asn Gln Asp
        355                 360                 365

Val Ile Ala Val Thr Ile Asn Tyr Arg Thr Asn Ile Leu Gly Phe Pro
370                 375                 380

Ala Ala Pro Gln Leu Pro Ile Thr Gln Arg Asn Leu Gly Phe Leu Asp
385                 390                 395                 400

Gln Arg Phe Ala Leu Asp Trp Val Gln Arg Asn Ile Ala Ala Phe Gly
                405                 410                 415

Gly Asp Pro Arg Lys Val Thr Ile Phe Gly Gln Ser Ala Gly Gly Arg
            420                 425                 430

Ser Val Asp Val Leu Leu Thr Ser Met Pro His Asn Pro Pro Phe Arg
        435                 440                 445

Ala Ala Ile Met Glu Ser Gly Val Ala Asn Tyr Asn Phe Pro Lys Gly
        450                 455                 460

Asp Leu Ser Glu Pro Trp Asn Thr Thr Val Gln Ala Leu Asn Cys Thr
465                 470                 475                 480

Thr Ser Ile Asp Ile Leu Ser Cys Met Arg Arg Val Asp Leu Ala Thr
                485                 490                 495

Leu Met Asn Thr Ile Glu Gln Leu Gly Leu Gly Phe Glu Tyr Thr Leu
            500                 505                 510

Asp Asn Val Thr Ala Val Tyr Arg Ser Glu Thr Ala Arg Thr Thr Gly
        515                 520                 525

Asp Ile Ala Arg Val Pro Val Leu Val Gly Thr Val Ala Asn Asp Gly
        530                 535                 540

Leu Leu Phe Val Leu Gly Glu Asn Asp Thr Gln Ala Tyr Leu Glu Glu
545                 550                 555                 560

Ala Ile Pro Asn Gln Pro Asp Leu Tyr Gln Thr Leu Leu Gly Ala Tyr
                565                 570                 575

Pro Ile Gly Ser Pro Gly Ile Gly Ser Pro Gln Asp Gln Ile Ala Ala
            580                 585                 590

Ile Glu Thr Glu Val Arg Phe Gln Cys Pro Ser Ala Ile Val Ala Gln
        595                 600                 605

Asp Ser Arg Asn Arg Gly Ile Pro Ser Trp Arg Tyr Tyr Tyr Asn Ala
        610                 615                 620
```

-continued

```
Thr Phe Glu Asn Leu Glu Leu Phe Pro Gly Ser Glu Val Tyr His Ser
625                 630                 635                 640

Ser Glu Val Gly Met Val Phe Gly Thr Tyr Pro Val Ala Ser Ala Thr
                645                 650                 655

Ala Leu Glu Ala Gln Thr Ser Lys Tyr Met Gln Gly Ala Trp Ala Ala
            660                 665                 670

Phe Ala Lys Asn Pro Met Asn Gly Pro Gly Trp Lys Gln Val Pro Asn
        675                 680                 685

Val Ala Ala Leu Gly Ser Pro Gly Lys Ala Ile Gln Val Asp Val Ser
690                 695                 700

Pro Ala Thr Ile Asp Gln Arg Cys Ala Leu Tyr Thr Arg Tyr Tyr Thr
705                 710                 715                 720

Glu Leu Gly Thr Ile Ala Pro Arg Thr Phe Gly Gly Ser Gly Gly
                725                 730                 735

Gly Ser Gly Gly Gly Ser Lys Asp Asn Val Ala Asp Val Val Val
                740                 745                 750

Gly Ala Gly Leu Ser Gly Leu Glu Thr Ala Arg Lys Val Gln Ala Ala
            755                 760                 765

Gly Leu Ser Cys Leu Val Leu Glu Ala Met Asp Arg Val Gly Gly Lys
770                 775                 780

Thr Leu Ser Val Gln Ser Gly Pro Gly Arg Thr Thr Ile Asn Asp Leu
785                 790                 795                 800

Gly Ala Ala Trp Ile Asn Asp Ser Asn Gln Ser Glu Val Ser Arg Leu
                805                 810                 815

Phe Glu Arg Phe His Leu Glu Gly Glu Leu Gln Arg Thr Thr Gly Asn
                820                 825                 830

Ser Ile His Gln Ala Gln Asp Gly Thr Thr Thr Ala Pro Tyr Gly
                835                 840                 845

Asp Ser Leu Leu Ser Glu Glu Val Ala Ser Ala Leu Ala Glu Leu Leu
            850                 855                 860

Pro Val Trp Ser Gln Leu Ile Glu Glu His Ser Leu Gln Asp Leu Lys
865                 870                 875                 880

Ala Ser Pro Gln Ala Lys Arg Leu Asp Ser Val Ser Phe Ala His Tyr
                885                 890                 895

Cys Glu Lys Glu Leu Asn Leu Pro Ala Val Leu Gly Val Ala Asn Gln
            900                 905                 910

Ile Thr Arg Ala Leu Leu Gly Val Glu Ala His Glu Ile Ser Met Leu
                915                 920                 925

Phe Leu Thr Asp Tyr Ile Lys Ser Ala Thr Gly Leu Ser Asn Ile Phe
        930                 935                 940

Ser Asp Lys Lys Asp Gly Gly Gln Tyr Met Arg Cys Lys Thr Gly Met
945                 950                 955                 960

Gln Ser Ile Cys His Ala Met Ser Lys Glu Leu Val Pro Gly Ser Val
                965                 970                 975

His Leu Asn Thr Pro Val Ala Gly Ile Glu Gln Ser Ala Ser Gly Cys
                980                 985                 990

Thr Val Arg Ser Ala Ser Gly Ala Val Phe Arg Ser Lys Lys Val Val
            995                 1000                1005

Val Ser Leu Pro Thr Thr Leu Tyr Pro Thr Leu Thr Phe Ser Pro Pro
    1010                1015                1020

Leu Pro Ala Glu Lys Gln Ala Leu Ala Glu Asn Ser Ile Leu Gly Tyr
1025                1030                1035                1040
```

```
Tyr Ser Lys Ile Val Phe Val Trp Asp Lys Pro Trp Trp Arg Glu Gln
            1045                1050                1055

Gly Phe Ser Gly Val Leu Gln Ser Ser Cys Asp Pro Ile Ser Phe Ala
            1060                1065                1070

Arg Asp Thr Ser Ile Asp Val Asp Arg Gln Trp Ser Ile Thr Cys Phe
            1075                1080                1085

Met Val Gly Asp Pro Gly Arg Lys Trp Ser Gln Gln Ser Lys Gln Val
        1090                1095                1100

Arg Gln Lys Ser Val Trp Asp Gln Leu Arg Ala Ala Tyr Glu Asn Ala
1105                1110                1115                1120

Gly Ala Gln Val Pro Glu Pro Ala Asn Val Leu Glu Ile Glu Trp Ser
            1125                1130                1135

Lys Gln Gln Tyr Phe Gln Gly Ala Pro Ser Ala Val Tyr Gly Leu Asn
            1140                1145                1150

Asp Leu Ile Thr Leu Gly Ser Ala Leu Arg Thr Pro Phe Lys Ser Val
            1155                1160                1165

His Phe Val Gly Thr Glu Thr Ser Leu Val Trp Lys Gly Tyr Met Glu
        1170                1175                1180

Gly Ala Ile Arg Ser Gly Gln Arg Gly Ala Ala Glu Val Val Ala Ser
1185                1190                1195                1200

Leu Val Pro Ala Ala
            1205

<210> SEQ ID NO 30
<211> LENGTH: 3591
<212> TYPE: DNA
<213> ORGANISM: Unknown
<220> FEATURE:
<223> OTHER INFORMATION: Open reading frame of BEST1:K:trAPAO fusion for
      bacterial expression vector pGEX-4T-1 or similar vector.
      gst:BEST1:sp:K:trAPAO fusion, 3591 nt. 1-687 gst + polylinker,
      688-2163, BEST1 mature; 2164-2199, spacer, 2200-3588, K:trAPAO
<220> FEATURE:
<221> NAME/KEY: misc_feature
<222> LOCATION: (1)...(687)
<223> OTHER INFORMATION: gst + polylinker
<220> FEATURE:
<221> NAME/KEY: mat_peptide
<222> LOCATION: (688)...(2163)
<223> OTHER INFORMATION: BEST1 mature
<220> FEATURE:
<221> NAME/KEY: misc_feature
<222> LOCATION: (2164)...(2199)
<223> OTHER INFORMATION: spacer sequence
<220> FEATURE:
<221> NAME/KEY: misc_feature
<222> LOCATION: (2200)...(3588)
<223> OTHER INFORMATION: K:trAPAO
<220> FEATURE:
<221> NAME/KEY: CDS
<222> LOCATION: (1)...(3588)
<221> NAME/KEY: misc_feature
<222> LOCATION: (2200)...(2202)
<223> OTHER INFORMATION: Extra lysine

<400> SEQUENCE: 30 atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
            20                  25                  30 tat gag cgc gat gaa ggt gat aaa tgg cga aac aaa aag ttt gaa ttg     144
Tyr Glu Arg Asp Glu Gly Asp Lys Trp Arg Asn Lys Lys Phe Glu Leu
        35                  40                  45
```

-continued

```
ggt ttg gag ttt ccc aat ctt cct tat tat att gat ggt gat gtt aaa    192
Gly Leu Glu Phe Pro Asn Leu Pro Tyr Tyr Ile Asp Gly Asp Val Lys
 50                  55                  60 tta aca cag tct atg gcc atc ata cgt tat ata gct gac aag cac aac    240
Leu Thr Gln Ser Met Ala Ile Ile Arg Tyr Ile Ala Asp Lys His Asn
 65                  70                  75                  80 atg ttg ggt ggt tgt cca aaa gag cgt gca gag att tca atg ctt gaa    288
Met Leu Gly Gly Cys Pro Lys Glu Arg Ala Glu Ile Ser Met Leu Glu
                 85                  90                  95 gga gcg gtt ttg gat att aga tac ggt gtt tcg aga att gca tat agt    336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa    384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat    432
Met Leu Lys Met Phe Glu Asp Arg Leu Cys His Lys Thr Tyr Leu Asn
    130                 135                 140 ggt gat cat gta acc cat cct gac ttc atg ttg tat gac gct ctt gat    480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta    528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac    576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc    624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ctg gtt ccg cgt    672
Thr Phe Gly Gly Gly Asp His Pro Pro Lys Ser Asp Leu Val Pro Arg
    210                 215                 220 gga tcc ccg gaa ttc acg gat ttt ccg gtc cgc agg acc gat ctg ggc    720
Gly Ser Pro Glu Phe Thr Asp Phe Pro Val Arg Arg Thr Asp Leu Gly
225                 230                 235                 240 cag gtt cag gga ctg gcc ggg gac gtg atg agc ttt cgc gga ata ccc    768
Gln Val Gln Gly Leu Ala Gly Asp Val Met Ser Phe Arg Gly Ile Pro
                245                 250                 255 tat gca gcg ccg ccg gtg ggc ggg ctg cgt tgg aag ccg ccc caa cac    816
Tyr Ala Ala Pro Pro Val Gly Gly Leu Arg Trp Lys Pro Pro Gln His
            260                 265                 270 gcc cgg ccc tgg gcg ggc gtt cgc ccc gcc acc caa ttt ggc tcc gac    864
Ala Arg Pro Trp Ala Gly Val Arg Pro Ala Thr Gln Phe Gly Ser Asp
        275                 280                 285 tgc ttc ggc gcg gcc tat ctt cgc aaa ggc agc ctc gcc ccc ggc gtg    912
Cys Phe Gly Ala Ala Tyr Leu Arg Lys Gly Ser Leu Ala Pro Gly Val
    290                 295                 300 agc gag gac tgt ctt tac ctc aac gta tgg gcg ccg tca ggc gct aaa    960
Ser Glu Asp Cys Leu Tyr Leu Asn Val Trp Ala Pro Ser Gly Ala Lys
305                 310                 315                 320 ccc ggc cag tac ccc gtc atg gtc tgg gtc tac ggc ggc ggc ttc gcc   1008
Pro Gly Gln Tyr Pro Val Met Val Trp Val Tyr Gly Gly Gly Phe Ala
                325                 330                 335 ggc ggc acg gcc gcc atg ccc tac tac gac ggc gag gcg ctt gcg cga   1056
Gly Gly Thr Ala Ala Met Pro Tyr Tyr Asp Gly Glu Ala Leu Ala Arg
            340                 345                 350 cag ggc gtc gtc gtg gtg acg ttt aac tat cgg acg aac atc ctg ggc   1104
Gln Gly Val Val Val Val Thr Phe Asn Tyr Arg Thr Asn Ile Leu Gly
```

```
                355                 360                 365
ttt ttc gcc cat cct ggt ctc tcg cgc gag agc ccc acc gga act tcg    1152
Phe Phe Ala His Pro Gly Leu Ser Arg Glu Ser Pro Thr Gly Thr Ser
    370                 375                 380 ggc aac tac ggc cta ctc gac att ctc gcc gct ctt cgg tgg gtg cag    1200
Gly Asn Tyr Gly Leu Leu Asp Ile Leu Ala Ala Leu Arg Trp Val Gln
385                 390                 395                 400 agc aac gcc cgc gcc ttc gga ggg gac ccc ggc cga gtg acg gtc ttt    1248
Ser Asn Ala Arg Ala Phe Gly Gly Asp Pro Gly Arg Val Thr Val Phe
                405                 410                 415 ggt gaa tcg gcc gga gcg agc gcg atc gga ctt ctg ctc acc tcg ccg    1296
Gly Glu Ser Ala Gly Ala Ser Ala Ile Gly Leu Leu Leu Thr Ser Pro
            420                 425                 430 ctg agc aag ggt ctc ttc cgt ggc gct atc ctc gaa agt cca ggg ctg    1344
Leu Ser Lys Gly Leu Phe Arg Gly Ala Ile Leu Glu Ser Pro Gly Leu
        435                 440                 445 acg cga ccg ctc gcg acg ctc gcc gac agc gcc gcc tcg ggc gag cgc    1392
Thr Arg Pro Leu Ala Thr Leu Ala Asp Ser Ala Ala Ser Gly Glu Arg
    450                 455                 460 ctc gac gcc gat ctt tcg cga ctg cgc tcg acc gac cca gcc acc ctg    1440
Leu Asp Ala Asp Leu Ser Arg Leu Arg Ser Thr Asp Pro Ala Thr Leu
465                 470                 475                 480 atg gcg cgc gcc gac gcg gcc cgc ccg gca tcg cgg gac ctg cgc agg    1488
Met Ala Arg Ala Asp Ala Ala Arg Pro Ala Ser Arg Asp Leu Arg Arg
                485                 490                 495 ccg cgt ccg acc gga ccg atc gtc gat ggc cat gtg ctg ccg cag acc    1536
Pro Arg Pro Thr Gly Pro Ile Val Asp Gly His Val Leu Pro Gln Thr
            500                 505                 510 gac agc gcg gcg atc gcg gcg ggg cag ctg gcg ccg gtt cgg gtc ctg    1584
Asp Ser Ala Ala Ile Ala Ala Gly Gln Leu Ala Pro Val Arg Val Leu
        515                 520                 525 atc gga acc aat gcc gac gaa ggc cgc gcc ttc ctc ggg cgc gcg ccg    1632
Ile Gly Thr Asn Ala Asp Glu Gly Arg Ala Phe Leu Gly Arg Ala Pro
    530                 535                 540 atg gag acg cca gcg gac tac caa gcc tat ctg gag gcg cag ttt ggc    1680
Met Glu Thr Pro Ala Asp Tyr Gln Ala Tyr Leu Glu Ala Gln Phe Gly
545                 550                 555                 560 gac caa gcc gcc gcc gtg gcg gcg tgc tat ccc ctc gac ggc cgg gcc    1728
Asp Gln Ala Ala Ala Val Ala Ala Cys Tyr Pro Leu Asp Gly Arg Ala
                565                 570                 575 acg ccc aag gaa atg gtc gcg cgc atc ttc ggc gac aat cag ttc aat    1776
Thr Pro Lys Glu Met Val Ala Arg Ile Phe Gly Asp Asn Gln Phe Asn
            580                 585                 590 cgg ggg gtc tcg gcc ttc tcg gaa gcg ctt gtg cgc cag ggc gcg ccc    1824
Arg Gly Val Ser Ala Phe Ser Glu Ala Leu Val Arg Gln Gly Ala Pro
        595                 600                 605 gtg tgg cgt tat cag ttc aac ggt aat acc gag ggt gga aga gcg ccg    1872
Val Trp Arg Tyr Gln Phe Asn Gly Asn Thr Glu Gly Gly Arg Ala Pro
    610                 615                 620 gct acc cac gga gcc gaa att ccc tac gtt ttc ggg gtg ttc aag ctc    1920
Ala Thr His Gly Ala Glu Ile Pro Tyr Val Phe Gly Val Phe Lys Leu
625                 630                 635                 640 gac gag ttg ggt ctg ttc gat tgg ccg ccc gag ggg ccc acg ccc gcc    1968
Asp Glu Leu Gly Leu Phe Asp Trp Pro Pro Glu Gly Pro Thr Pro Ala
                645                 650                 655 gac cgt gcg ctg ggc caa ctg atg tcc tcc gcc tgg gtc cgg ttc gcc    2016
Asp Arg Ala Leu Gly Gln Leu Met Ser Ser Ala Trp Val Arg Phe Ala
            660                 665                 670 aag aat ggc gac ccc gcc ggg gac gcc ctt acc tgg cct gcc tat tct    2064
```

-continued

```
                Lys Asn Gly Asp Pro Ala Gly Asp Ala Leu Thr Trp Pro Ala Tyr Ser
                            675                 680                 685 acg ggc aag tcg acc atg aca ttc ggt ccc gag ggc cgc gcg gcg gtg         2112
Thr Gly Lys Ser Thr Met Thr Phe Gly Pro Glu Gly Arg Ala Ala Val
        690                 695                 700 gtg tcg ccc gga cct tcc atc ccc cct tgc gcg gat ggc gcc aag gcg         2160
Val Ser Pro Gly Pro Ser Ile Pro Pro Cys Ala Asp Gly Ala Lys Ala
705                 710                 715                 720 ggg ggc gga ggc agc ggc gga ggc agc ggc gga ggc agc aaa gac aac         2208
Gly Gly Gly Gly Ser Gly Gly Gly Ser Gly Gly Gly Ser Lys Asp Asn
                    725                 730                 735 gtt gcg gac gtg gta gtg gtg ggc gct ggc ttg agc ggt ttg gag acg         2256
Val Ala Asp Val Val Val Val Gly Ala Gly Leu Ser Gly Leu Glu Thr
                740                 745                 750 gca cgc aaa gtc cag gcc gcc ggt ctg tcc tgc ctc gtt ctt gag gcg         2304
Ala Arg Lys Val Gln Ala Ala Gly Leu Ser Cys Leu Val Leu Glu Ala
            755                 760                 765 atg gat cgt gta ggg gga aag act ctg agc gta caa tcg ggt ccc ggc         2352
Met Asp Arg Val Gly Gly Lys Thr Leu Ser Val Gln Ser Gly Pro Gly
        770                 775                 780 agg acg act atc aac gac ctc ggc gct gcg tgg atc aat gac agc aac         2400
Arg Thr Thr Ile Asn Asp Leu Gly Ala Ala Trp Ile Asn Asp Ser Asn
785                 790                 795                 800 caa agc gaa gta tcc aga ttg ttt gaa aga ttt cat ttg gag ggc gag         2448
Gln Ser Glu Val Ser Arg Leu Phe Glu Arg Phe His Leu Glu Gly Glu
                    805                 810                 815 ctc cag agg acg act gga aat tca atc cat caa gca caa gac ggt aca         2496
Leu Gln Arg Thr Thr Gly Asn Ser Ile His Gln Ala Gln Asp Gly Thr
                820                 825                 830 acc act aca gct cct tat ggt gac tcc ttg ctg agc gag gag gtt gca         2544
Thr Thr Thr Ala Pro Tyr Gly Asp Ser Leu Leu Ser Glu Glu Val Ala
            835                 840                 845 agt gca ctt gcg gaa ctc ctc ccc gta tgg tct cag ctg atc gaa gag         2592
Ser Ala Leu Ala Glu Leu Leu Pro Val Trp Ser Gln Leu Ile Glu Glu
        850                 855                 860 cat agc ctt caa gac ctc aag gcg agc cct cag gcg aag cgg ctc gac         2640
His Ser Leu Gln Asp Leu Lys Ala Ser Pro Gln Ala Lys Arg Leu Asp
865                 870                 875                 880 agt gtg agc ttc gcg cac tac tgt gag aag gaa cta aac ttg cct gct         2688
Ser Val Ser Phe Ala His Tyr Cys Glu Lys Glu Leu Asn Leu Pro Ala
                    885                 890                 895 gtt ctc ggc gta gca aac cag atc aca cgc gct ctg ctc ggt gtg gaa         2736
Val Leu Gly Val Ala Asn Gln Ile Thr Arg Ala Leu Leu Gly Val Glu
                900                 905                 910 gcc cac gag atc agc atg ctt ttt ctc acc gac tac atc aag agt gcc         2784
Ala His Glu Ile Ser Met Leu Phe Leu Thr Asp Tyr Ile Lys Ser Ala
            915                 920                 925 acc ggt ctc agt aat att ttc tcg gac aag aaa gac ggc ggg cag tat         2832
Thr Gly Leu Ser Asn Ile Phe Ser Asp Lys Lys Asp Gly Gly Gln Tyr
        930                 935                 940 atg cga tgc aaa aca ggt atg cag tcg att tgc cat gcc atg tca aag         2880
Met Arg Cys Lys Thr Gly Met Gln Ser Ile Cys His Ala Met Ser Lys
945                 950                 955                 960 gaa ctt gtt cca ggc tca gtg cac ctc aac acc ccc gtc gct gaa att         2928
Glu Leu Val Pro Gly Ser Val His Leu Asn Thr Pro Val Ala Glu Ile
                    965                 970                 975 gag cag tcg gca tcc ggc tgt aca gta cga tcg gcc tcg ggc gcc gtg         2976
Glu Gln Ser Ala Ser Gly Cys Thr Val Arg Ser Ala Ser Gly Ala Val
                980                 985                 990
```

-continued

```
ttc cga agc aaa aag gtg gtg gtt tcg tta ccg aca acc ttg tat ccc       3024
Phe Arg Ser Lys Lys Val Val Val Ser Leu Pro Thr Thr Leu Tyr Pro
        995                 1000                1005 acc ttg aca ttt tca cca cct ctt ccc gcc gag aag caa gca ttg gcg       3072
Thr Leu Thr Phe Ser Pro Pro Leu Pro Ala Glu Lys Gln Ala Leu Ala
    1010                1015                1020 gaa aat tct atc ctg ggc tac tat agc aag ata gtc ttc gta tgg gac       3120
Glu Asn Ser Ile Leu Gly Tyr Tyr Ser Lys Ile Val Phe Val Trp Asp
1025                1030                1035                1040 aag ccg tgg tgg cgc gaa caa ggc ttc tcg ggc gtc ctc caa tcg agc       3168
Lys Pro Trp Trp Arg Glu Gln Gly Phe Ser Gly Val Leu Gln Ser Ser
                1045                1050                1055 tgt gac ccc atc tca ttt gcc aga gat acc agc atc gac gtc gat cga       3216
Cys Asp Pro Ile Ser Phe Ala Arg Asp Thr Ser Ile Asp Val Asp Arg
            1060                1065                1070 caa tgg tcc att acc tgt ttc atg gtc gga gac ccg gga cgg aag tgg       3264
Gln Trp Ser Ile Thr Cys Phe Met Val Gly Asp Pro Gly Arg Lys Trp
        1075                1080                1085 tcc caa cag tcc aag cag gta cga caa aag tct gtc tgg gac caa ctc       3312
Ser Gln Gln Ser Lys Gln Val Arg Gln Lys Ser Val Trp Asp Gln Leu
    1090                1095                1100 cgc gca gcc tac gag aac gcc ggg gcc caa gtc cca gag ccg gcc aac       3360
Arg Ala Ala Tyr Glu Asn Ala Gly Ala Gln Val Pro Glu Pro Ala Asn
1105                1110                1115                1120 gtg ctc gaa atc gag tgg tcg aag cag cag tat ttc caa gga gct ccg       3408
Val Leu Glu Ile Glu Trp Ser Lys Gln Gln Tyr Phe Gln Gly Ala Pro
                1125                1130                1135 agc gcc gtc tat ggg ctg aac gat ctc atc aca ctg ggt tcg gcg ctc       3456
Ser Ala Val Tyr Gly Leu Asn Asp Leu Ile Thr Leu Gly Ser Ala Leu
            1140                1145                1150 aga acg ccg ttc aag agt gtt cat ttc gtt gga acg gag acg tct tta       3504
Arg Thr Pro Phe Lys Ser Val His Phe Val Gly Thr Glu Thr Ser Leu
        1155                1160                1165 gtt tgg aaa ggg tat atg gaa ggg gcc ata cga tcg ggt caa cga ggt       3552
Val Trp Lys Gly Tyr Met Glu Gly Ala Ile Arg Ser Gly Gln Arg Gly
    1170                1175                1180 gct gca gaa gtt gtg gct agc ctg gtg cca gca gca tag                   3591
Ala Ala Glu Val Val Ala Ser Leu Val Pro Ala Ala
1185                1190                1195
```

<210> SEQ ID NO 31
<211> LENGTH: 1196
<212> TYPE: PRT
<213> ORGANISM: Unknown

<400> SEQUENCE: 31

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
```

```
                100              105              110
Lys Asp Phe Glu Thr Leu Lys Val Asp Phe Leu Ser Lys Leu Pro Glu
            115              120              125
Met Leu Lys Met Phe Glu Asp Arg Leu Cys His Lys Thr Tyr Leu Asn
        130              135              140
Gly Asp His Val Thr His Pro Asp Phe Met Leu Tyr Asp Ala Leu Asp
145              150              155              160
Val Val Leu Tyr Met Asp Pro Met Cys Leu Asp Ala Phe Pro Lys Leu
                165              170              175
Val Cys Phe Lys Lys Arg Ile Glu Ala Ile Pro Gln Ile Asp Lys Tyr
            180              185              190
Leu Lys Ser Ser Lys Tyr Ile Ala Trp Pro Leu Gln Gly Trp Gln Ala
        195              200              205
Thr Phe Gly Gly Gly Asp His Pro Pro Lys Ser Asp Leu Val Pro Arg
210              215              220
Gly Ser Pro Glu Phe Thr Asp Phe Pro Val Arg Arg Thr Asp Leu Gly
225              230              235              240
Gln Val Gln Gly Leu Ala Gly Asp Val Met Ser Phe Arg Gly Ile Pro
                245              250              255
Tyr Ala Ala Pro Pro Val Gly Gly Leu Arg Trp Lys Pro Pro Gln His
            260              265              270
Ala Arg Pro Trp Ala Gly Val Arg Pro Ala Thr Gln Phe Gly Ser Asp
        275              280              285
Cys Phe Gly Ala Ala Tyr Leu Arg Lys Gly Ser Leu Ala Pro Gly Val
    290              295              300
Ser Glu Asp Cys Leu Tyr Leu Asn Val Trp Ala Pro Ser Gly Ala Lys
305              310              315              320
Pro Gly Gln Tyr Pro Val Met Val Trp Val Tyr Gly Gly Phe Ala
                325              330              335
Gly Gly Thr Ala Ala Met Pro Tyr Tyr Asp Gly Glu Ala Leu Ala Arg
            340              345              350
Gln Gly Val Val Val Thr Phe Asn Tyr Arg Thr Asn Ile Leu Gly
        355              360              365
Phe Phe Ala His Pro Gly Leu Ser Arg Glu Ser Pro Thr Gly Thr Ser
    370              375              380
Gly Asn Tyr Gly Leu Leu Asp Ile Leu Ala Ala Leu Arg Trp Val Gln
385              390              395              400
Ser Asn Ala Arg Ala Phe Gly Gly Asp Pro Gly Arg Val Thr Val Phe
                405              410              415
Gly Glu Ser Ala Gly Ala Ser Ala Ile Gly Leu Leu Leu Thr Ser Pro
            420              425              430
Leu Ser Lys Gly Leu Phe Arg Gly Ala Ile Leu Glu Ser Pro Gly Leu
        435              440              445
Thr Arg Pro Leu Ala Thr Leu Ala Asp Ser Ala Ala Ser Gly Glu Arg
    450              455              460
Leu Asp Ala Asp Leu Ser Arg Leu Arg Ser Thr Asp Pro Ala Thr Leu
465              470              475              480
Met Ala Arg Ala Asp Ala Ala Arg Pro Ala Ser Arg Asp Leu Arg Arg
                485              490              495
Pro Arg Pro Thr Gly Pro Ile Val Asp Gly His Val Leu Pro Gln Thr
            500              505              510
Asp Ser Ala Ala Ile Ala Ala Gly Gln Leu Ala Pro Val Arg Val Leu
        515              520              525
```

```
Ile Gly Thr Asn Ala Asp Glu Gly Arg Ala Phe Leu Gly Arg Ala Pro
530                 535                 540

Met Glu Thr Pro Ala Asp Tyr Gln Ala Tyr Leu Glu Ala Gln Phe Gly
545                 550                 555                 560

Asp Gln Ala Ala Ala Val Ala Ala Cys Tyr Pro Leu Asp Gly Arg Ala
                565                 570                 575

Thr Pro Lys Glu Met Val Ala Arg Ile Phe Gly Asp Asn Gln Phe Asn
            580                 585                 590

Arg Gly Val Ser Ala Phe Ser Glu Ala Leu Val Arg Gln Gly Ala Pro
        595                 600                 605

Val Trp Arg Tyr Gln Phe Asn Gly Asn Thr Glu Gly Gly Arg Ala Pro
610                 615                 620

Ala Thr His Gly Ala Glu Ile Pro Tyr Val Phe Gly Val Phe Lys Leu
625                 630                 635                 640

Asp Glu Leu Gly Leu Phe Asp Trp Pro Glu Gly Pro Thr Pro Ala
                645                 650                 655

Asp Arg Ala Leu Gly Gln Leu Met Ser Ser Ala Trp Val Arg Phe Ala
                660                 665                 670

Lys Asn Gly Asp Pro Ala Gly Asp Ala Leu Thr Trp Pro Ala Tyr Ser
            675                 680                 685

Thr Gly Lys Ser Thr Met Thr Phe Gly Pro Glu Gly Arg Ala Ala Val
690                 695                 700

Val Ser Pro Gly Pro Ser Ile Pro Pro Cys Ala Asp Gly Ala Lys Ala
705                 710                 715                 720

Gly Gly Gly Gly Ser Gly Gly Ser Gly Gly Gly Ser Lys Asp Asn
                725                 730                 735

Val Ala Asp Val Val Val Gly Ala Gly Leu Ser Gly Leu Glu Thr
            740                 745                 750

Ala Arg Lys Val Gln Ala Ala Gly Leu Ser Cys Leu Val Leu Glu Ala
        755                 760                 765

Met Asp Arg Val Gly Gly Lys Thr Leu Ser Val Gln Ser Gly Pro Gly
770                 775                 780

Arg Thr Thr Ile Asn Asp Leu Gly Ala Ala Trp Ile Asn Asp Ser Asn
785                 790                 795                 800

Gln Ser Glu Val Ser Arg Leu Phe Glu Arg Phe His Leu Glu Gly Glu
                805                 810                 815

Leu Gln Arg Thr Thr Gly Asn Ser Ile His Gln Ala Gln Asp Gly Thr
            820                 825                 830

Thr Thr Thr Ala Pro Tyr Gly Asp Ser Leu Leu Ser Glu Glu Val Ala
        835                 840                 845

Ser Ala Leu Ala Glu Leu Leu Pro Val Trp Ser Gln Leu Ile Glu Glu
850                 855                 860

His Ser Leu Gln Asp Leu Lys Ala Ser Pro Gln Ala Lys Arg Leu Asp
865                 870                 875                 880

Ser Val Ser Phe Ala His Tyr Cys Glu Lys Glu Leu Asn Leu Pro Ala
                885                 890                 895

Val Leu Gly Val Ala Asn Gln Ile Thr Arg Ala Leu Leu Gly Val Glu
            900                 905                 910

Ala His Glu Ile Ser Met Leu Phe Leu Thr Asp Tyr Ile Lys Ser Ala
        915                 920                 925

Thr Gly Leu Ser Asn Ile Phe Ser Asp Lys Lys Asp Gly Gly Gln Tyr
930                 935                 940
```

```
Met Arg Cys Lys Thr Gly Met Gln Ser Ile Cys His Ala Met Ser Lys
945                 950                 955                 960

Glu Leu Val Pro Gly Ser Val His Leu Asn Thr Pro Val Ala Glu Ile
                965                 970                 975

Glu Gln Ser Ala Ser Gly Cys Thr Val Arg Ser Ala Ser Gly Ala Val
            980                 985                 990

Phe Arg Ser Lys Lys Val Val Ser Leu Pro Thr Thr Leu Tyr Pro
        995                 1000                1005

Thr Leu Thr Phe Ser Pro Pro Leu Pro Ala Glu Lys Gln Ala Leu Ala
    1010                1015                1020

Glu Asn Ser Ile Leu Gly Tyr Tyr Ser Lys Ile Val Phe Val Trp Asp
1025                1030                1035                1040

Lys Pro Trp Trp Arg Glu Gln Gly Phe Ser Gly Val Leu Gln Ser Ser
                1045                1050                1055

Cys Asp Pro Ile Ser Phe Ala Arg Asp Thr Ser Ile Asp Val Asp Arg
            1060                1065                1070

Gln Trp Ser Ile Thr Cys Phe Met Val Gly Asp Pro Gly Arg Lys Trp
        1075                1080                1085

Ser Gln Gln Ser Lys Gln Val Arg Gln Lys Ser Val Trp Asp Gln Leu
    1090                1095                1100

Arg Ala Ala Tyr Glu Asn Ala Gly Ala Gln Val Pro Glu Pro Ala Asn
1105                1110                1115                1120

Val Leu Glu Ile Glu Trp Ser Lys Gln Gln Tyr Phe Gln Gly Ala Pro
                1125                1130                1135

Ser Ala Val Tyr Gly Leu Asn Asp Leu Ile Thr Leu Gly Ser Ala Leu
            1140                1145                1150

Arg Thr Pro Phe Lys Ser Val His Phe Val Gly Thr Glu Thr Ser Leu
        1155                1160                1165

Val Trp Lys Gly Tyr Met Glu Gly Ala Ile Arg Ser Gly Gln Arg Gly
    1170                1175                1180

Ala Ala Glu Val Val Ala Ser Leu Val Pro Ala Ala
1185                1190                1195

<210> SEQ ID NO 32
<211> LENGTH: 2490
<212> TYPE: DNA
<213> ORGANISM: Unknown
<220> FEATURE:
<223> OTHER INFORMATION: GST:glyc(-)APAO open reading frame, 2490 nt;
      GST and linker, nt 1-687; Glyc (-) APAO, nt 688-2490; mutation in
      putative glycosylation sites in bold and underlined, nt  1288-1290
      (AAT-> TCC) and nt 1303-1305 (AGC-> AAC).
<220> FEATURE:
<221> NAME/KEY: CDS
<222> LOCATION: (1)...(2487)
<221> NAME/KEY: misc_feature
<222> LOCATION: (1)...(687)
<223> OTHER INFORMATION: GST and linker
<220> FEATURE:
<221> NAME/KEY: misc_feature
<222> LOCATION: (688)...(2490)
<223> OTHER INFORMATION: Glyc (-) APAO
<220> FEATURE:
<221> NAME/KEY: mutation
<222> LOCATION: (1288)...(1290)
<223> OTHER INFORMATION: mutation in putative glycosylation site
      (AAT->TCC)
<220> FEATURE:
<221> NAME/KEY: mutation
<222> LOCATION: (1303)...(1305)
<223> OTHER INFORMATION: mutation in putative glycosylation site
      (AGC->AAC)
```

```
<400> SEQUENCE: 32 atg tcc cct ata cta ggt tat tgg aaa att aag ggc ctt gtg caa ccc     48
Met Ser Pro Ile Leu Gly Tyr Trp Lys Ile Lys Gly Leu Val Gln Pro
 1               5                  10                  15 act cga ctt ctt ttg gaa tat ctt gaa gaa aaa tat gaa gag cat ttg     96
Thr Arg Leu Leu Leu Glu Tyr Leu Glu Glu Lys Tyr Glu Glu His Leu
             20                  25                  30 tat gag cgc gat gaa ggt gat aaa tgg cga aac aaa aag ttt gaa ttg    144
Tyr Glu Arg Asp Glu Gly Asp Lys Trp Arg Asn Lys Lys Phe Glu Leu
         35                  40                  45 ggt ttg gag ttt ccc aat ctt cct tat tat att gat ggt gat gtt aaa    192
Gly Leu Glu Phe Pro Asn Leu Pro Tyr Tyr Ile Asp Gly Asp Val Lys
     50                  55                  60 tta aca cag tct atg gcc atc ata cgt tat ata gct gac aag cac aac    240
Leu Thr Gln Ser Met Ala Ile Ile Arg Tyr Ile Ala Asp Lys His Asn
 65                  70                  75                  80 atg ttg ggt ggt tgt cca aaa gag cgt gca gag att tca atg ctt gaa    288
Met Leu Gly Gly Cys Pro Lys Glu Arg Ala Glu Ile Ser Met Leu Glu
                 85                  90                  95 gga gcg gtt ttg gat att aga tac ggt gtt tcg aga att gca tat agt    336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa    384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat    432
Met Leu Lys Met Phe Glu Asp Arg Leu Cys His Lys Thr Tyr Leu Asn
    130                 135                 140 ggt gat cat gta acc cat cct gac ttc atg ttg tat gac gct ctt gat    480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta    528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac    576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc    624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ctg gtt ccg cgt    672
Thr Phe Gly Gly Gly Asp His Pro Pro Lys Ser Asp Leu Val Pro Arg
    210                 215                 220 gga tcc ccg gaa ttc atg gca ctt gca ccg agc tac atc aat ccc cca    720
Gly Ser Pro Glu Phe Met Ala Leu Ala Pro Ser Tyr Ile Asn Pro Pro
225                 230                 235                 240 aac gtc gcc tcc cca gca ggg tat tct cac gtc ggc gta ggc cca gac    768
Asn Val Ala Ser Pro Ala Gly Tyr Ser His Val Gly Val Gly Pro Asp
                245                 250                 255 gga ggg agg tat gtg aca ata gct gga cag att gga caa gac gct tcg    816
Gly Gly Arg Tyr Val Thr Ile Ala Gly Gln Ile Gly Gln Asp Ala Ser
            260                 265                 270 ggc gtg aca gac cct gcc tac gag aaa cag gtt gcc caa gca ttc gcc    864
Gly Val Thr Asp Pro Ala Tyr Glu Lys Gln Val Ala Gln Ala Phe Ala
        275                 280                 285 aat ctg cga gct tgc ctt gct gca gtt gga gcc act tca aac gac gtc    912
Asn Leu Arg Ala Cys Leu Ala Ala Val Gly Ala Thr Ser Asn Asp Val
    290                 295                 300 acc aag ctc aat tac tac atc gtc gac tac gcc ccg agc aaa ctc acc    960
```

```
Thr Lys Leu Asn Tyr Tyr Ile Val Asp Tyr Ala Pro Ser Lys Leu Thr
305                 310                 315                 320 gca att gga gat ggg ctg aag gct acc ttt gcc ctt gac agg ctc cct      1008
Ala Ile Gly Asp Gly Leu Lys Ala Thr Phe Ala Leu Asp Arg Leu Pro
                325                 330                 335 cct tgc acg ctg gtg cca gtg tcg gcc ttg tct tca cct gaa tac ctc      1056
Pro Cys Thr Leu Val Pro Val Ser Ala Leu Ser Ser Pro Glu Tyr Leu
            340                 345                 350 ttt gag gtt gat gcc acg gcg ctg gtg ccg gga cac acg acc cca gac      1104
Phe Glu Val Asp Ala Thr Ala Leu Val Pro Gly His Thr Thr Pro Asp
                355                 360                 365 aac gtt gcg gac gtg gta gtg gtg ggc gct ggc ttg agc ggt ttg gag      1152
Asn Val Ala Asp Val Val Val Val Gly Ala Gly Leu Ser Gly Leu Glu
370                 375                 380 acg gca cgc aaa gtc cag gcc gcc ggt ctg tcc tgc ctc gtt ctt gag      1200
Thr Ala Arg Lys Val Gln Ala Ala Gly Leu Ser Cys Leu Val Leu Glu
385                 390                 395                 400 gcg atg gat cgt gta ggg gga aag act ctg agc gta caa tcg ggt ccc      1248
Ala Met Asp Arg Val Gly Gly Lys Thr Leu Ser Val Gln Ser Gly Pro
                405                 410                 415 ggc agg acg act atc aac gac ctc ggc gct gcg tgg atc tcc gac agc      1296
Gly Arg Thr Thr Ile Asn Asp Leu Gly Ala Ala Trp Ile Ser Asp Ser
            420                 425                 430 aac caa aac gaa gta tcc aga ttg ttt gaa aga ttt cat ttg gag ggc      1344
Asn Gln Asn Glu Val Ser Arg Leu Phe Glu Arg Phe His Leu Glu Gly
                435                 440                 445 gag ctc cag agg acg act gga aat tca atc cat caa gca caa gac ggt      1392
Glu Leu Gln Arg Thr Thr Gly Asn Ser Ile His Gln Ala Gln Asp Gly
        450                 455                 460 aca acc act aca gct cct tat ggt gac tcc ttg ctg agc gag gag gtt      1440
Thr Thr Thr Thr Ala Pro Tyr Gly Asp Ser Leu Leu Ser Glu Glu Val
465                 470                 475                 480 gca agt gca ctt gcg gaa ctc ctc ccc gta tgg tct cag ctg atc gaa      1488
Ala Ser Ala Leu Ala Glu Leu Leu Pro Val Trp Ser Gln Leu Ile Glu
                485                 490                 495 gag cat agc ctt caa gac ctc aag gcg agc cct cag gcg aag cgg ctc      1536
Glu His Ser Leu Gln Asp Leu Lys Ala Ser Pro Gln Ala Lys Arg Leu
            500                 505                 510 gac agt gtg agc ttc gcg cac tac tgt gag aag gaa cta aac ttg cct      1584
Asp Ser Val Ser Phe Ala His Tyr Cys Glu Lys Glu Leu Asn Leu Pro
        515                 520                 525 gct gtt ctc ggc gta gca aac cag atc aca cgc gct ctg ctc ggt gtg      1632
Ala Val Leu Gly Val Ala Asn Gln Ile Thr Arg Ala Leu Leu Gly Val
    530                 535                 540 gaa gcc cac gag atc agc atg ctt ttt ctc acc gac tac atc aag agt      1680
Glu Ala His Glu Ile Ser Met Leu Phe Leu Thr Asp Tyr Ile Lys Ser
545                 550                 555                 560 gcc acc ggt ctc agt aat att ttc tcg gac aag aaa gac ggc ggg cag      1728
Ala Thr Gly Leu Ser Asn Ile Phe Ser Asp Lys Lys Asp Gly Gly Gln
                565                 570                 575 tat atg cga tgc aaa aca ggt atg cag tcg att tgc cat gcc atg tca      1776
Tyr Met Arg Cys Lys Thr Gly Met Gln Ser Ile Cys His Ala Met Ser
            580                 585                 590 aag gaa ctt gtt cca ggc tca gtg cac ctc aac acc ccc gtc gct gaa      1824
Lys Glu Leu Val Pro Gly Ser Val His Leu Asn Thr Pro Val Ala Glu
        595                 600                 605 att gag cag tcg gca tcc ggc tgt aca gta cga tcg gcc tcg ggc gcc      1872
Ile Glu Gln Ser Ala Ser Gly Cys Thr Val Arg Ser Ala Ser Gly Ala
    610                 615                 620
```

```
gtg ttc cga agc aaa aag gtg gtg gtt tcg tta ccg aca acc ttg tat    1920
Val Phe Arg Ser Lys Lys Val Val Val Ser Leu Pro Thr Thr Leu Tyr
625                 630                 635                 640 ccc acc ttg aca ttt tca cca cct ctt ccc gcc gag aag caa gca ttg    1968
Pro Thr Leu Thr Phe Ser Pro Pro Leu Pro Ala Glu Lys Gln Ala Leu
                645                 650                 655 gcg gaa aat tct atc ctg ggc tac tat agc aag ata gtc ttc gta tgg    2016
Ala Glu Asn Ser Ile Leu Gly Tyr Tyr Ser Lys Ile Val Phe Val Trp
            660                 665                 670 gac aag ccg tgg tgg cgc gaa caa ggc ttc tcg ggc gtc ctc caa tcg    2064
Asp Lys Pro Trp Trp Arg Glu Gln Gly Phe Ser Gly Val Leu Gln Ser
        675                 680                 685 agc tgt gac ccc atc tca ttt gcc aga gat acc agc atc gac gtc gat    2112
Ser Cys Asp Pro Ile Ser Phe Ala Arg Asp Thr Ser Ile Asp Val Asp
    690                 695                 700 cga caa tgg tcc att acc tgt ttc atg gtc gga gac ccg gga cgg aag    2160
Arg Gln Trp Ser Ile Thr Cys Phe Met Val Gly Asp Pro Gly Arg Lys
705                 710                 715                 720 tgg tcc caa cag tcc aag cag gta cga caa aag tct gtc tgg gac caa    2208
Trp Ser Gln Gln Ser Lys Gln Val Arg Gln Lys Ser Val Trp Asp Gln
                725                 730                 735 ctc cgc gca gcc tac gag aac gcc ggg gcc caa gtc cca gag ccg gcc    2256
Leu Arg Ala Ala Tyr Glu Asn Ala Gly Ala Gln Val Pro Glu Pro Ala
            740                 745                 750 aac gtg ctc gaa atc gag tgg tcg aag cag cag tat ttc caa gga gct    2304
Asn Val Leu Glu Ile Glu Trp Ser Lys Gln Gln Tyr Phe Gln Gly Ala
        755                 760                 765 ccg agc gcc gtc tat ggg ctg aac gat ctc atc aca ctg ggt tcg gcg    2352
Pro Ser Ala Val Tyr Gly Leu Asn Asp Leu Ile Thr Leu Gly Ser Ala
    770                 775                 780 ctc aga acg ccg ttc aag agt gtt cat ttc gtt gga acg gag acg tct    2400
Leu Arg Thr Pro Phe Lys Ser Val His Phe Val Gly Thr Glu Thr Ser
785                 790                 795                 800 tta gtt tgg aaa ggg tat atg gaa ggg gcc ata cga tcg ggt caa cga    2448
Leu Val Trp Lys Gly Tyr Met Glu Gly Ala Ile Arg Ser Gly Gln Arg
                805                 810                 815 ggt gct gca gaa gtt gtg gct agc ctg gtg cca gca gca tag            2490
Gly Ala Ala Glu Val Val Ala Ser Leu Val Pro Ala Ala
            820                 825
```

<210> SEQ ID NO 33
<211> LENGTH: 829
<212> TYPE: PRT
<213> ORGANISM: Unknown

<400> SEQUENCE: 33

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
```

-continued

```
                100                 105                 110
Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Glu Phe Met Ala Leu Ala Pro Ser Tyr Ile Asn Pro Pro
225                 230                 235                 240

Asn Val Ala Ser Pro Ala Gly Tyr Ser His Val Gly Val Gly Pro Asp
                245                 250                 255

Gly Gly Arg Tyr Val Thr Ile Ala Gly Gln Ile Gly Gln Asp Ala Ser
            260                 265                 270

Gly Val Thr Asp Pro Ala Tyr Glu Lys Gln Val Ala Gln Ala Phe Ala
        275                 280                 285

Asn Leu Arg Ala Cys Leu Ala Ala Val Gly Ala Thr Ser Asn Asp Val
    290                 295                 300

Thr Lys Leu Asn Tyr Tyr Ile Val Asp Tyr Ala Pro Ser Lys Leu Thr
305                 310                 315                 320

Ala Ile Gly Asp Gly Leu Lys Ala Thr Phe Ala Leu Asp Arg Leu Pro
                325                 330                 335

Pro Cys Thr Leu Val Pro Val Ser Ala Leu Ser Ser Pro Glu Tyr Leu
            340                 345                 350

Phe Glu Val Asp Ala Thr Ala Leu Val Pro Gly His Thr Thr Pro Asp
        355                 360                 365

Asn Val Ala Asp Val Val Val Gly Ala Gly Leu Ser Gly Leu Glu
    370                 375                 380

Thr Ala Arg Lys Val Gln Ala Ala Gly Leu Ser Cys Leu Val Leu Glu
385                 390                 395                 400

Ala Met Asp Arg Val Gly Gly Lys Thr Leu Ser Val Gln Ser Gly Pro
                405                 410                 415

Gly Arg Thr Thr Ile Asn Asp Leu Gly Ala Ala Trp Ile Ser Asp Ser
            420                 425                 430

Asn Gln Asn Glu Val Ser Arg Leu Phe Glu Arg Phe His Leu Glu Gly
        435                 440                 445

Glu Leu Gln Arg Thr Thr Gly Asn Ser Ile His Gln Ala Gln Asp Gly
    450                 455                 460

Thr Thr Thr Ala Pro Tyr Gly Asp Ser Leu Leu Ser Glu Glu Val
465                 470                 475                 480

Ala Ser Ala Leu Ala Glu Leu Leu Pro Val Trp Ser Gln Leu Ile Glu
                485                 490                 495

Glu His Ser Leu Gln Asp Leu Lys Ala Ser Pro Gln Ala Lys Arg Leu
            500                 505                 510

Asp Ser Val Ser Phe Ala His Tyr Cys Glu Lys Glu Leu Asn Leu Pro
        515                 520                 525
```

-continued

```
Ala Val Leu Gly Val Ala Asn Gln Ile Thr Arg Ala Leu Leu Gly Val
            530                 535                 540

Glu Ala His Glu Ile Ser Met Leu Phe Leu Thr Asp Tyr Ile Lys Ser
545                 550                 555                 560

Ala Thr Gly Leu Ser Asn Ile Phe Ser Asp Lys Lys Asp Gly Gly Gln
                565                 570                 575

Tyr Met Arg Cys Lys Thr Gly Met Gln Ser Ile Cys His Ala Met Ser
            580                 585                 590

Lys Glu Leu Val Pro Gly Ser Val His Leu Asn Thr Pro Val Ala Glu
            595                 600                 605

Ile Glu Gln Ser Ala Ser Gly Cys Thr Val Arg Ser Ala Ser Gly Ala
            610                 615                 620

Val Phe Arg Ser Lys Lys Val Val Val Ser Leu Pro Thr Thr Leu Tyr
625                 630                 635                 640

Pro Thr Leu Thr Phe Ser Pro Pro Leu Pro Ala Glu Lys Gln Ala Leu
                645                 650                 655

Ala Glu Asn Ser Ile Leu Gly Tyr Tyr Ser Lys Ile Val Phe Val Trp
                660                 665                 670

Asp Lys Pro Trp Trp Arg Glu Gln Gly Phe Ser Gly Val Leu Gln Ser
            675                 680                 685

Ser Cys Asp Pro Ile Ser Phe Ala Arg Asp Thr Ser Ile Asp Val Asp
690                 695                 700

Arg Gln Trp Ser Ile Thr Cys Phe Met Val Gly Asp Pro Gly Arg Lys
705                 710                 715                 720

Trp Ser Gln Gln Ser Lys Gln Val Arg Gln Lys Ser Val Trp Asp Gln
                725                 730                 735

Leu Arg Ala Ala Tyr Glu Asn Ala Gly Ala Gln Val Pro Glu Pro Ala
            740                 745                 750

Asn Val Leu Glu Ile Glu Trp Ser Lys Gln Gln Tyr Phe Gln Gly Ala
            755                 760                 765

Pro Ser Ala Val Tyr Gly Leu Asn Asp Leu Ile Thr Leu Gly Ser Ala
            770                 775                 780

Leu Arg Thr Pro Phe Lys Ser Val His Phe Val Gly Thr Glu Thr Ser
785                 790                 795                 800

Leu Val Trp Lys Gly Tyr Met Glu Gly Ala Ile Arg Ser Gly Gln Arg
                805                 810                 815

Gly Ala Ala Glu Val Val Ala Ser Leu Val Pro Ala Ala
            820                 825
```

AMINO POLYOL AMINE OXIDASE POLYNUCLEOTIDES AND RELATED POLYPEPTIDES AND METHODS OF USE

CROSS REFERENCE TO RELATED APPLICATION

This application claims the benefit of U.S. Provisional Application No. 60/092,936 filed Jul. 15 1998 and hereby incorporated by reference.

TECHNICAL FIELD

The present invention relates generally to the detection and isolation of fumonisin and AP1 degrading enzymes and to compositions and methods for the in vivo detoxification or degradation of fumonisin or its hydrolysis product AP1. This method has broad application in agricultural biotechnology and crop agriculture and in the improvement of food grain quality.

BACKGROUND OF THE INVENTION

Fungal diseases are common problems in crop agriculture. Many strides have been made against plant diseases as exemplified by the use of hybrid plants, pesticides and improved agricultural practices. However, as any grower or home gardener can attest, the problems of fungal plant disease continue to cause difficulties in plant cultivation. Thus, there is a continuing need for new methods and materials for solving the problems caused by fungal diseases of plants.

These problems can be met through a variety of approaches. For example, the infectious organisms can be controlled through the use of agents that are selectively biocidal for the pathogens. Another method is interference with the mechanism by which the pathogen invades the host crop plant. Yet another method, in the case of pathogens that cause crop losses, is interference with the mechanism by which the pathogen causes injury to the host crop plant. Still another method, in the case of pathogens that produce toxins that are undesirable to mammals or other animals that feed on the crop plants, is interference with toxin production, storage, or activity. This invention falls into the latter two categories.

Since their discovery and structural elucidation in 1988 (Bezuidenhout et al., Journal *Chem Soc, Chem Commun* 1988: 743–745 (1988)), fumonisins have been recognized as a potentially serious problem in maize-fed livestock. They are linked to several animal toxicoses including leukoencephalomalacia (Marasas, et al., *Onderstepoort Journal of Veterinary Research* 55: 197–204 (1988); Wilson, et al., *American Association of Veterinary Laboratory Diagnosticians: Abstracts* 33rd *Annual Meeting*, Denver, Colo., Oct. 7–9, 1990, Madison, Wis., USA) and porcine pulmonary edema (Colvin, et al., *Mycopathologia* 117: 79–82 (1992)). Fumonisins are also suspected carcinogens (Geary W (1971) *Coord Chem Rev* 7: 81; Gelderblom, et al., *Carcinogenesis* 12: 1247–1251 (1991); Gelderblom, et al., *Carcinogenesis* 13: 433–437 (1992)). Fusarium isolates in section Liseola produce fumonisins in culture at levels from 2 to >4000 ppm (Leslie, et al., *Phytopathology* 82: 341–345 (1992)). Isolates from maize (predominantly mating population A) are among the highest producers of fumonisin. (Leslie et al., supra). Fumonisin levels detected in field-grown maize have fluctuated widely depending on location and growing season, but both preharvest and postharvest surveys of field maize have indicated that the potential for high levels of fumonisins exists (Murphy, et al., *J Agr Food Chem* 41: 263–266 (1993)). Surveys of food and feed products have also detected fumonisin (Holcomb, et al., *J Agr Food Chem* 41: 764–767 (1993); Hopmans, et al., *J Agr Food Chem* 41: 1655–1658 (1993); Sydenham, et al., *J Agr Food Chem* 39: 2014–2018 (1991)). The etiology of Fusarium ear mold is poorly understood, although physical damage to the ear and certain environmental conditions can contribute to its occurrence (Nelson, *Mycopathologia* 117: 29–36 (1992)). Fusarium can be isolated from most field grown maize, even when no visible mold is present. The relationship between seedling infection and stalk and ear diseases caused by Fusarium is not clear. Genetic resistance to visible kernel mold has been identified (Gendloff, et al., *Phytopathology* 76: 684–688 (1986); Holley, et al., *Plant Dis* 73: 578–580 (1989)), but the relationship to visible mold to fumonisin production has yet to be elucidated.

Fumonisins have been shown in in vitro mammalian cell studies to inhibit sphingolipid biosynthesis through inhibition of the enzyme sphingosine N-acetyl transferase, resulting in the accumulation of the precursor sphinganine (Norred, et al., *Mycopathologia* 117: 73–78 (1992); Wang, et al., *Biol Chem* 266: 14486 (1991); Yoo, et al., *Toxicol Appl Pharmacol* 114: 9–15 (1992); Nelson, et al., *Annu Rev Phytpathol* 31:233–252 (1993)). It is likely that inhibition of this pathway accounts for at least some of fumonisin's toxicity, and support for this comes from measures of sphinganine: sphingosine ratios in animals fed purified fumonisin (Wang, et al., *J Nutr* 122: 1706–1716 (1992)). Fumonisins also affect plant cell growth (Abbas, et al., *Weed Technol* 6: 548–552 (1992); Vanasch, et al., *Phytopathology* 82: 1330–1332 (1992); Vesonder, et al., *Arch Environ Contam Toxicol* 23: 464–467 (1992)). Kuti et al., (Abstract, Annual Meeting American Phytopathological Society, Memphis, Tenn: APS Press 1993) reported on the ability of exogenously added fumonisins to accelerate disease development and increase sporulation of *Fusarium moniliforme* and *F. oxysporum* on tomato.

Enzymes that degrade the fungal toxin fumonisin to its de-esterified form (e.g. AP1 from FB1) have been identified in U.S. Pat. No. 5,716,820, issued Feb. 10, 1998 U.S. Pat. No. 5,792,931 issued Aug. 11, 1998; and pending U.S. application Ser. Nos. 08/888,950 and 08/888,949, both filed Jul. 7, 1997, and all hereby incorporated by reference. It is understood that AP1 as used here is to designate the hydrolyzed form of any fumonisin, FB1, FB2, FB3, FB4, or any other AP1-like compounds, including synthetically produced AP1 like compounds, that contain a C-2 or C-1 amine group and one or more adjacent hydroxyl groups. Plants expressing a fumonisin esterase enzyme, infected by fumonisin producing fungus, and tested for fumonisin and AP1 were found to have low levels of fumonisin but high levels of AP1. AP1 is less toxic than fumonisin to plants and probably also to animals but contamination with AP1 is still a concern. The preferred result would be complete detoxification of fumonisin to a non-toxic form. Therefore enzymes capable of degrading AP1 are necessary for the further detoxification of fumonisin. The present invention provides newly discovered polynucleotides and related polypeptides of amino polyol amine oxidase (abbreviated APAO, formerly known as AP1 catabolase, U.S. Pat. No. 5,716,820, supra; U.S. Pat. No. 5,792,931, supra, and pending U.S. applications Ser. Nos. 08/888,950 and 08/888,949, supra; trAPAO is the abbreviation for a truncated, but still functional APAO), capable of oxidatively deaminating the AP1 to a compound identified as the 2-oxo derivative of AP1 or its cyclic ketal form (abbreviated as 2-OP, formerly called AP1-N1, U.S. Pat. No. 5,716,820, supra; U.S. Pat. No. 5,792,931, supra; pending U.S. applications Ser. Nos. 08/888,950 and 08/888,949, supra), isolated from *Exophiala spinifera*, ATCC 74269. The partially purified APAO enzyme from *Exophiala spinifera* has little or no activity on intact FB1, a form of fumonisin. However, recombinant APAO enzyme from *Exophiala spinifera*, expressed in *E. coli*, has significant but reduced activity on intact FB1 and other B-series fumonisins. APAO or trAPAO thus could potentially be used without fumonisin esterase since the amine group is the major target for detoxification. Alternatively, fumoninsin esterase and APAO (or trAPAO) can be used together for degrading toxins.

APAO is a type of flavin amine oxidase (EC 1.4.3.4, enzyme class nomeclature, see *Enzyme Nomenclature* 1992, Recommendations of the Nomenclature Committee of the IUBMB on the Nomenclature and Classification of Enzymes, Academic Press, Inc. (1992)). Flavin amine oxidases are known in mammals as monoamine oxidases, where they participate in the conversion of amines involved in neuronal function. A prokaryotic flavin amine oxidase that deaminates putrescine has been described (Ishizuka et al., *J. Gen Microbiol.* 139:425–432 (1993)). A single fungal gene, from *Aspergillus niger* has been cloned (Schilling et al., *Mol Gen Genet.* 247:430–438 (1995)). It deaminates a variety of alkyl and aryl amines, but when tested for its ability to oxidize AP1, was found to not contain AP1 oxidizing activity.

The toxicity of fumonisins and their potential widespread occurrence in food and feed makes it imperative to find detoxification or elimination strategies to remove the compound from the food chain.

SUMMARY OF THE INVENTION

The present invention provides polynucleotides, related polypeptides and all conservatively modified variants of a newly discovered APAO. The nucleotide sequence of the APAO comprises the sequence found in SEQ ID NOS: 5, 10, and 22. SEQ ID NO: 5 contains the nucleotide sequence of trAPAO, SEQ ID NO: 10 contains the nucleotide sequence of trAPAO with an additional lysine and SEQ ID NO: 22 contains the full length nucleotide sequence of APAO. For expression in a plant, the nucleotide sequence of APAO or trAPAO is fused to a plant signal sequence. Preferred plant signal sequences are signal sequences which target the apoplast or a peroxisome. Other signal sequences can also be used, depending on requirements, including mitochondrial or plastidic. It is an object of the present invention to provide transgenic plants and plant cells comprising the nucleic acids of the present invention.

Therefore, in one aspect, the present invention relates to an isolated nucleic acid comprising an isolated polynucleotide sequence encoding an APAO enzyme. In a further aspect, the present invention is selected from: (a) an isolated polynucleotide encoding a polypeptide of the present invention; (b) a polynucleotide comprising at least 20 contiguous bases of the polynucleotides of the present invention; (c) a polynucleotide having at least 40% identity to a polynucleotide of the present invention; (d) a polynucleotide comprising at least 20 nucleotides in length which hybridizes under low strigency conditions to a polynucleotide of the present invention; (e) a polynucleotide comprising a polynucleotide selected from SEQ ID NOS: 5, 7, 10, 22, and 32; and (f) a polynucleotide which is complementary to the polynucleotide of (a) to (e).

Additional polynucleotides of the present invention include an APAO enzyme fused to a fumonisin esterase. The fumonisin esterase is preferably ESP1 or BEST1.

In another aspect, the present invention relates to a recombinant expression cassette comprising a nucleic acid as described, supra. Additionally, the present invention relates to a vector containing the recombinant expression cassette. Further, the vector containing the recombinant expression cassette can facilitate the transcription and translated of the nucleic acid in a host cell.

In yet another embodiment, the present invention is directed to a transgenic plant or plant cells, containing the nucleic acids of the present invention. In another embodiment, the transgenic plant is a maize plant or plant cells. In yet another embodiment are the seeds from the transgenic plant.

This invention also provides an isolated polypeptide comprising (a) a polypeptide comprising at least 25 contiguous amino acids of a polypeptide of the present invention; (b) a polypeptide comprising at least 55% sequence identity to a polypeptide of the present invention; (c) a polypeptide encoded by a nucleic acid of the present invention; (d) a polypeptide characterized by a polypeptide selected from SEQ ID NOS: 6, 11, 23, and 33; and (e) a conservatively modified variant of a polypeptide of the present invention.

Another embodiment of the subject invention comprises a method of reducing pathogenicity of a fungus producing fumonisin or a structurally related mycotoxin by transferring to a plant the nucleic acids of the present invention either by themselves or in combination with a nucleic acid coding for a fumonisin esterase. In addition, two plants, one of which is transformed with an APAO of the present invention and the other transformed with a fumonisin esterase, can be crossed to produce a plant expressing both fumonisin esterase and APAO.

This invention further provides methods of degrading a fumonisin, a fumonisin breakdown product, a structurally related mycotoxin or a breakdown product of a structurally related mycotoxin, comprising the step of reacting the mycotoxin with the degradative enzymes of the present invention. Additionally, fumonisins can be degraded by application of both fumonisin esterase enzymes and APAO enzyme. The mycotoxins can be degraded in harvested grain, during the processing of harvested grain, in animal feed, or in plant tissue as, for example, during the use of the plant for silage or as a spray on grain, fruit or vegetables.

Another embodiment of the subject invention is a host cell stably transformed by a polynucleotide construct as described above, and a method of making a polypeptide of a recombinant gene comprising:

a) providing a population of these host cells; and b) growing the population of cells under conditions whereby the polypeptide encoded by the coding sequence of the expression cassette is expressed;

c) isolating the resulting polypeptide.

A number of expression systems using the said host cells could be used, such as but not limited to, microbial, mammalian, plant, or insect. Alternatively, the fumonisin degrading enzymes can be isolated and purified from the seeds or plant parts of a plant expressing the said enzyme.

The polynucleotides of the present invention can also be used as a selectable marker for plant transformation. By transforming plant cells with an expression cassette containing the polynucleotide of the present invention and then placing the plant cells on media containing AP1 or a phytotoxic analog, only the plant cells expressing the polynucleotide of the present invention would survive.

Another embodiment of the present invention is the use of the enzyme fumonisin esterase and APAO by themselves or in combination as reagents for detecting fumonisin and structurally related toxins.

DETAILED DESCRIPTION OF THE INVENTION

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., J. H. Langenheim and K. V. Thimann, *Botany: Plant Biology and Its Relation to Human Affairs* (1982) John Wiley; *Cell Culture and Somatic Cell Genetics of Plants*, Vol. 1 (I. K. Vasil, ed. 1984); R. V. Stanier, J. L. Ingraham, M. L. Wheelis, and P. R. Painter, *The Microbial World*, (1986) 5th Ed., Prentice-Hall; O. D. Dhringra and J. B. Sinclair, *Basic Plant Pathology Methods*, (1985) CRC Press; Maniatis, Fritsch & Sambrook, *Molecular Cloning: A Laboratory Manual* (1982); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); and the series *Methods in Enzymology* (S. Colowick and N. Kaplan, eds., Academic Press, Inc.).

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

A "fumonisin-producing microbe" is any microbe capable of producing the mycotoxin fumonisin or analogs thereof. Such microbes are generally members of the fungal genus Fusarium, as well as recombinantly derived organisms, which have been genetically altered to enable them to produce fumonisin or analogs thereof.

By "degrading fumonisin" is meant any modification to fumonisin or AP1 molecule which causes a decrease or loss in its toxic activity, such as degradation to less than 1%, 5%, 10%, or 50% of original toxicity, with less than 10% being preferred. Such a change can comprise cleavage of any of the various bonds, oxidation, reduction, the addition or deletion of a chemical moiety, or any other change that affects the activity of the molecule. In a preferred embodiment, the modification includes hydrolysis of the ester linkage in the molecule as a first step and then oxidative deamination. Furthermore, chemically altered fumonisin can be isolated from cultures of microbes that produce an enzyme of this invention, such as growing the organisms on media containing radioactively-labeled fumonisin, tracing the label, and isolating the degraded toxin for further study. The degraded fumonisin can be compared to the active compound for its phytotoxicity or mammalian toxicity in known sensitive species, such as porcines, rabbits, and equines or in cell or tissue culture assays. Such toxicity assays are known in the art. For example, in plants a whole leaf bioassay can be used in which solutions of the active and inactive compound are applied to the leaves of sensitive plants. The leaves may be treated in situ or, alternatively, excised leaves may be used. The relative toxicity of the compounds can be estimated by grading the ensuing damage to the plant tissues and by measuring the size of lesions formed within a given time period. Other known assays can be performed at the cellular level, employing standard tissue culture methodologies e.g., using cell suspension cultures.

By "fumonisin esterase" is meant any enzyme capable of hydrolysis of the ester linkage in fumonisin or a structurally similar molecule such as AAL toxin. Two examples of such enzymes are ESP1 and BEST1 found in U.S. patent application Ser. No. 5,716,820, issued Feb. 10, 1998; U.S. Pat. No. 5,792,931 issued Aug. 11, 1998; and pending U.S. application Ser. Nos. 08/888,950 and 08/888,949, both filed Jul. 7, 1997.

By "structurally related mycotoxin" is meant any mycotoxin having a chemical structure related to a fumonisin or AP1 such as AAL toxin, fumonisin B1, fumonisin B2, fumonisin B3, fumonisin B4, fumonisin C2, fumonisin A1 and A2, and their analogs or hydrolyzed form, as well as other mycotoxins having similar chemical structures, including synthetically made analogs that contain a C-2 or C-1 amine group and one or more adjacent hydroxyl groups, that would be expected to be degraded by the activity of an enzyme of the present invention. The present invention is the first flavin amine oxidase known to attack a primary amine not located at C-1 (i.e. C-2 of AP1) and resulting in a keto rather than an aldehydic product.

It is understood that "AP1" or "amino polyol" as used here is to designate the hydrolyzed form of any fumonisin, FB1, FB2, FB3, FB4, AAL, or any other AP1-like compound, including a compound made synthetically, that contains a C-2 or C-1 amine group and one or more adjacent hydroxyl groups.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine, one exception is *Micrococcus rubens*, for which GTG is the methionine codon (Ishizuka, et al., *J. Gen'l Microbiol*, 139:425–432 (1993)) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90%, preferably 60–90% of the native protein for it's native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company.

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecly sulfate at 65° C.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.* (USA), 82: 2306–2309 (1985)), or the ciliate Macronucleus, may be used when the nucleic acid is expressed using these organisms.

When the nucleic acid is prepared or altered synthetically, advantage can be taken of known codon preferences of the intended host where the nucleic acid is to be expressed.

For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray et al. *Nuel. Acids Res.* 17: 477–498 (1989) and herein incorporated by reference). Thus, the maize preferred codon for a particular amino acid might be derived from known gene sequences from maize. Maize codon usage for 28 genes from maize plants is listed in Table 4 of Murray et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell, which contains a vector and supports the replication and/or expression of the expression vector. Host cells may be prokaryotic cells such as *E. coli*, or eukaryotic cells such as yeast, insect, plant, amphibian, or mammalian cells. Preferably, host cells are monocotyledonous or dicotyledonous plant cells, including but not limited to maize, sorghum, sunflower, soybean, wheat, alfalfa, rice, cotton, canola, barley, millet, and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids.

Unless otherwise stated, the term "APAO nucleic acid" means a nucleic acid comprising a polynucleotide ("APAO polynucleotide") encoding an APAO polypeptide. The term APAO, unless otherwise stated can encompass both APAO and the functional, truncated version of APAO designated trAPAO.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1–3 (1989); and *Current Protocols in Molecular Biology*, F. M. Ausubel et al., Eds., *Current Protocols*, a joint venture between Greene Publishing Associates, Inc. and John Wiley & Sons, Inc. (1994 Supplement).

As used herein "operably linked" includes reference to a functional linkage between a first sequence, such as a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants, which can be used in the methods of the invention, is generally as broad as the class of higher plants amenable to transformation techniques, including both monocotyledonous and dicotyledonous plants including species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium, and Triticum. A particularly preferred plant is *Zea mays*.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such Agrobacterium or Rhizobium. Examples are promoters that preferentially initiate transcription in certain tissues, such as leaves, roots, seeds, fibres, xylem vessels, tracheids, or sclerenchyma. Such promoters are referred to as "tissue preferred". A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions.

The term "APAO polypeptide or trAPAO polypeptide" refers to one or more amino acid sequences. The term is also inclusive of fragments, variants, homologs, alleles or precursors (e.g., preproproteins or proproteins) thereof. An "APAO or trAPAO protein" comprises an APAO or trAPAO polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60–90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g, 10 to 50 nucleotides) and at least about 60° C. for long probes (e.g, greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1× SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267–284 (1984): $T_m=81.5\,°C.+16.6\,(\log M)+0.41\,(\%\,GC)-0.61\,(\%\,form)-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, N.Y. (1995). Unless otherwise stated, in the present application high stringency is defined as hybridization in 4× SSC, 5× Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1× SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (Best Fit) of Smith and Waterman, Adv. Appl. Math may conduct optimal alignment of sequences for comparison. 2: 482 (1981); by the homology alignment algorithm (GAP) of Needleman and Wunsch, *J Mol. Biol.* 48: 443 (1970); by the search for similarity method (Tfasta and Fasta) of Pearson and Lipman, *Proc. Natl. Ai,ad. Sci.* 85: 2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994). The preferred program to use for optimal global alignment of multiple sequences is PileUp (Feng and Doolittle, *Journal of Molecular Evolution*, 25:351–360 (1987) which is similar to the method described by Higgins and Sharp, *CABIOS*, 5:151–153 (1989) and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, N.Y. (1995).

GAP uses the algorithm of Needleman and Wunsch (*J. Mol. Biol.* 48: 443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89:10915).

Unless otherwise stated, sequence identity/similarity values provided herein refer to the value obtained using the BLAST 2.0 suite of programs using default parameters. Altschul et al., *Nucleic Acids Res.* 25:3389–3402 (1997).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has between 50–100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55–100%, preferably at least 55%, preferably at least 60%, more preferably at least 70%, 80%, 90%, and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

(e) (ii) The terms "substantial identity" in the context of a peptide indicates that a peptide comprises a sequence with between 55–100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, *J. Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

Fumonisin Degrading Organisms

The present invention is based on the discovery of organisms with the ability to degrade the mycotoxin fumonisin. In a search for a biological means of detoxifying fumonisins, several dematiaceous hyphomycetes were isolated from field-grown maize kernels. The fungi were found to be capable of growing on fumonisin B1 or B2 (FB1 or FB2) as a sole carbon source, degrading it partially or completely in the process. One species, identified as *Exophiala spinifera*, a "black yeast", was recovered from maize seed from diverse locations in the southeastern and south central United States. The enzyme-active strain of *Exophiala spinifera* (ATCC 74269) was deposited (see U.S. patent application Ser. No. 5,716,820, issued Feb. 10, 1998; U.S. Pat. No. 5,792,931 issued Aug. 11, 1998; and pending U.S. application Ser. Nos. 08/888,950 and 08/888,949, both filed Jul. 7, 1997).

Nucleic Acids

The present invention provides, inter alia, isolated nucleic acids of RNA, DNA, and analogs and/or chimeras thereof, comprising an APAO or trAPAO polynucleotide.

The present invention also includes polynucleotides optimized for expression in different organisms. For example, for expression of the polynucleotide in a maize plant, the sequence can be altered to account for specific codon preferences and to alter GC content as according to Murray et al, supra. Maize codon usage for 28 genes from maize plants is listed in Table 4 of Murray, et al., supra.

The APAO or trAPAO nucleic acids of the present invention comprise isolated APAO or trAPAO polynucleotides which, are inclusive of:

(a) a polynucleotide encoding an APAO or trAPAO polypeptide of the sequences found in SEQ ID NO: 6 and 22, and conservatively modified and polymorphic variants thereof;

(b) a polynucleotide which selectively hybridizes to a polynucleotide of (a) or (b);

(c) a polynucleotide having at least 40% sequence identity with polynucleotides of (a) or (b);

(d) complementary sequences of polynucleotides of (a), (b), or (c); and (e) a polynucleotide comprising at least 15 contiguous nucleotides from a polynucleotide of (a), (b), (c), or (d).

In addition, polynucleotides are presented that are a fusion of an APAO or trAPAO polynucleotide and the polynucleotide of a fumonisin esterase. The invention encompasses the sequences from Exophiala as well as sequences having sequence similarity with such sequences. It is recognized that the sequences of the invention can be used to isolate corresponding sequences in other organisms. Methods such as PCR, hybridization, and the like can be used to identify sequences having substantial sequence similarity to the sequences of the invention. See, for example, Sambrook, et al., (1989) *Molecular Cloning: A Laboratory Manual* (2d ed., Cold Spring Harbor Laboratory Press, Planview, N.Y.) and Innis et al., (1990) *PCR Protocols: Guide to Methods and Applications* (Academic Press, N.Y.). Coding sequences isolated based on their sequence identity to the entire fumonisin degrading coding sequences set forth herein or to fragments thereof are encompassed by the present invention.

It is recognized that the sequences of the invention can be used to isolate similar sequences from other fumonisin degrading organisms. Likewise sequences from other fumonisin degrading organisms may be used in combination with the sequences of the present invention. See, for example, copending application entitled "Compositions and Methods for Fumonisin Detoxification", U.S. application Ser. No. 60/092,953, filed concurrently herewith and herein incorporated by reference.

Plasmids containing the polynucleotide sequences of the invention were deposited with American Type Culture Collection (ATCC), Manassas, Va., and assigned Accession Nos. 98812, 98813, 98814, 98815, and 98816. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. § 112.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a fungus or bacteria.

The nucleic acids may conveniently comprise sequences in addition to a polynucleotide of the present invention. For example, a multi-cloning site comprising one or more endonuclease,e restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS±, pSG5, pBK, pCR-Script, pET, pSPUTK, p3'SS, pGEM, pSK±, pGEX, pSPORTI and II, pOPRSVI CAT, pOPI3 CAT, pXT1, pSG5, pPbac, pMbac, pMC1neo, pOG44, pOG45, pFRTβGAL, pNEOβGAL, pRS403, pRS404, pRS405, pRS406, pRS413, pRS414, pRS415, pRS416, lambda MOSS1ox, and lambda MOSE1ox. Optional vectors for the present invention, include but are not limited to, lambda ZAP II, and pGEX. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.,* 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.*15:8125 (1987)) and the 5<G>7 methyl GpppG RNA cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. 96/19256. See also, Zhang, J.-H., et al. *Proc. Natl. Acad. Sci. USA* 94:4504–4509 (1997) and Zhao, et al., *Nature Biotech* 16:258–261 (1998). Generally, sequence shuffling provides a means for generating libraries of polynucleotides having a desired characteristic, which can be selected or screened for. Libraries of recombinant polynucleotides are generated from a population of related sequence polynucleotides , which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a polypeptide long enough to code for an active protein of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/ selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'- promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, the 35S promoter from cauliflower mosaic virus (CaMV), as described in Odell et al., (1985), *Nature*, 313:810–812, rice actin (McElroy et al., (1990), *Plant Cell*, 163–171); ubiquitin (Christensen et al., (1992), *Plant Mol. Biol.* 12:619–632; and Christensen, et al., (1992), *Plant Mol. Biol.* 18:675–689); pEMU (Last, et al., (1991), *Theor. Appl. Genet.* 81:581–588); MAS (Velten et al., (1984), *EMBO J* 3:2723–2730); and maize H3 histone (Lepetit et al., (1992), *Mol. Gen. Genet.* 231:276–285; and Atanassvoa et al., (1992), *Plant Journal* 2(3):291–300), ALS promoter, as described in published PCT Application WO 96/30530, and other transcription initiation regions from various plant genes known to those of skill. For the present invention ubiquitin is the preferred promoter for expression in monocot plants.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70promoter, which is inducible by heat stress, and the PPDK promoter, which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes, or alternatively from another plant gene, or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan et al., (1983), *Nucl. Acids Res.* 12:369–385); the potato proteinase inhibitor II (PINII) gene (Keil, et al., (1986), *Nucl. Acids Res.* 14:5641–5650; and An et al., (1989), *Plant Cell* 1:115–122); and the CaMV 19S gene (Mogen et al., (1990), *Plant Cell* 2:1261–1272).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., *Genes Dev.* 1:1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

Plant signal sequences, including, but not limited to, signal-peptide encoding DNA/RNA sequences which target proteins to the extracellular matrix of the plant cell (Dratewka-Kos, et al., (1989), *J. Biol. Chem.* 264:4896–4900), the *Nicotiana plumbaginifolia* extension gene (DeLoose, et al., (1991), *Gene* 99:95–100), signal peptides which target proteins to the vacuole like the sweet potato sporamin gene (Matsuka, et al., (1991), *PNAS* 88:834) and the barley lectin gene (Wilkins, et al., (1990), *Plant Cell,* 2:301–313), signal peptides which cause proteins to be secreted such as that of PRIb (Lind, et al., (1992), *Plant Mol. Biol.* 18:47–53), or the barley alpha amylase (BAA) (Rahmatullah, et al., *Plant Mol. Biol.* 12:119 (1989)) and hereby incorporated by reference), or from the present invention the signal peptide from the ESP1 or BEST1 gene, or signal peptides which target proteins to the plastids such as that of rapeseed enoyl-Acp reductase (Verwaert, et al., (1994), *Plant Mol. Biol.* 26:189–202) are useful in the invention. The barley alpha amylase signal sequence fused to the trAPAO polynucleotide (see SEQ ID NO: 20) is the preferred construct for expression in maize for the present invention.

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

Alternatively, the invention, itself, could be used as a method for selection of transformants, in other words as a selectable marker. An APAO or trAPAO polynucleotide operably linked to a promoter and then transformed into a plant cell by any of the methods described in the present application would express the degradative enzyme. When the plant cells are placed in the presence of either AP1 or a phytotoxic analog in culture only the transformed cells would be able to grow. In another embodiment, the plant cell could be transformed with both a polynucleotide for APAO and a polynucleotide for fumonisin esterase. The selective agent in this case could be either AP1 or fumonisin or any structural analog. Thus, growth of plant cells in the presence of a mycotoxin favors the survival of plant cells that have been transformed to express the coding sequence that codes for one of the enzymes of this invention and degrades the toxin. When the APAO or trAPAO cassette with or without the fumonisin esterase polynucleotide, is co-transformed with another gene of interest and then placed in the presence of fumonisin, AP1 or a phytotoxic analog, this invention would allow for selection of only those plant cells that contain the gene of interest. In the past antibiotic resistance genes have been used as selectable markers. Given the current concerns by consumers and environmentalist over use of antibiotic genes and the possibility of resistant microorganisms arising due to this use, a non-antibiotic resistant selectable marker system such as the present invention, fulfills this very important need.

Typical vectors useful for expression of genes in higher plants are well known in the art and include vectors derived from the tumor-inducing (Ti) plasmid of *Agrobacterium tumefaciens* described by Rogers et al., *Meth. In Enzymol.,* 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., Gene, 61:1 –11 (1987) and Berger et al., Proc. Natl. Acad. Sci. U.S.A., 86:8402–8406 (1989). Another useful vector herein is plasmid pBI101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level", or about 1/10 transcripts to about 1/100 transcripts to about 1/1,000 transcripts.

One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus sp.* and Salmonella (Palva, et al., *Gene* 22: 229–235 (1983); Mosbach, et al., *Nature* 302: 543–545 (1983)). The pGEX-4T-1 plasmid vector from Pharmacia is the preferred *E. coli* expression vector for the present invention.

B. Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Two widely utilized yeasts for production of eukaryotic proteins are *Saccharomyces cerevisiae* and *Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth, and Drosophila cell lines such as a Schneider cell line (See Schneider, *J. Fmbryol. Exp. Morphol.* 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach*, D. M. Glover, Ed., IRL Press, Arlington, Va. pp. 213–238 (1985).

In addition, one of the genes for fumonisin esterase or the APAO or trAPAO placed in the appropriate plant expression vector can be used to transform plant cells. The enzyme can then be isolated from plant callus or the transformed cells can be used to regenerate transgenic plants. Such transgenic plants can be harvested, and the appropriate tissues (seed or leaves, for example) can be subjected to large scale protein extraction and purification techniques, and the fumonisin degradation enzymes or APAO can be isolated for use in fumonisin and flumonisin hydrolysis product detoxification processes.

Plant Transformation Methods

Numerous methods for introducing foreign genes into plants are known and can be used to insert an APAO or trAPAO polynucleotide into a plant host, including biological and physical plant transformation protocols. See, for example, Miki et al., (1993), "Procedure for Introducing Foreign DNA into Plants", In: *Methods in Plant Molecular Biology and Biotechnology*, Glick and Thompson, eds., CRC Press, Inc., Boca Raton, pages 67–88. The methods chosen vary with the host plant, and include chemical transfection methods such as calcium phosphate, microorganism-mediated gene transfer such as Agrobacterium (Horsch, et al., (1985), *Science* 227:1229–31), electroporation, micro-injection, and biolistic bombardment.

Expression cassettes and vectors and in vitro culture methods for plant cell or tissue transformation and regeneration of plants are known and available. See, for example, Gruber, et al., (1993), "Vectors for Plant Transformation" In: *Methods in Plant Molecular Biology and Biotechnology*, Glick and Thompson, eds. CRC Press, Inc., Boca Raton, pages 89–119.

Agrobacterium-mediated Transformation

The most widely utilized method for introducing an expression vector into plants is based on the natural transformation system of Agrobacterium. *A. tumefaciens* and *A.*

*rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, for example, Kado, (1991), *Crit. Rev. Plant Sci.* 10:1. Descriptions of the Agrobacterium vector systems and methods for Agrobacterium-mediated gene transfer are provided in Gruber et al., supra; Miki, et al., supra; and Moloney et al., (1989), *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey, P. N., and Chua, N. H. (1989) *Science* 244: 174–181. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. application Ser. No. 913,914, filed Oct. 1, 1986, as referenced in U.S. Pat. No. 5,262,306, issued Nov. 16, 1993 to Robeson, et al.; and Simpson, R. B., et al. (1986) *Plant Mol. Biol.* 6: 403–415 (also referenced in the '306 patent); all incorporated by reference in their entirety.

Once constructed, these plasmids can be placed into *A. rhizogenes* or *A. tumefaciens* and these vectors used to transform cells of plant species, which are ordinarily susceptible to Fusarium or Alternaria infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g. certain members of the Liliales and Arales) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. European Patent Application Publication Number 604 662 A1 to Hiei et al. discloses a method for transforming monocots using Agrobacterium. Saito et al. discloses a method for transforming monocots with Agrobacterium using the scutellum of immature embryos (European Application 672 752 A1). Ishida et al. discusses a method for transforming maize by exposing immature embryos to *A. tumefaciens* (Ishida et al, *Nature Biotechnology*, 1996, 14:745–750).

Once transformed, these cells can be used to regenerate transgenic plants, capable of degrading fumonisin. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, E. A. (1985) *Theor. Appl. Genet.* 69:235–240; U.S. Pat. No. 4,658,082; Simpson, R. B., et al. (1986) *Plant Mol. Biol.* 6: 403–415; and U.S. patent applications Ser. Nos. 913,913 and 913,914, both filed Oct. 1, 1986, as referenced in U.S. Pat. No. 5,262,306, issued Nov. 16, 1993 to Robeson, et al.; the entire disclosures therein incorporated herein by reference.

Direct Gene Transfer

Despite the fact that the host range for Agrobacterium-mediated transformation is broad, some major cereal crop species and gymnosperms have generally been recalcitrant to this mode of gene transfer, even though some success has recently been achieved in rice (Hiei et al., (1994), *The Plant Journal* 6:271–282). Several methods of plant transformation, collectively referred to as direct gene transfer, have been developed as an alternative to Agrobacterium-mediated transformation.

A generally applicable method of plant transformation is microprojectile-mediated transformation, where DNA is carried on the surface of microprojectiles measuring about 1 to 4 $\mu$m. The expression vector is introduced into plant tissues with a biolistic device that accelerates the microprojectiles to speeds of 300 to 600 m/s which is sufficient to penetrate the plant cell walls and membranes. (Sanford et al., (1987), *Part. Sci. Technol.* 5:27; Sanford, 1988*, Trends Biotech* 6:299; Sanford, (1990), *Physiol. Plant* 79:206; Klein et al., (1992), *Biotechnology* 10:268).

Another method for physical delivery of DNA to plants is sonication of target cells as described in Zang et al., (1991), *BioTechnology* 9:996. Alternatively, liposome or spheroplast fusions have been used to introduce expression vectors into plants. See, for example, Deshayes et al., (1985), *EMBO J.* 4:2731; and Christou et al., (1987), *PNAS USA* 84:3962. Direct uptake of DNA into protoplasts using $CaCl_2$ precipitation, polyvinyl alcohol, or poly-L-ornithine has also been reported. See, for example, Hain et al., (1985), i Mol. Gen. Genet. 199:161; and Draper et al., (1982), *Plant Cell Physiol.* 23:451.

Electroporation of protoplasts and whole cells and tissues has also been described. See, for example, Donn et al., (1990), In: *Abstracts of the VIIth Int'l. Congress on Plant Cell and Tissue Culture IAPTC*, A2–38, page 53; D'Halluin et al., (1992), *Plant Cell* 4:1495–1505; and Spencer et al., (1994), *Plant Mol. Biol.* 24:51–61.

Thus, polynucleotide encoding a polypeptide able to inactivate fumonisin or AP1 can be isolated and cloned in an appropriate vector and inserted into an organism normally sensitive to the Fusarium or its toxins. Furthermore, the polynucleotide imparting fumonisin or AP1 degradative activity can be transferred into a suitable plasmid, and transformed into a plant. Thus, a fumonisin or AP1 degrading transgenic plant can be produced. Organisms expressing the polynucleotide can be easily identified by their ability to degrade fumonisin or AP1. The protein capable of degrading fumonisin or AP1 can be isolated and characterized using techniques well known in the art.

APAO or trAPAO in a Transgenic Plant

Fumonisin esterase reduces but does not eliminate the toxicity of fumonisins. Therefore a second enzymatic modification to further reduce or abolish toxicity is desirable. The partially purified APAO enzyme from Exophiala spinifera has little or no activity on intact FB1, a form of fumonisin. However, recombinant APAO enzyme from Exophiala spinifera, expressed in E. coli, has significant but reduced activity on intact FB1 and other B-series fumonisins. APAO or trAPAO thus could potentially be used without fumonisin esterase since the amine group is the major target for detoxification. Alternatively, the two genes, fumoninsin esterase and APAO (or trAPAO) can be used together for degrading toxins.

APAO is predicted to be an enzyme that, when by itself or co-expressed in a heterologous expression system along with fumonisin esterase (either ESP1 or BEST1), will result in the production of 2-oxo pentol (2-OP) from fumonisin B1. The substrate range of recombinant, E. coli-expressed APAO is limited to fumonisins and their hydrolysis products and does not include amino acids, sphingolipid precursors such as phytosphingosine, or polyamines such as spermidine. Thus, APAO is highly specific for fumonisin-like amines, and thus would have little deleterious effect on other cellular metabolites. In addition, if it is extracellularly localized, it will limit any contact with biologically important amines that might also be substrates. The end result will be a more effective detoxification of fumonisins than can be achieved with esterase alone.

The oxidase activity of APAO is predicted to result in generation of hydrogen peroxide in stoichiometric amounts relative to AP1 or fumonisin oxidized. This may prove to be an additional benefit of this enzyme, since hydrogen peroxide is both antimicrobial and is thought to contribute to the onset of a defense response in plants (Przemylaw, *Biochem J*, 322:681–692 (1997), Lamb, et al, *Ann Rev Plant Physiol Plant Mol Bio* 48:251–275 (1997), and Alverez, et al., *Oxidative Stress and the Molecular Biology of Antioxidant Defenses*, Cold Spring Harbor Press, 815–839 (1997)).

Since one of the preferred embodiments of the present invention is to have both a fumonisin esterase polynucleotide and an APAO or trAPAO polynucleotide present in a plant, there are several ways to introduce more than one polynucleotide in a plant. One way is to transform plant tissue with polynucleotides to both fumonisin esterase and APAO or trAPAO at the same time. In some tissue culture systems it is possible to transform callus with one polynucleotide and then after establishing a stable culture line containing the first polynucleotide, transform the callus a second time with the second polynucleotide. One could also transform plant tissue with one polynucleotide, regenerate whole plants, then transform the second polynucleotide into plant tissue and regenerate whole plants. The final step would then be to cross a plant containing the first polynucleotide with a plant containing the second polynucleotide and select for progeny containing both polynucleotides.

Another method is to create a fusion protein between esterase and APAO or trAPAO, preferably with a spacer region between the two polypeptides. Both enzymes would be active although tethered to each other. In addition, an enzyme cleavage site engineered in the spacer region, would allow cleavage by an endogenous or introduced protease. Transgenic plants containing both a fumonisin esterase enzyme and/or the APAO enzyme and thus able to degrade fumonisin or a structurally related mycotoxin would be able to reduce or eliminate the pathogenicity of any microorganism that uses fumonisin or a structurally related mycotoxin as a mode of entry to infect a plant. Fungal pathogens frequently use toxins to damage plants and weaken cell integrity in order to gain entry and expand infection in a plant. By preventing the damage induced by a toxin, a plant would be able to prevent the establishment of the pathogen and thereby become tolerant or resistant to the pathogen.

Another benefit of fumonisin degradation is the production of hydrogen peroxide. When fumonisin is broken down to 2-OP, hydrogen peroxide is produced as a by-product. Hydrogen peroxide production can trigger enhanced resistance responses in a number of ways. 1) Hydrogen peroxide has direct antimicrobial activity. 2) Hydrogen peroxide acts as a substrate for peroxidases associated with lignin polymerization and hence cell wall strengthening. 3) Via still to be determined mechanisms, hydrogen peroxide acts as a signal for activation of expression of defense related genes, including those that result in stimulation of salicylic acid accumulation. Salicylic acid is thought to act an endogenous signal molecule that triggers expression of genes coding for several classes of pathogenesis-related proteins. Moreover, salicylic acid may set up the oxidative burst and thus act in a feedback loop enhancing its own synthesis. Salicylic acid may also be involved in hypersensitive cell death by acting as an inhibitor of catalase, an enzyme that removes hydrogen peroxide. 4) Hydrogen peroxide may trigger production of additional defense compounds such as phytoalexins, antimicrobial low molecular weight compounds. For a review on the role of the oxidative burst and salicylic acid please see Lamb, C. and Dixon, R. A., *Ann. Rev. Plant Physiol. Plant Mol. Biol.*, 48: 251–275 (1997).

Detoxification of Harvested Grain, Silage, or Contaminated Food Crop

The present invention also relates to a method of detoxifying a fumonisin or a structurally related mycotoxin with the APAO enzyme from by *Exophiala spinifera*, ATCC 74269 during the processing of grain for animal or human food consumption, during the processing of plant material for silage, or food crops contaminated with a toxin producing microbe, such as but not limited to, tomato. Since the atmospheric ammoniation of corn has proven to be an ineffective method of detoxification (see B. Fitch Haumann, *INFORM* 6:248–257 (1995)), such a methodology during processing is particularly critical where transgenic detoxification is not applicable.

In one embodiment of the present invention, fumonisin degradative enzymes are presented to grain, plant material for silage, or a contaminated food crop, or during the processing procedure, at the appropriate stages of the procedure and in amounts effective for detoxification of fumonisins and structurally related mycotoxins. Detoxification by the enzymes, the microbial strains, or an engineered microorganism can occur not only during the processing, but also any time prior or during the feeding of the grain or plant material to an animal or incorporation of the grain or food crop into a human food product, or before or during ingestion of the food crop.

Another embodiment of the present invention is the engineering of a bacterium or fungus to express the detoxification enzymes and then using the bacterium or fungus rather than the enzyme itself. There are a number of microbes that could be engineered to express the polynucleotides of the present invention. One could also activate, either inducibly or constitutively, the endogenous genes for fumonisin esterase or APAO of Exophiala. By overexpressing the degradative enzymes and then treating plants, seed, or silage with the microorganism, it would be possible to degrade fumonisin in situ.

The polynucleotides of the invention can be introduced into microorganisms that multiply on plants (epiphytes) to deliver enzymes to potential target crops. Epiphytes can be gram-positive or gram-negative bacteria, for example.

The microorganisms that have been genetically altered to contain at least one degradative polynucleotide and resulting polypeptide may be used for protecting agricultural crops and products. In one aspect of the invention, whole, i.e. unlysed, cells of the transformed organism are treated with reagents that prolong the activity of the enzyme produced in the cell when the cell is applied to the environment of a target plant. A secretion leader may be used in combination with the gene of interest such that the resulting enzyme is secreted outside the host cell for presentation to the target plant.

The degradative enzymes can be fermented in a bacterial host and the resulting bacteria processed and used as a microbial spray. Any suitable microorganism can be used for this purpose. See, for example, Gaertner, et al. (1993) in *Advanced Engineered Pesticides*, (ed. Kim, Marcel Dekker, N.Y.).

The enzymes or microorganisms can be introduced during processing in appropriate manners, for example as a wash or spray, or in dried or lyophilized form or powered form, depending upon the nature of the milling process and/or the stage of processing at which the enzymatic treatment is carried out. See generally, Hoseney, R. C., *Principles of Cereal Science and Technology*, American Assn. of Cereal Chemists, Inc., 1990 (especially Chapters 5, 6 and 7); Jones, J. M., *Food Safety*, Eagan Press, St. Paul, Minn., 1992 (especially Chapters 7 and 9); and Jelen, P., *Introduction to Food Processing*, Restan Publ. Co., Reston, Va., 1985. Processed grain or silage to be used for animal feed can be treated with an effective amount of the enzymes in the form of an inoculant or probiotic additive, for example, or in any form recognized by those skilled in the art for use in animal feed. The enzymes of the present invention are expected to be particularly useful in detoxification during processing and/or in animal feed prior to its use, since the enzymes display relatively broad ranges of pH activity. The esterase from *Exophiala spinifera*, ATCC 74269, showed a range of activity from about pH 3 to about pH 6, and the esterase from the bacterium of ATCC 55552 showed a range of activity from about pH 6 to about pH 9 (U.S. Pat. No. 5,716,820, supra). The APAO enzyme from *Exophiala spinifera* (ATCC 74269) has a pH range of activity from pH 6 to pH 9.

Genetic Engineering of Ruminant Microorganisms

Ruminant microorganisms can be genetically engineered to contain and express either the fumonisin esterase enzymes or APAO isolated from *Exophiala spinifera*, ATCC 74269, or a combination of the enzymes. The genetic engineering of microorganisms is now an art recognized technique, and ruminant microorganisms so engineered can be added to feed in any art recognized manner, for example as a probiotic or inoculant. In addition, microorganisms capable of functioning as bioreactors can be engineered so as to be capable of mass producing either the fumonisin esterases or the APAO enzyme found in *Exophiala spinifera*, ATCC 74269.

Use of the Fumonisin Esterase and APAO Enzymes for Detection of Reagents for Fumonisins and Related Compounds Another embodiment of the present invention is the use of the enzymes of the present invention as detection reagents for fumonisins and related compounds. The enzymes of the present invention can be used as detection reagents because of the high specificity of the esterase and deaminase enzymes, and the fact that hydrolysis followed by amine oxidation can be monitored by detection of hydrogen peroxide or ammonia using standard reagents (analogous to a glucose detection assay using glucose oxidase). Hydrogen peroxide is often measured by linking a hydrogen peroxide-dependent peroxidase reaction to a colored or otherwise detectable peroxidase product (e.g. Demmano, et al., *European Journal of Biochemistry* 238(3): 785–789 (1996)). Ammonia can be measured using ion-specific electrodes: Fritsche, et al., *Analytica Chimica Acta* 244(2): 179–182 (1991); West, et al., *Analytical Chemistry* 64(5): 533–540 (1992), and all herein incorporated by reference) or by GC or other chromatographic method.

For example, recombinant or non-recombinant, active fumonisin esterase (ESP1 or BEST) and APAO proteins are added in catalytic amounts to a sample tube containing an unknown amount of fumonisins (FB1, FB2, FB3, FB4, or partial or complete hydrolysis products of these). The tube is incubated under pH and temperature conditions sufficient to convert any fumonisin in the sample to AP1, and correspondingly the AP1 to 2-OP, ammonia, and hydrogen peroxide. Then suitable reagents are added for quantification of the hydrogen peroxide or ammonia that were generated stoichiometrically from fumonisins. By comparison with control tubes that received no esterase or APAO enzyme, the amount of fumonisin present can be calculated in direct molar proportion to the hydrogen peroxide or ammonia detected, relative to a standard curve.

This invention can be better understood by reference to the following non-limiting examples. It will be appreciated by those skilled in the art that other embodiments of the invention may be practiced without departing from the spirit and the scope of the invention as herein disclosed and claimed.

EXAMPLE 1

Fungal and Bacterial Isolates

Exophiala isolates from maize were isolated as described in U.S. Pat. No. 5,716,820, issued Feb. 10, 1998 and pending U.S. applications Ser. Nos. 08/888,950 and 08/888,949, both filed Jul. 7, 1997, and herein incorporated by reference.

Isolation Methods

Direct isolation of black yeasts from seed was accomplished by plating 100 microliters of seed wash fluid onto YPD or Sabouraud agar augmented with cycloheximide (500 mg/liter) and chloramphenicol (50 mg/liter). Plates were incubated at room temperature for 7–14 days, and individual pigmented colonies that arose were counted and cultured for analysis of fumonisin-degrading ability as described in U.S. Pat. No. 5,716,820, issued Feb. 10, 1998 and pending U.S. application Ser. Nos. 08/888,950 and 08/888,949, both filed Jul. 7, 1997.

Analysis of Fumonisins and Metabolism Products

Analytical thin-layer chromatography was carried out on 100% silanized C18 silica plates (Sigma #T-7020; 10×10 cm; 0.1 mm thick) by a modification of the published method of Rottinghaus (Rottinghaus, et al., *J Vet Diagn Invest*, 4: 326 (1992), and herein incorporated by reference).

To analyze fumonisin esterase activity sample lanes were pre-wet with methanol to facilitate sample application. After application of from 0.1 to 2 μl of aqueous sample, the plates were air-dried and developed in MeOH:4% KCl (3:2) or MeOH:0.2 M KOH (3:2) and then sprayed successively with 0.1 M sodium borate (pH 9.5) and fluorescamine (0.4 mg/ml in acetonitrile). Plates were air-dried and viewed under long wave UV.

For analysis of APAO activity, an alternative method was used. Equal volumes of sample and $^{14}$C-AP1 (1 mg/ml, pH 8, 50 mM sodium phosphate) were incubated at room temperature for one to six days. Analytical thin-layer chromatography was then carried out on C60 HPK silica gel plates (Whatman #4807–700; 10×10 cm; 0.2 mm thick). After application of from 0.1 to 2 μl of aqueous sample, the plates were air-dried and developed in $CHCl_3$:MeOH:$CH_3COOH$:$H_2O$ (55:36:8:1). Plates were then air dried, and exposed to PhosphorImager screen (Molecular Dynamics) or autoradiographic film. A Storm™ PhosphorImager (Molecular Dynamics) was used to scan the image produced on the screen.

Alkaline Hydrolysis of FB1 to AP1

FB1 or crude fumonisin $C_8$ material was suspended in water at 10–100 mg/ml and added to an equal volume of 4 N NaOH in a screw-cap tube. The tube was sealed and incubated at 60° C. for 1 hr. The hydrolysate was cooled to RT and mixed with an equal volume of ethyl acetate, centrifuged at 1000 RCF for 5 minute and the organic (upper) layer recovered. The pooled ethyl acetate layers from two successive extractions were dried under $N_2$ and resuspended in distilled $H_2O$. The resulting material (the aminopentol of FB1 or "AP1") was analyzed by TLC.

Enzyme Activity of Culture Filtrate and Mycelium

*Exophiala spinifera* isolate 2141.10 was grown on YPD agar for 1 week, and conidia were harvested, suspended in sterile water, and used at 105 conidia per ml to inoculate sterile Fries mineral salts medium containing 1 mg/ml purified FB1 (Sigma Chemical Co.). After 2 weeks incubation at 28° C. in the dark, cultures were filtered through 0.45 micron cellulose acetate filters, and rinsed with Fries mineral salts. Fungal mycelium was suspended in 15 mL of 0.1% FB1, pH 5.2+1 mM EDTA+3 μg/mL Pepstatin A+1.5 μg/mL Leupeptin and disrupted in a Bead Beater™ using 0.1 mm beads and one minute pulses, with ice cooling. Hyphal pieces were collected by filtering through Spin X™ (0.22 μm), and both mycelial supernatant and original culture filtrates were assayed for fumonisin modification by methods outlined above.

Preparation of Crude Culture Filtrate

Agar cultures grown as above were used to inoculate YPD broth cultures (500 ml) in conical flasks at a final concentration of 105 conidia per ml culture. Cultures were incubated 5 days at 28° C. without agitation and mycelia harvested by filtration through 0.45 micron filters under vacuum. The filtrate was discarded and the mycelial mat was washed and resuspended in sterile carbon-free, low mineral salts medium (1 g/liter $NH_3NO_4$; 1 g/liter $NaH_2PO_4$; 0.5 g/liter $MgCl_2$; 0.1 g/liter NaCl; 0.13 g/liter $CaCl_2$; 0.02 g/liter $FeSO_4.7H_2O$, pH 4.5) containing 0.5 mg/ml alkaline hydrolyzed crude FB1. After 3–5 days at 28° C. in the dark with no agitation the cultures were filtered through low protein binding 0.45 micron filters to recover the culture filtrate. Phenylmethyl sulfonyl fluoride (PMSF) was added to a concentration of 2.5 mM and the culture filtrate was concentrated using an Amicon™ YM10 membrane in a stirred cell at room temperature, and resuspended in 50 mM sodium acetate, pH 5.2 containing 10 mM $CaCl_2$. The crude culture filtrate (approx. 200-fold concentrated) was stored at −20° C.

To obtain preparative amounts of enzyme-hydrolyzed fumonisin, 10 mg. of FB1 (Sigma) was dissolved in 20 mL of 50 mM sodium acetate at pH 5.2+10 mM $CaCl_2$, and 0.25 mL of 200×concentrated crude culture filtrate of 2141.10 was added. The solution was incubated at 37° C. for 14 hours, and then cooled to room temperature. The reaction mixture was brought to approx. pH 9.5 by addition of 0.4 mL of 4 N KOH, and the mixture was extracted twice with 10 mL ethyl acetate. The combined organic layers were dried under $N_2$ and resuspended in d$H_2O$. 2.5 milligrams of organic extracted material were analyzed by Fast Atom Bombardment (FAB) mass spectrometry. The resulting mass spectrum showed a major ion at M/z (+1)=406 mass units, indicating the major product of enzymatic hydrolysis was AP1 which has a calculated molecular weight of 405.

EXAMPLE 2

Preparation of AP1-induced and Non-induced Mycelium

Liquid cultures of *Exophiala spinifera* isolate 2141.10 were prepared from YPD agar plates (Yeast Extract 10 gm, Bacto-Peptone 20 gm, Dextrose 0.5 gm, and Bacto-Agar 15 gm per liter of water). Aliquots (400–500 uL) of a water suspension of *E. spinifera* cells from YPD agar were spread uniformly onto 150×15 mm YPD agar plates with 4 mm sterile glass beads. The plates were incubated at room temperature for 6–7 days. The mycelia/conidia were transferred from the agar plates into Mineral Salts Medium (MSM) ($Na_2HPO_4 7H_2O$ 0.2 gm, $NH_4Cl$ 1.0 gm, $CaCl_2 2H_2O$ 0.01 gm, $FeSO_4 7H_2O$ 0.02 gm per liter of distilled water, pH 4.5) and centrifuged at 5000× g, 4° C., 20 minutes to pellet the cells. The cell pellet was rinsed once in 40 mL MSM and recentrifuged. The rinsed cell pellet was used to inoculate MSM at a 1:19 ratio of packed cells: MSM. The culture to be induced was supplemented with AP1 to a final concentration of 0.5–1.0 mg/ml and incubated at 28° C., 100 rpm, in the dark to induce catabolic enzymes. The non-induced cultures did not receive AP1 but were place on media containing 4-ABA at the same concentration as AP1. The supernatants were removed by filtration through 0.45 cellulose acetate. The remaining mycelial mat was washed with sterile MSM and then frozen in liquid nitrogen for storage.

EXAMPLE 3

Effect of FB1 and AP1on Maize Coleoptiles

Maize coleoptiles from 4 day dark-grown germinated maize seeds were excised above the growing point and placed in 96-well microtiter plates in the presence of 60 microliters of sterile distilled water containing FB1 or AP1 at approximately equimolar concentrations of 1.5, .5, .15, .05, .015, .005, .0015, or .0005 millimolar, along with water controls. After 2 days in the dark at 28° C. the coleoptiles were placed in the light and incubated another 3 days. Injury or lack thereof was evaluated as follows:

|     | 0 | .0005 | .0015 | .005 | .015 | .05 | .15 | .5 | 1.5 | mM |
|-----|---|-------|-------|------|------|-----|-----|----|-----|----|
| FB1 | − | −     | −     | −    | +/−  | +   | +   | +  | +   |    |
| AP1 | − | −     | −     | −    | −    | −   | −   | −  | +   |    |

+ = brown necrotic discoloration of coleoptile
− = no symptoms (same as water control)

The results indicate there is at least a 30-fold difference in toxicity between FB1 and AP1 to maize coleoptiles of this genotype. This is in general agreement with other studies where the toxicity of the two compounds was compared for plant tissues: In Lemna tissues, AP1 was approx. 40-fold less toxic (Vesonder et al.," *Arch Environ Contam Toxicol* 23: 464–467 (1992).). Studies with both AAL toxin and FB1 in tomato also indicate the hydrolyzed version of the molecule is much less toxic (Gilchrist et al., *Mycopathologia* 117: 57–64 (1992)). Lamprecht et al. also observed an approximate 100-fold reduction in toxicity to tomato by AP1 versus FB1 (Lamprecht et al., *Phytopathology* 84:383391 (1994)).

EXAMPLE 4

Effect of FB1 and AP1 on Maize Tissue Cultured Cells (Black Mexican Sweet, BMS)

FB1 or AP1 at various concentrations was added to suspensions of BMS cells growing in liquid culture medium in 96-well polystyrene plates. After 1 week the cell density in wells was observed under low power magnification and growth of toxin-treated wells was compared to control wells that received water. Growth of BMS cells was significantly inhibited at 0.4 micromolar FB1, but no inhibition was observed until 40 micromolar AP 1. This represents an approximate 100-fold difference in toxicity to maize tissue cultured cells. Similarly Van Asch et al. (VanAsch et al., *Phytopathology* 82: 1330–1332 (1992)) observed significant inhibition of maize callus grown on solid medium at 1.4 micromolar FB 1. AP1 was not tested in that study, however.

EXAMPLE 5

APAO Activity

A cell-free extract that contains the amine oxidase activity was obtained by subjecting substrate-induced *Exophiala spinifera* cells to disruption using a Bead Beater™ in 50 mM Na-phosphate, pH 8.0, and recovering the cell-free supernatant by centrifugation and 0.45 micron filtration. Catabolic activity is assayed by incubating extracts with AP1 (hydrolyzed fumonisin B1 backbone) or $^{14}$C-labelled AP1 with the extract and evaluating by TLC on C18 or C60 silica. The product 2-OP has a lower Rf than AP 1 and is detected either by radiolabel scan or by $H_2S0_4$ spray/charring of the TLC plate. 2-OP does not react with the amine reagent fluorescamine that is routinely used to detect AP1 on TLC plates, suggesting that the amine group is missing or chemically modified. Activity is greater at 37° C. than at room temperature, but following 30 min. at 65° C. or 100° C. no AP1 catabolic activity remained. Activity is maximal at pH 9. At pH 9, complete conversion to 2-OP occurred in 30 minutes. Activity is retained by 30,000 dalton molecular weight cutoff membrane, but only partially retained by 100,000 dalton molecular weight cutoff membrane. Other amine-containing substrates were tested for modification by the crude extract. Fumonisin (with tricarballylic acids attached) is not modified by the extract, indicating that ester-hydrolysis must occur first for the APAO to be able to be effective in modifying FB 1. Other long-chain bases (sphingosine, sphinganine, and phytosphingosine) are apparently not modified by the crude APAO, suggesting the enzyme(s) is specific for the fumonisin backbone. Preparative amounts of the product, named 2-OP, have also been purified and analyzed by C13 nmr. The results indicate that 2-OP has a keto group at carbon 2 instead of an amine, consistent with an oxidative deamination by an amine oxidase. The C13 -nmr data also indicate that 2-OP spontaneously forms an internal hemiketal between C-1 and C-5, resulting in a 5-membered ring with a new chiral center at C-2. All other carbon assignments are as in AP1, thus 2-OP is a compound of composition $C_{22}H_{44}O_6$, FW 404. The product of the enzyme acting on hydrolyzed fumonisin would not be expected to display any significant toxicity.

Other enzymes were tested for their ability to modify AP1. All enzymes were assayed by radiolabeled TLC, as described above, under optimal conditions at 37° Celsius, overnight or longer. The results are as follows:

| Deaminating | EC | Source | Result |
|---|---|---|---|
| Monoamine Oxidase | 1.4.3.4 | bovine plasma | negative |
| D-amino oxidase | 1.4.3.3 | porcine kidney; TypeX | negative |

-continued

| Deaminating | EC | Source | Result |
|---|---|---|---|
| L-amino oxidase | 1.4.3.2 | C. adamanteus venom; TypeI | negative |
| Tyramine oxidase | 1.4.3.4 | Arthrobacter spp | negative |
| Methylamine dehydrogenase | 1.4.99.3 | Paracoccus denitrificans | negative |
| Aralkyl amine dehydrogenase | 1.4.99.4 | Alcaligenes faecalis | negative |
| Phenylalanine ammonia lyase | 4.3.1.5 | Rhodotorula glutinis; TypeI | negative |
| Histidine ammonia lyase | 4.3.1.3 | Pseudomonas fluorescens | negative |
| L-aspartase | 4.3.1.1 | Hafnia alvei (Bacterium cadaveris) | negative |
| Tyrosine oxidase | 1.14.18.1 | mushroom | negative |
| Lysine oxidase | 1.4.3.14 | Trichoderma viride | negative |
| Diamine oxidase | 1.4.3.6 | porcine kidney | negative |

The results were negative for each enzyme tested. Therefore isolates from the American Type Culture Collection (ATCC) were collected. The ATCC isolates selected were listed as containing amine-modifying enzymes or were capable of growth/utilization on amine-containing substrates. The isolates were tested to determine if they could grow on or utilize AP1 as the sole nitrogen source and if any could modify AP1 to a new compound(s). The nitrogen sources that were used in liquid cultures were AP1 0.1% (w/v), s-butylamine 0.1% (v/v), n-butylamine 0.1% (v/v), and ammonium nitrate 0.2% (w/v). These were prepared in Vogel's Minimal Media (without $NH_4NO_3$) containing 2% sucrose. The isolates were inoculated into the various media and monitored for growth over 2–3 weeks. They were also assayed with the $^{14}C$-radiolabeled TLC assay for AP1 modification. In summary, none of the isolates tested exhibited modification of AP1 in vivo. Clearly the APAO enzyme from *Exophiala spinifera* is unique and unusual in its ability to modify the AP1 toxin.

EXAMPLE 6

Isolation of the trAPAO Polynucleotide

The trAPAO polynucleotide was identified using a proprietary transcript imaging method that compares transcript patterns in two samples and allows cloning of differentially expressed fragments. This technology was developed by CuraGen® (New Haven, Conn.). (see Published PCT patent application No. WO 97/15690, published May 1, 1997, and hereby incorporated by reference) Fluorescently-tagged, PCR amplified cDNA fragments representing expressed transcripts can be visualized as bands or peaks on a gel tracing, and the cDNA from differentially expressed (induced or suppressed) bands can be recovered from a duplicate gel, cloned and sequenced. Known cDNAs can be identified without the need for cloning, by matching the predicted size and partially known sequence of specific bands on the tracing.

In the present invention two RNA samples were obtained from cultures of *E. spinifera* grown for a specified period in a mineral salts medium containing either AP1 (induced condition), or gamma-aminobutyric acid (ABA; non-induced condition) as a sole carbon source. In the induced condition, fumonisin esterase and APAO enzyme activities are detected, whereas in the non-induced condition these activities are not detected. The methods used for induction of APAO and detection of activity are described earlier (see Example 2 and Example 5). RNA was extracted from induced mycelium by Tri-Reagent methods (Molecular Research Center Inc., Cincinnati, Ohio) only grinding a frozen slurry of tissue and Tri-Reagent with a mortar and pestle until almost melted and adding an additional extraction after the phase separation by extracting the aqueous phase one time with phenol, and two times with a phenol:chloroform:isoamyl alcohol mixture. The RNA's were submitted for CuraGeng® transcript imaging to detect cDNA fragments that are induced specifically in the presence AP1. In the resulting gel tracing several bands were found which showed induction of at least 2-fold up to 79-fold or even 100-fold or more in AP1. In the resulting gel tracing several bands were found which showed induction of at least 10-fold in AP1-grown cells as compared to cells grown in ABA. The sequence of two highly induced bands can be found in Table 1.

TABLE 1

Nucleotide sequence of two CuraGen ® bands that were identified as strongly induced by AP1 in cultures of Exophiala spinifera.

>k0n0-395.5_b (SEQ ID NO: 1)

GGGCCCCGGCGTTCTCGTAGGCTGCGCGGAGTTGGTCCCAGACAGACTTTTGTCGTACCTGCTTG

GACTGTTGGGACCACTTCCGTCCCGGGTCTCCGACCATGAAACAGGTAATGGACCATTGTCGAT

CGACGTCGATGCTGGTATCTCTGGCAAATGAGATGGGGTCACAGCTCGATTGGAGGACGCCCGA

GAAGCCTTGTTCGCGCCACCACGGCTTGTCCCATACGAAGACTATCTTGCTATAGTAGCCCAGG

ATAGAATTTTCCGCCAATGCTTGCTTCTCGGCGGGAAGAGGTGGTGAAAATGTCAAGGTGGGAT

ACAAGGTTGTCGGTAACGAAACCANCACCTTTTTGCTTCGGAACACGGCGC

TABLE 1-continued

Nucleotide sequence of two CuraGen ® bands that were identified as strongly induced by AP1 in cultures of Exophiala spinifera.

>r0c0-182.3_6(SEQ ID NO: 2)

GAATTTTCCGCCAATGCTTGCTTCTCGGCGGGAAGAGGTGGTGAAAATGTCAAGGTGGGATACA

AGGTTGTCGGTAACGAAACCACCACCTTTTTGCTTCGGAACACGGCGCCCGAGGCCGATCGTAC

TGTACAGCCGGATGCCGACTGCTCAATTTCAGCGACGGGGGTGTTGAGGTGCAC

Two of the highly induced bands, k0n0-395.5, and r0c0-182.3 showed significant sequence homology to a family of enzymes, flavin-containing amine oxidases (EC 1.4.3.4), that oxidize primary amines to an aldehyde or ketone, releasing ammonia and hydrogen peroxide (Table 2).

TABLE 2

Identification of a putative flavin amine oxidase from E. spinifera: AP1-induced transcript fragments with amine oxidase homology. BLAST 2.0 default parameters.

| Clone ID | Size | Best Hit | Best Hit Name, source | Prob | from | to | Likely function |
|---|---|---|---|---|---|---|---|
| k0n0-395.5 | 395 bp | P40974 | putrescine oxidase, Micrococcus rubens, EC 1.4.3.10 Length = 478 | 8.0 e-07 | 276 | 333 | oxidation of C-2 amine of AP1 |
| r0c0-182.3 (contigs with k0n0-395) | 182 bp | P12398 | monoamine oxidase type A (MAO-A) [Bos taurus] Length = 527 | 0.0039 | 238 | 296 | oxidation of C-2 amine of AP1 |

The chemical structure of the primary product of AP1 deamination is thought to be a 2-keto compound which cyclizes to a hemiketal at carbons 2 and 5. Therefore it is predicted that this induced enzyme is responsible for deamination of AP1.

Using sequence derived from k0n0-395.5, a partial cDNA was obtained by 3' and 5' RACE-PCR (Chenchik, et al., CLONTECHniques X 1:5–8 (1995); Chenchik, et al., A new method for full-length cDNA cloning by PCR. In A Laboratory Guide to RNA: Isolation, Analysis, and Synthesis. Ed. Krieg, P. A. (Wiley-Liss, Inc.), 273–321 (1996)). A RACE cloning kit from CLONTECH was used, to obtain the RACE amplicons. Briefly, poly A+ RNA is transcribed to make first strand cDNA using a "lock-docking" poly T, cDNA synthesis primer, the second strand is synthesized and the Marathon cDNA adaptor is ligated to both ends of the ds cDNA. Diluted template is then used with the Marathon adapter primer and in separate reactions either a 5' Gene Specific Primer (GSP) or a 3'GSP is used to produce the 3' or 5' RACE amplicon. After characterization of the RACE product(s) and sequencing, full-length cDNAs may be generated by 1) end-to-end PCR using distal 5' and 3' GSPs with the adapter-ligated ds cDNA as template, or 2) the cloned 5' and 3'-RACE fragments may be digested with a restriction enzyme that cuts uniquely in the region of overlap, the fragments isolated and ligated. Subsequently, the RACE-generated full-length cDNAs from 1) and 2) may be cloned into a suitable vector.

In combination with the supplied adapter primer the following gene specific primers were used: for 3'RACE the oligonucleotide N21965: 5'-TGGTTTCGTTACCGACAACCTTGTATCCC-3' (SEQ ID NO: 3) and for 5' RACE, the oligonucleotide N21968: 5'-GAGTTGGTCCCAGACAGACTTTTGTCGT-3' (SEQ ID NO: 4). The nucleotide sequence of the trAPAO polynucleotide, k0n0-395_6.5, from Exophiala spinifera is shown in SEQ ID NO: 5. The polypeptide sequence of trAPAO is shown in SEQ ID NO: 6.

A second clone of APAO containing an unspliced intron was also found. The polynucleotide sequence of trAPAO-I polynucleotide, k0n0-395_5.4, the intron containing clone, from Exophiala spinifera, can be found in SEQ ID NO: 7. The polypeptide sequence of trAPAO-I with the intron spliced out is shown in SEQ ID NO: 8. The polypeptide sequence of trAPAO-I without the intron spliced out is shown in SEQ ID NO: 9.

EXAMPLE 7

Heterologous Expression of trAPAO

Protein alignments generated with PileUp (GCG) indicate that k0n0-395_6.5 (trAPAO) is similar in size to other flavin amine oxidases and is close to being full length with respect to the amino terminus of their class of proteins. The k0n0-395_6.5 sequence contains a complete , β-α-βfold that is required for dinucleotide (FAD) binding, close to the amino end. The k0n0-395 sequence appears to lack only a variable amino terminal segment that varies in length from 5 amino acids in rat monoamine oxidases A & B to 40 amino acids in length in Aspergillus MAO-N. The function of these amino terminal extensions is not known; they are not recognizable as secretion signals. Based on the likely localization of the Exophiala APAO outside the cell membrane, the prediction is that k0n0-395 would have a signal sequence similar to that of the fumonisin esterase cloned from the same organism (U.S. Pat. No. 5,716,820, supra). Using GenomeWalker™, it is possible to clone the 5' end of the transcript and upstream genomic regulatory elements. However, the signal sequence is not expected to be critical to the functionality of the enzyme; in fact, the preferred strategy for heterologous expression in maize and *Pichia pastoris* involves replacing the endogenous signal sequence (if present) with an optimized signal sequence for the organism, e.g. barley alpha amylase for maize and the yeast alpha factor secretion signal for Pichia. In maize transformed with fumonisin esterase, the barley alpha amylase signal sequence gave higher amounts of functional protein than the native fungal signal, therefore replacement of the native fungal signal sequence is a logical optimization step. Since many of the amine oxidases have a positively charged amino acid near the N-terminus and upstream of the dinucleotide binding site, an additional optimization step included adding a codon for the lysine (K) to the N-terminus of the trAPAO clone (k0n0-395_6.5, SEQ ID NO: 5). This clone is designated K:trAPAO and can be seen in SEQ ID NOS: 10 and 11. The extra lysine is at amino acid 1 and nucleotides 1-3.

EXAMPLE 8

Pichia Expression of trAPAO

For optimum expression of trAPAO in *Pichia pastoris* the alpha mating factor signal peptide was fused in-frame with K:trAPAO coding sequence and can be seen in SEQ ID NOS: 16 and 17. The nucleotide sequence of clone pPicZalphaA:K:trAPAO contains a PCR-amplified insert comprising the k0n0-395 open reading frame with an additional lysine residue at the amino terminus, with a 5' EcoRI site and 3' NotI site for in-frame cloning into the alpha factor secretion vector pPicZalphaA. Nucleotides 1-267 contain the yeast α mating factor secretion signal. The amino acid sequence of shown in SEQ ID NO: 17 contains the trAPAO polypeptide produced from pPicZalphaA:K:trAPAO following transformation into *Pichia pastoris*.

For cloning into the *Pichia pastoris* expression vector, two cloning strategies were used. The cDNA k0n0-395_5.4 was generated by using end-to-end PCR using distal 5' and 3' GSPs with the adapter-ligated ds cDNA as template. pPicZalphaA, distal oligonucleotide primers were designed with 5' restriction enzyme sites that contain a 23–25 bp anchored overlap of the 5' end (sense strand) and 3' end (antisense strand) for cloning into the open reading frame of k0n0-395; the 3' primer also included the stop codon. The primer sequences are N23256: 5'-ggggaattcAAAGACAACGTTGCGGACGTGGTAG-3' (SEQ ID NO: 12) and N23259: 5'-ggggcggccgcCTATGCTGCTGGCACCAGGCTAG-3' (SEQ ID NO: 13). A second method was used to generate k0n0-395_6.5. 5' RACE and 3' RACE products were generated using a distal primer containing the necessary restriction enzyme sites, stop codon, etc as described above and paired with a "medial" GSP. The "medial primers" N21965: 5'-TGGTTTCGTTACCGACAACCTTGTATCCC-3' (SEQ ID NO: 14) for 3' RACE and for 5' race, the oligonucleotide N21968: 5'-GAGTTGGTCCCAGACAGACTTTTGTCGT-3' (SEQ ID NO: 15). Adapter-ligated ds cDNA was used as template. The isolated 5' and 3'-RACE fragments were digested with a restriction enzyme that cuts uniquely in the region of overlap, in this case Bgl I, isolated and ligated into the expression vector. The digestible restriction sites allow cloning of the inserts in-frame into EcoRI/NotI digested pPicZalphaA. pPicZalphaA is an *E. coli* compatible Pichia expression vector containing a functional yeast alpha factor secretion signal and peptide processing sites, allowing high efficiency, inducible secretion into the culture medium of Pichia. The resulting 1.4 kb bands were cloned into EcoRI/NotI digested pPicZalphaA plasmid.

SEQ ID NO: 16 contains the polynucleotide sequence of clone pPicZalphaA:K:trAPAO, a PCR-amplified insert that comprises the k0n0-395 open reading frame with an additional lysine residue at the amino terminus, and a 5' EcoRI site and 3' NotI site for in-frame cloning into the alpha factor secretion vector pPicZalphaA. SEQ ID NO: 17 contains the amino acid sequence of the trAPAO polypeptide produced from pPicZalphaA:K:trAPAO following transformation into *Pichia pastoris*. The alpha factor secretion signal and a lysine are added.

Pichia was transformed as described in Invitrogen Manual, Easy Select™ Pichia Expression Kit, Version B, #161219, with the trAPAO polynucleotide as described above with either an intron (trAPAO-I, negative control, no expression of active trAPAO since Pichia does not splice introns very efficiently) or without an intron (capable of making an active APAO protein). The Pichia culture fluids and pellets were assayed for APAO activity as described earlier.

The set of frozen six day Pichia culture cell pellets contained two samples with intron (SEQ ID NO: 7) in gene construct, # 11, # 14, and two samples without intron in gene construct (SEQ ID NO: 5), #6, # 52. The six day culture fluids from the same cultures were used to spike with crude fungal enzyme for positive controls.

The 50 $\mu$l cell pellets were resuspended in 150 $\mu$l cold 50 mM Na-phosphate, pH 8.0, and divided into two fresh 500 $\mu$l tubes. One tube was kept on ice with no treatment, the pellet suspension, and one tube was used for lysis. An equal volume of 0.1 mm zirconia-silica beads was added to each tube. The tubes were BeadBeat™ for 15 seconds then cooled on ice 5 minutes. This was repeated three times. The crude lysate was then transferred to another tube for assay or lysate suspension.

The TLC assays were performed as follows, the samples are 1) pellet suspensions; 10 $\mu$l; 2) lysate suspensions; 10 1$\mu$l; 3) media controls-mixed 5 $\mu$l media with 5 1$\mu$l crude fungal enzyme; 10 $\mu$l; 4) positive control-used crude fungal enzyme undiluted; 10 $\mu$l; 5) substrate control-used 50 mM Na-phosphate, pH8.0; 10 $\mu$l. Ten microliters of each sample plus 10 $\mu$l of $^{14}$C-AP1 (1 mg/ml, 50 mM Na-phosphate, pH 8) was incubated at room temperature for 6 days. One microliter of the sample was spotted onto C18 and C60 TLC plates. The C18 plates were developed in MeOH:4% KCl (3:2). The C60 plastes were developed in $CHCl_3$:MeOH:$CH_3COOH$:$H_2O$ (55:36:8:1). The plates were then air dried and then exposed to a PhosphorScreen™ for 2–3 days. A Storm™ PhosphorImager was used to develop the images.

A positive TLC result is obtained if an additional radioactive spot appears at a lower Rf of the produced AP1 modification earlier identified as 2-OP, a deaminated product of AP1. In samples # 6 and # 52 (without intron) the AP1-modifying enzyme activity (conversion of AP1 to 2-OP) was detected in pellet suspensions and pellet lysates, although the majority of activity was associated with the pellet suspensions. In samples #11 and #14 (with intron) a minimal amount of AP1-modifying enzyme activity was detectable in the pellet lysate of # 14 only, which indicates Pichia cannot process the intron efficiently.

This experiment verified APAO activity can be detected in Pichia transformants, which verifies that trAPAO as described functions correctly in degrading AP1. The activity is associated with cell suspensions, which show higher activity than pellet lysates. Pellet lysates may show less activity due to release of endogenous proteases during lysis of the cells.

EXAMPLE 9

Expression of trAPAO in *E. coli*

The vector for expressing K:trAPAO in *E. coli* is pGEX-4T-1. This vector is a prokaryotic glutathione S-transferase (GST) fusion vector for inducible, high-level intracellular expression of genes or gene fragments as fusions with *Schistosoma japonicum* GST. GST gene fusion vectors include the following features, a lac promoter for inducible, high-level expression; an internal lac Iq gene for use in any *E coli* host; and the thrombin factor Xa or PreScission Protease recognition sites for cleaving the desired protein from the fusion product. The insert of interest, k0n0-395_6.5 (K:trAPAO), was subcloned into the 5' EcoRI site and a 3' NotI site allowing in-frame expression of the GST:K:trAPAO fusion peptide. The polynucleotide sequence of the GST:K:trAPAO fusion can be found in SEQ ID NO: 18. The GST fusion with polylinker can be found at nucleotides 1 to 687. The K:trAPAO can be found at nucleotides 688 to 2076. The resulting polypeptide for the GST:K:trAPAO fusion can be seen at SEQ ID NO: 19. Amino acids 1 to 229 represent the GST fusion plus polyliker and amino acids 230 to 692 represent the K:trAPAO portion of the fusion.

*E. coli* was transformed with the pGEX-4T-1 vector containing K:trAPAO as described in BRL catalogue, Life Technologies, Inc. catalogue; Hanahan, D., *J. Mol. Biol.* 166:557 (1983) Jessee, J. *Focus* 6:4 (1984); King, P. V. and Blakesley, R., Focus 8:1, 1 (1986), and hereby incorporated by reference. The transformed *E. coli* was induced by addition of IPTG (isopropyl b-D-thiogalactopyranoside). Four samples of soluble extract and four samples of insoluble inclusion bodies were tested for trAPAO activity as described in Example 9. APAO activity was present in all soluble samples and two insoluble samples. Highest activity was found at 10 uM IPTG induction. Thus the pGEX-4T-1 vector containing k0n0-395__6.5 construct is capable of producing active APAO enzyme in *E. coli.*

EXAMPLE 10

The Complete Nucleotide Sequence of the Exophiala APAO Gene

Using Genome Walker, the complete nucleotide sequence of the Exophiala APAO gene was recovered. The nucleotide sequence described in SEQ ID NO: 5 is missing a portion of the 5' end of the native gene. The missing portion of the 5' end of the native gene is not necessary for expression of an active APAO enzyme, as can be seen in Examples 9 and 10. The complete nucleotide sequence of APAO can be seen in SEQ ID NO: 22. The translation of SEQ ID NO: 22 can be found in SEQ ID NO: 23.

EXAMPLE 11

Expression of APAO and ESP1 in Transgenic Maize Callus

One of the preferred constructs for expression in maize is the nucleotide sequence of the trAPAO fused to the barley alpha amylase signal sequence. The nucleotide sequence of K:trAPAO translational fusion with barley alpha amylase signal sequence, for expression and secretion of the mature trAPAO in maize can be seen in SEQ ID NO: 20. Nucleotides 1–72, represent the barley alpha amylase signal sequence; nucleotides 73–75, represent the added lysine residue; and nucleotides 76–1464, represent the trAPAO cDNA. The amino acid sequence translation of SEQ ID NO: 20 can be found in SEQ ID NO: 21. Amino acids 1 to 24 represent the barley alpha amylase signal sequence and amino acids 25 to 463 is the sequence of K:trAPAO.

Maize embryos were transformed with linear DNA (insert, lacking a bacterial antibiotic resistance marker), derived from constructs containing three transcription units: 1) a PAT selectable marker gene (Wohlleben et al., *Gene* 70, 25–37 (1988)), 2) flumonisin esterase ESP1 fused to a barley alpha amylase signal sequence, and 3) full length APAO without or with an amino-terminal barley alpha amylase signal sequence, (P13603, comprising a PAT selectable marker fused to a 35S promoter, fumonisin esterase ESP1 fused to a barley alpha amylase signal sequence and the ubiquitin promoter, and APAO fused to the ubiquitin promoter and P13611, comprising a PAT selectable marker fused to the 35S promoter, fumonisin esterase ESP1fused to a barley alpha amylase signal sequence and the ubiquitin promoter and APAO fused to a barley alpha amylase signal sequence and the ubiquitin promoter). In these constructs both ESP1 and APAO were linked to the maize ubiquitin promoter and first intron. In a third construct, the same three transcriptional units were cloned into an Agrobacterium T1 vector (P15258, the construct comprises a PAT selectable marker, fumonisin esterase ESP1 fused to a barley alpha amylase signal sequence and APAO). Stably transformed callus or T0 plants regenerated from callas were tested for ESP 1 and APAO activity in buffer extracts of leaf tissue, using radiolabeled FB1 and/or AP1 and C18 thin-layer chromatography. Positive controls consist of non-transformed tissue spiked with *E coli*-expressed recombinant ESP1 or APAO. The results indicate that both ESP1 and APAO activities can be detected in transgenic maize callus and plants.

Expression of ESP1 and APAO in Transgenic Callus

| Construct | Sample ID Number | ESP1 activity (TLC) | APAO activity (TLC) |
|---|---|---|---|
| 13603 | 3065.031-2 | + | + |
| 13603 | 3065.034-3 | + | + |
| 13603 | 3065.1117-3 | + | + |
| 13603 | 3065.11s7-n13 | + | + |
| 13603 | 3065.117-2 | + | + |
| 13603 | 3065.1115-2 | + | + |
| 13603 | 3065.1115-6 | + | + |
| 13603 | 3065.1112-1 | + | + |
| 13603 | 3065.118-6 | + | + |
| 13603 | 3065.11s3-1 | + | + |
| 13603 | 3065.11s1-13 | + | + |
| 13603 | 2805.762-2 | + | + |
| 13603 | 3065.1110-2 | + | + |
| 13603 | 3065.039-2 | + | + |
| 13611 | 3065.293-3 | + | + |
| 13611 | 3065.263-1 | + | + |
| 13611 | 3070.24.2.3 | + | + |

Transgenic plants were regenerated from the transgenic callus positive for both ESP1 and APAO activity by standard methods known in the art. Enzyme activity was tested as described previously. As can be seen below transgenic maize plants can successfully express both ESP1 and APAO enzymes.

Expression of APAO and ESP1 in Transgenic Maize Plants (T0)

| Construct | Sample ID Number | ESP1 activity (TLC) | APAO activity (TLC) |
|---|---|---|---|
| 13603 | 910080 | + | + |
| 13603 | 910081 | + | + |
| 13603 | 917065 | + | + |

Another preferred construct for expression of APAO in a plant is targeting the APAO to the peroxisome. Maize embryos were bombarded with insert containing APAO operably linked to ubiquitin promoter and a peroxisomal targeting sequence (Gould, et al., *J Cell Biol* 108:1657–1664 (1989)); ESP1 operably linked to ubiquitin promoter and the barley alpha amylase signal sequence; and a selectable marker of PAT operably linked to the 35S promoter (construct number 114952). Negative controls were unbombarded embryos/callus. Positive controls were unbombarded embryos/callus spiked with purified enzyme. Transformed callus was then tested for ESP1 or APAO activity as previously described. Out of 67 samples tested 18 samples contained both ESP1 activity and APAO activity. Peroxisomally targeted APAO and apoplast targeted fumonisin esterase can both be successfully expressed in a plant cell.

Another preferred construct for expression of APAO in a plant is targeting the APAO to the mitochondrial membrane. A C-terminal extension is required for targeting monoamine oxidases MAO-A and MAO-B to mammalian outer mitochondrial membranes. An MAO-A, MAO-B, or functionally similar C-terminal extension can be fused in-frame to APAO or trAPAO to facilitate localization of this enzyme to the mitochondrial membrane of maize or other transformed species.

EXAMPLE 12

Comparison of APAO Sequence With Other Sequences

The Exohphiala cDNA of APAO (SEQ ID NO: 22) contains an 1800 bp open reading frame coding for a 600 amino acid polypeptide (SEQ ID NO: 23) with divergent homology to two classes of proteins. The carboxy three-fourths of APAO (amino acids 137 to 593) is strongly homologous to flavin amine oxidases, a group of enzymes catalyzing the oxidative deamination of primary amines at carbon 1. The amine oxidase function of the carboxy terminal domain was confirmed by expression of a truncated APAO polypeptide (from 137 to 600) in both *Pichia pastoris* and *E. coli*, using AP1 as a substrate (see Example 9). The amino terminal portion of APAO, in contrast, (from approx. 5 to 134) shows significant homology to a group of small deduced open reading frames (ORFs) reported in several bacteria and blue-green algae, as well as several higher organisms. These ORFs code for small proteins of unknown function, ranging in size from 14 to 17 kDA. The juxtaposition of these divergent homologies in a single polypeptide has not been reported previously.

Flavin amine oxidases (E.C. 4.1.4.3) are a group of flavoenzymes found in both higher and lower organisms, and serve a variety of functions in catabolism. They catalyze the oxidative deamination of primary amino groups located at the C-1 position of a variety of substrates, resulting in an aldehyde product plus ammonia and hydrogen peroxide. The APAO enzyme described in this report is the first flavin amine oxidase known to attack a primary amine not located at C-1 (i.e. C-2 of AP1) and resulting in a keto rather than aldehydic product. IHowever, amino acid oxidases, while not closely related to flavin amine oxidases, are flavoenzymes that oxidize a C-2 amine adjacent to a C-1 carboxyl group.

The monoamine oxidases MAO A & B, (from human, bovine, and trout), are localized in the mitochondrial outer membrane of higher organisms and regulate the level of neurotransmitters. Microbial examples include a fungal amine oxidase (*Aspergillus niger* (niger) MAO-N) involved in amine catabolism, and a bacterial putrescine oxidase from a gram (+) bacterium (Micrococcus rubens.). The primary polypeptides vary in length from 478 to 527 amino acids, and share regions of high amino acid sequence conservation at the 5' end as well as at various points through the coding region. Protein alignments generated with PileUp (GCG) indicate that trAPAO contains all conserved domains found in this class of proteins including those near the 5' end.

The amine oxidase domain of trAPAO contains several key features shared by this class of enzymes, including an amino-terminal dinucleotide (ADP) binding region characterized by a beta-alpha-beta stretch containing three invariant glycines (G-X-G-X-X-G) in the beta-alpha turn. In trAPAO, this sequence is (DVVVVGAGLSG). This region is involved in FAD binding. Absent are several features unique to the mammalian amine oxidases, including several essential cysteine residues (Wu et al., *Mol Pharm* 43:888 (1993)), one of which (Cys-406 of MAO-A) is involved in covalent binding of FAD, and a carboxy-terminal extension that has been demonstrated to be involved in transporting to and anchoring the MAO in the outer mitochondrial membrane. The Aspergillus enzyme MAO-N has been demonstrated to contain non-covalent FAD, and also lacks the conserved cysteine. Therefore it is possible that the Exohphiala APAO enzyme has a non-covalent FAD. The Aspergillus MAO-N has a carboxy-terminal tripeptide Ala-Arg-Leu that is involved in peroxisomal targeting and localization; this, sequence is absent from Exohphiala APAO.

The amine oxidase domain of trAPAO contains a total of seven cysteines, compared to ten for the Aspergillus enzyme and only two for the Micrococcus enzyme. The mammalian MAO enzymes contain variable numbers of cysteines (at least ten), some of which are highly conserved (including the FAD binding residue mentioned above). The trAPAO sequence also has two putative glycosylation sites (NDS, NQS) towards the amino end.

The purpose of the amino-terminal extension of APAO and the basis for its homology to a group of 14–17 kDa proteins is not clear. In Synechocystis, a similar polypeptide ORF is located immediately upstream of the NADP-dependent glutamine dehydrogenase (gdhA) and has been shown to be required for functional expression of gdhA (Chavez et al, 1995). However, in trAPAO the domain is clearly not necessary for enzymatic activity, as shown by the results of the expression experiments using the truncated APAO. An interesting clue comes from the frequent association of this small ORF with gene clusters involved in oxidoreductase activity in bacteria, or induced by heat stress in mice, suggesting a possible role in redox protection. A byproduct of amine oxidase activity is hydrogen peroxide. Flavoenzymes and other redox enzymes are often susceptible to inactivation by hydrogen peroxide (Schrader et al., *App Microb Biotechnol* 45:458; Aguiree, et al., *J Bacteriol* 171:6243 (1989)), and it is possible that this protein has a protective role against oxidants such as hydrogen peroxide. Alternatively, this domain could be involved in enzyme function, localization or association of the enzyme with other structures. No signal peptide region can be detected in this amino terminal region.

In multiple sequence alignment using GCG PileUp, trA-PAO is most similar to putrescine oxidase of *Micrococcus rubens*, Swissprot accession number P40974, (30% identical amino acids, 40% similar). Homology with several mammalian monoamine oxidases A and B, Swissprot accession numbers P21397 (*Homo Sapiens* mao a), P19643 (*Rattus norvegicus* mao b), P21396 (*Rattus norvegicus* mao a), and P21398 (*Bos taurus mao a*), is somewhat less, ranging from 25 to 28% identity and 36 to 40% similarity. Homology to the only other fungal flavin amine oxidase known, MAO-N from *Aspergillus niger* (Swissprot accession number P46882), is somewhat lower (24% identical, 34% similar). The microbial enzymes are considerably divergent from each other, while the mammalian monoamine oxidases share 65 to 87% identity.

The amino terminal domain (ATD) of APAO also shows homology to a 14.5 kD protein from human and rat phagocytes that shows translational inhibition activity in vitro (Swissprot accession # P52758, P52759) Schmiedeknecht, et al.,*Eur J Biochem* 242 (2), 339–351 (1996)), and includes a heat-responsive protein from mouse (Samuel, et al., *Hepatology* 25 (5), 1213–1222 (1997)). This suggests that this family of proteins is involved in regulating cellular metabolism. No example exists in which this domain is fused to a larger protein domain, however, making APAO unique. Without intending to be limited by theory, all of this suggests, that this domain plays a regulatory role in APAO gene expression, possibly to prevent translation of the message when it is not needed. This raises the question of how translation of the message is restored when active enzyme is required by the Exophiala cell. Possibly there are alternative start sites that begin downstream of the inhibitor domain; or proteolysis, complexing, degradation, or phosphorylation/dephosphorylation of the inhibitor domain when it is not needed. The first possibility is less likely because there are no other ATG codons prior to the ATG at 122–124 that constitutes the predicted start site of APAO. The second possibility cannot be easily tested, although there is a casein kinase site in the ATD. Alternative roles for the ATD include oligomerization of the APAO protein, or anchoring the protein to some intracellular site, such as the membrane.

A parallel example of regulatory control over another flavoenzyme, human flavin monooxygenase 4 (FMO-4), by a C-terminal extention has been reported (Itagaki, et al.,*J of Biol Chem* 271(33): 20102–20107 (1996)). In this case the introduction of a stop codon prior to the 81 base C-terminal extension allowed expression of active enzyme in heterologous systems. The role of the C-terminal portion was not elucidated, however. In another example, alternative splicing led to a shorter gene product that complexed with and interfered with the function of the normally spliced version (Quinet, et al., *J of Biol Chem* 268(23): 16891–16894 (1993)). In another case, an alternative splicing-generated insert in another protein led to inhibition of cell growth (Bhat, et al., *Protein Engineering* 9(8): 713–718 (1996)). In yet another variation, fas/Apol splicing variants prevent apoptosis, apparently through a 49 amino acid domain shared by all variants ((Papoff, et al., *J of Immunology* 156(12): 4622–4630 (1996)).

EXAMPLE 13

Making a Fusion Protein Containing Fumonisin Esterase and AP Amine Oxidase Activity in the Same Polypeptide The enzyme activities of fumonisin esterase and AP amine oxidase can be combined in a single polypeptide by using the open reading frames together either with or without a spacer region between the two polypeptides. This creates a hybrid protein with dual enzyme activities that can be exported as a unit to the apoplast, and will allow both enzyme activities to be conveniently localized to the same area of the cell wall. The two cDNA's can be combined in either order, but the preferred method is to link them in the order $NH_3$-Esterase:Amine Oxidase-COOH. The spacer, if present, may consist of a short stretch of amino acids such as GGGSGGGS, or a set of amino acids that comprises a protease cleavage site that can be acted on by an apoplastic protease. This would result in the production of stoichiometric amounts of both esterase and APAO enzymes in the apoplast.

The esterase-APAO fusion protein can be made with either the fumonisin esterase from *E. spinifera* 2141.19 (ESP1) or fumonisin esterase from bacterium 2412.1 (BEST1). Since the pH range for maximum activity of BEST1 is similar to that of APAO (range 6.0 to 8.0), these may present the most effective combination in fusion form. As described in previous examples these fusion sequences can be placed in the appropriate expression vectors and used to express proteins in either bacteria or plants.

The nucleotide sequence of ESP1 contains three nucleotide differences and three corresponding amino acid differences for the ESP1 sequence disclosed in pending U.S. applications Ser. Nos. 08/888,950 and 08/888,949, both filed Jul. 7, 1997. Both the sequences disclosed in the present application and the sequences disclosed in the pending U.S. applications contain functional fumonisin esterase genes. For the purposes of the present invention, either the original ESP1 sequences or the ESP1 sequences disclosed may be used in combination with the APAO sequences or in fusion sequences. The nucleotide sequence of a BAA:ESP1:K:trAPAO construct for plant expression can be found in SEQ ID NO: 24 and the translation in SEQ ID NO: 25. The nucleotide sequence for a BAA:BEST1:K:trAPAO construct for plant expression can be found in SEQ ID NO: 26 and the translation in SEQ ID NO: 27. The nucleotide sequence of a GST:ESP1:K:trAPAO fusion for bacterial expression in a pGEX-4T-1 or similar vector can be found in SEQ ID NO: 28 and the translation in SEQ ID NO: 29. The nucleotide sequence for a GST:BEST1:K:trAPAO fusion for bacterial expression in a pGEX-4T-1 or similar vector can be seen in SEQ ID NO: 30 and the translation in SEQ ID NO: 31.

EXAMPLE 14

APAO Substrate Studies

The following assay was used to determine the substrate specificity of the APAO enzyme. Reaction mix: 436 μl of 200 mM Na-phosphate, pH8.0; 50 μl substrate (10 mM); 2 μl Amplex Red (1 mg in 200 μl DMSO); and 2 μl of Peroxidase (5000 U/ml). The APAO enzyme was recombinant enzyme produced as GST fusion in *E. coli*, purified over a glutathione affinity column and cleaved with thrombin to remove the GST. All components were mixed at room temperature. The initial rate was determined in a spectrophotometer at 572 nm over one minute by absorbance units/second (BLANK). Ten microliters of APAO at 70 ug/ml was added and mixed. The initial rate was again determined at 572 nm over one minute in absorbance units/second (SAMPLE). The rates were converted to absorbance units/minute. The BLANK value was subtracted from the SAMPLE value. The absorbance units were converted to $\mu$M $H_2O_2$ wherein 1 $\mu$M $H_2O_2$ equals 0.138 absorbance units at pH 8.0.

SUBSTRATES FOR APAO

| SUBSTRATE | RATE $\mu$M $H_2O_2$/min |
|---|---|
| 1 mM Fumonisin B1 | 0.1429 |
| 1 mM AP1 | 0.8876 |
| 0.5 mg/mL Fumonisin B2 | 0.3058 |
| 1 mM Fumonisin B3 | 0.1449 |
| 0.5 mg/mL Fumonisin B4 | 0.1728 |
| 1 mM norepinephrine | 0.0087 |
| 1 mM epinephrine | 0.0071 |
| 1 mM dopamine | 0.0040 |
| 1 mM spermine | 0.0002 |

NOT SUBSTRATES FOR APAO (defined as compounds resulting in less than 1% conversion to hydrogen peroxide by APAO relative to AP1 under similar conditions of time, pH, temperature, and substrate concentration)

2-phenylethylamine, spermidine, EDTA-$Na_2$, tryptamine, putrescine, benzamidine, serotonin, cadaverine, Pefabloc SC, tyramine, 1,3-diaminopropane, leupeptin, histamine, hydroxylamine, aprotinin, deprenyl, Fumonisin C4, isoniazid, sphingosine, phenelzine, sphinganine, phytosphingosine, D-alanine, DL-alanine, L-arginine, L-asparagine, L-aspartic acid, D-aspartic acid, L-cysteine, L-glutamine, L-gltutamic acid, glycine, L-histidine, L-isoleucine, L-leucine, L-lysine, DL-lysine, L-methionine, DL-methionine, L-phenylalanine, L-proline, L-threonine, L-tryptophan, L-tyrosine, L-valine.

EXAMPLE 15

Removal of Glycosylation Sites from APAO

Some cytosolic enzymes, when engineered for secretion by fusion with a heterologous signal peptide, lack function due to glycosylation at one or more potential glycosylation sites (amino acid consensus sequence N-X-S/T) that are not normally glycosylated in the native environment (Farrell L B, Beachy R N, Plant Mol Biol 15(6):821–5 (1990)). Since APAO lacks a recognizable signal sequence, it may be cytoplasmically localized in Exophiala spinifera, although secretion by some other method not involving a signal peptide cannot be ruled out. APAO contains two potential glycosylation sites, which can potentially be glycosylated, when APAO is secreted in a plant or other eukaryotic cell. These glycosylation sites can be eliminated without affecting protein function by site-directed mutagenesis using standard protocols (such as kits available from CLONTECH Laboratories, Inc. (Palo Alto, Calif.)).

SEQ ID NO: 33 shows the amino acid sequence of a GST:APAO in which two amino acids of APAO have been changed by site-directed mutagenesis to eliminate two potential glycosylation sites. The polynucleotide sequence of SEQ ID NO: 33 can be found in SEQ ID NO: 32. The first mutation changes asparagine at amino acid 201 of APAO to serine, and the second mutation changes serine at amino acid 206 of APAO to asparagine.Other mutations at either amino acid 200, 201, 202, 203, 204, 205, 206, or 207 of APAO, or a combination of these, can also be engineered to accomplish the removal of the glycosylation signal (Mellquist, J. L., Kasturi, L., Spitalnik, S. L., and Shakin-Eshelman, S. H., 1998. The amino acid following an Asn-X-Ser/Thr sequence is an important determinant of n-linked core glycosylation efficiency. Biochemistry 37:6833).

Other modifications to APAO can be made to improve its expression in a plant system, including site-directed mutagenesis to remove selected cysteine residues, which may be detrimental to proper folding when the protein is secreted into the endomembrane system for delivery to the apoplast. Cysteines are present at residues 64, 109, 167, 292, 351, 359, 387, 461, and 482, and may or may not be involved in disulfide crosslinking in mature, folded APAkO. Using standard methods of site-directed mutagenesis, one or more of these residues can be substituted with alanine or other suitable amino acid, resulting in a modified version of APAO that retains its activity and specificity but displays better activity and stability in an extracellular environment. It is possible that one or more cysteines is involved in covalent attachment of the FAD moiety to the APAO protein, and elimination of this cysteine would be expected to reduce or abolish activity.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. An isolated polynucleotide comprising a member selected from:
   a) a polynucleotide that encodes a polypeptide selected from SEQ ID NO: 6, SEQ ID NO: 11, and SEQ ID NO: 23; and
   b) a polynucleotide comprising a polynucleotide selected from SEQ ID NO: 5, SEQ ID NO: 10, and SEQ ID NO: 22.

2. A recombinant expression cassette comprising a member of claim 1.

3. A vector comprising the recombinant expression cassette of claim 2.

4. A host cell comprising the recombinant expression cassette of claim 2.

5. The host cell of claim 4 wherein the cell is a plant cell.

6. A transformed plant cell comprising the polynucleotide of claim 1.

7. The transformed plant cell of claim 6 wherein the plant cell is selected from the group consisting of maize, sorghum, wheat, tomato, soybean, alfalfa, sunflower, canola, cotton, and rice.

8. A plant comprising the polynucleotide of claim 1.

9. A seed from the plant of claim 8.

10. An isolated polynucleotide comprising the polynucleotide of claim 1 fused to a plant signal sequence.

11. The polynucleotide of claim 10 wherein the plant signal sequence is apoplast targeting sequence.

12. A method of reducing pathogenicity of a fungus producing fumonisin or a structurally related mycotoxin, comprising:
   a) transforming a plant cell with a vector comprising the polynucleotide of claim 1 operably linked to a promoter;
   b) growing the plant cell under plant growing conditions; and
   c) inducing expression of said polynucleotides for a time sufficient for amounts of the fumonisin esterase and APAO enzymes to accumulate to levels that can inhibit the fungus.

13. A method of making an APAO enzyme comprising the steps of:
   a) expressing the nucleic acid of claim 1 in a recombinantly engineered cell; and
   b) purifying the enzyme.

14. A method of making an APAO enzyme comprising the steps of:
   a) expressing the nucleic acid of claim 1 in a plant; and
   b) purifying the enzyme from the plant seed or other plant parts.

* * * * *